(12) United States Patent
Wynne et al.

(10) Patent No.: US 11,666,686 B2
(45) Date of Patent: Jun. 6, 2023

(54) AMTIMICROBIAL SILICONES

(71) Applicant: WYNNVISION, LLC, Richmond, VA (US)

(72) Inventors: Kenneth J. Wynne, Midlothian, VA (US); Olga Zolotarskaya, Richmond, VA (US); Rebecca Jarrell, Williamsburg, VA (US); Kennard Brunson, Richmond, VA (US); Chenyu Wang, Midlothian, VA (US)

(73) Assignee: WynnVision, LLC, Richmond, VA (US)

( * ) Notice: Subject to any disclaimer, the term of this patent is extended or adjusted under 35 U.S.C. 154(b) by 0 days.

(21) Appl. No.: 17/867,252

(22) Filed: Jul. 18, 2022

(65) Prior Publication Data
US 2023/0029153 A1 Jan. 26, 2023

Related U.S. Application Data

(63) Continuation of application No. PCT/IB2021/050326, filed on Jan. 17, 2021.
(Continued)

(51) Int. Cl.
A61L 29/06 (2006.01)
A61L 31/06 (2006.01)
(Continued)

(52) U.S. Cl.
CPC ............. *A61L 29/06* (2013.01); *A61L 29/085* (2013.01); *A61L 31/06* (2013.01); *A01N 25/10* (2013.01);
(Continued)

(58) Field of Classification Search
None
See application file for complete search history.

(56) References Cited

U.S. PATENT DOCUMENTS 3,131,221 A 4/1964 Remes
3,846,353 A 11/1974 Grotta
(Continued)

FOREIGN PATENT DOCUMENTS

CN 106565958 A 4/2017
WO WO2013005036 A1 1/2013
(Continued)

OTHER PUBLICATIONS

English language translation of WO 2013/118736 A1. (Year: 2013).*
(Continued)

*Primary Examiner* — Dominic Lazaro
(74) *Attorney, Agent, or Firm* — Law Office of John K. Pike, PLLC

(57) ABSTRACT

A composition, comprising:
a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof.

28 Claims, 31 Drawing Sheets

Related U.S. Application Data

(60) Provisional application No. 63/068,947, filed on Aug. 21, 2020, provisional application No. 63/014,102, filed on Apr. 22, 2020, provisional application No. 62/962,922, filed on Jan. 17, 2020.

(51) Int. Cl.
    *A61L 29/08*     (2006.01)
    *A01N 25/10*     (2006.01)
    *A01N 33/04*     (2006.01)
    *A61L 29/16*     (2006.01)

(52) U.S. Cl.
    CPC .............. *A01N 33/04* (2013.01); *A61L 29/08* (2013.01); *A61L 29/16* (2013.01); *A61L 2300/204* (2013.01); *A61L 2300/404* (2013.01); *A61L 2420/02* (2013.01)

(56) References Cited

U.S. PATENT DOCUMENTS

| | | |
|---|---|---|
| 4,612,337 A | 9/1986 | Fox |
| 4,917,686 A | 4/1990 | Bayston |
| 5,385,736 A | 1/1995 | Kappes |
| 5,393,789 A | 2/1995 | Eggensperger |
| 6,264,936 B1 | 7/2001 | Sawan |
| 7,151,139 B2 | 12/2006 | Tiller |
| 8,372,384 B2 | 2/2013 | Chisholm |
| 8,415,497 B2 | 4/2013 | Najafi |
| 8,962,772 B2 | 2/2015 | Ding |
| 9,089,407 B2 | 7/2015 | Schaer |
| 9,127,173 B2 | 9/2015 | Lee |
| 9,268,064 B2 | 2/2016 | Chang |
| 9,809,717 B2 | 11/2017 | Ali |
| 10,117,436 B2 | 11/2018 | Wynne |
| 10,149,471 B2 | 12/2018 | Jiang |
| 2010/0076546 A1 | 3/2010 | Dias |
| 2010/0113871 A1 | 5/2010 | Athanasius |
| 2011/0124772 A1 | 5/2011 | Wang |
| 2012/0061877 A1 | 3/2012 | Britt |
| 2017/0266694 A1 | 9/2017 | Senzaki |
| 2018/0036702 A1 | 2/2018 | Wellings |
| 2018/0125620 A1 | 5/2018 | Hussain |
| 2018/0362714 A1 | 12/2018 | Grubbs |
| 2019/0240663 A1 | 8/2019 | Miller |

FOREIGN PATENT DOCUMENTS

| | | | |
|---|---|---|---|
| WO | WO-2013118736 A1 * | 8/2013 | ............ C08F 220/18 |
| WO | WO2013118736 A1 | 8/2013 | |
| WO | WO2016139322 A1 | 9/2016 | |

OTHER PUBLICATIONS

P. Gilbert, Cationic antiseptics: diversity of action under a common epithet, Journal of Applied Microbiology 2005, 99, 703-715.
Thomas B. Rauchfuss, Insights into the Hydrolytic Polymerization of Trimethoxymethylsilane. Crystal Structure of (MeO)2MeSiONa, Inorg. Chem. 2016, 55, 5744-5746.
Jakub Siegel, Antimicrobial Treatment of Polymeric Medical Devices by Silver Nanomaterials and Related Technology, Int. J. Mol. Sci. 2017, 18, 419.
Romain Bordes, Formation, physicochemical and interfacial study of carbamate surfactants, Journal of Colloid and Interface Science 511 (2018) 84-91.
E. Elif Hamurcu, Solubility Parameter of a Poly(dimethylsiloxane) Network, J. Polym. Sci.: Part B: Physics, vol. 32 (1994) 591-594.
George H. Nancollas, Heterogeneous nucleation of calcium phosphates on solid surfaces in aqueous solution, J. Biomed. Mater. Res., vol. 35, 93-99 (1997).
V.P. Venugopalan, Polydimethyl siloxane based nanocomposites with antibiofilm properties for biomedical applications, J Biomed Mater Res Part B 2017:105B:1075-1082.
C. W. Jones, Effect of Amine Surface Coverage on the Co-Adsorption of CO2 and Water: Spectral Deconvolution of Adsorbed Species, J. Phys. Chem. Lett. 2014, 5, 4194-4200.
Nasreddine Kebir, Preparation of bactericidal cationic PDMS surfaces using a facile and efficient approach, Applied Surface Science 360 (2016) 866-874.
S. S. J. Leong, Antimicrobial functionalization of silicone surfaces [. . . ] and salt-resistant properties, Acta Biomaterialia 10 (2014) 258-266.
Hitesh Handa, A review of the recent advances in antimicrobial coatings for urinary catheters, Acta Biomaterialia 50, Dec. 1, 2016, 20-40, Elsevier.
Steven Roest, Synthesis of quaternary ammonium coated surfaces: Physico-chemistry, bacterial killing and phagocytosis, Thesis, 2016, University of Groningen, 1-128.
Joseph P. Truant, Relationship of Chemical Structure and Antimicrobial Activity of Alkyl Amides and Amines, Antimicrobial Agents and Chemotherapy, Dec. 1972, p. 492-498.
P. A. Walters, Surface-Bonded Antimicrobial Activity of an Organosilicon Quaternary Ammonium Chloride, Applied Microbiology, vol. 24, No. 6, Dec. 1972, p. 859-863.
B. Gottenbos, In vitro and in vivo antimicrobial activity of covalently coupled quaternary ammonium silane coatings on silicone rubber, Biomaterials 23 (2002) 1417-1423.
K. Matyjaszewski, Permanent, non-leaching antibacterial surfaces—2: How high density cationic surfaces kill bacterial cells, Biomaterials 28 (2007) 4870-4879.
John H. L. Beal, A rapid, inexpensive surface treatment for enhanced functionality of polydimethylsiloxane microfluidic channels, Biomicrofluidics 6, 036503 (2012), 1932-1058.
Koon Gee Neoh, Inhibition of *Escherichia coli* . . . Medical Grade Silicone Surface, Biotechnology and Bioengineering, vol. 109, No. 2, Feb. 2012.
Ana L. Flores-Mirales, Urinary Catheter Coating Modifications: The Race against Catheter-Associated Infections, Coatings 2020, 10, 23, Dec. 29, 2019, 1-25.
J.R. Steinmetz, Factors contributing to the stability of alkoxysilanes in aqueous solution, Silanes and Other Coupling Agents, Ed. K.L.Mittal, VSP 1992, 91-104.
Eva Onofrey, Cationic Antagonism of the Antibacterial Action of Amines, J. Biol. Chem. 1954, 210:193-201.
Jian Shen, Facile surface modification of silicone rubber [. . . ] blood compatibility, Materials Science and Engineering C 33 (2013) 3865-3874.
Christopher L. Kitchens, Reduced Reactivity of Amines against Nucleophilic Substitution via Reversible Reaction with Carbon Dioxide, Molecules 2016, 21, 24.
Naval Research Laboratory, Broad Spectrum Biocide [. . . ] Coating, TechLink, May 2020, https://techlinkcenter.org/technologies/broad-spectrum-biocide-and-antiviral-coating.
Henny C. Van Der Mei, Effects of Quaternary Ammonium Silane Coatings [. . . ] Tracheoesophageal Shunt Prostheses, Applied and Environmental Microbiology, May 2006, p. 3673-3677.
Joseph P. Truant, Relationship of Chemical Structure [. . . ] Alkyl Amides and Amines, Antimicrobial Agents and Chemotherapy, Dec. 1972, vol. 2, No. 6, p. 492-498.
Jianzhong Jiang, Facile synthesis of mesoporous silica by CO2/N2 switchable templates using a convenient compound, RSC Adv., 2017, 7, 25066.
Ingo Köper, Biocompatible anti-microbial coatings for urinary catheters, RSC Adv., 2016, 6, 53303.
Joerg C. Tiller, Antimicrobial Polymers in Solution and on Surfaces: Overview and Functional Principles, Polymers 2012, 4, 46-71.
George M. Whitesides, Solvent Compatibility of Poly(dimethylsiloxane)-Based Microfluidic Devices, Anal. Chem. 2003, 75, 6544-6554.
International Search Report & Written Opinion, PCT/IB2021/050326, WO 2021/144769A1, dated May 24, 2021.

* cited by examiner

ANTIMICROBIAL SILICONES

RELATED APPLICATIONS

This application claims the benefit of U.S. Application Nos. 62/962,922, filed Jan. 17, 2020, 63/014,102, filed Apr. 22, 2020, and 63/068,947, filed Aug. 21, 2020, the entire contents of each of which are hereby incorporated by reference, the same as if set forth at length.

GOVERNMENT INTEREST

The present application was made with the support of NIH 5R44DK103398 and NIH R44HL142391. The government has certain rights in the invention.

BACKGROUND

The human body holds in abundance a delicate balance of microbial ecosystems, ideally culminating in a state of homeostasis. A new and revised study published in 2016 estimates that the body contains approximately 3.84e13 bacteria, existing both externally and internally. Thus, when these balances are disturbed by any multitude of extenuating factors, opportunistic pathogens become a major concern to any individual's overall health. Specifically, nosocomial or hospital acquired infections (HAIs) being one of highest concerns amongst the medical community, with 1 out of every 10 hospitalized patients receiving an infection upon admission. A study published in 2011 concerning trauma patients reported a mortality rate of 90,000 deaths per year due to HAIs and accounted for more than 35 billion dollars in additional costs. Oftentimes, it is life-saving medical devices such as catheters and ventilators that become the vehicle from which these bacterial, viral and fungal infections originate. The present inventors have diligently studied these problems and have now surprisingly and unexpectedly arrived at the present invention, which can desirably provide sanctuary to these patients from such preventable infections. The present compositions, which describe certain amine-treated silicones, methods for their making, and their use, enable benefits such as the reduction of HAIs along with the associated mortality rates and burdensome economic costs, and other benefits.

Conventional and antimicrobial catheters are flexible tubular devices that are inserted through the urethra and used to pass fluids to or from the urinary tract. Such catheters are often comprised of silicone and designed to reduce urinary tract infections through means such as hydrophilic or silver-eluting coatings. However, silver has been reported to have potential cytotoxic effects, and there continue to be incidences of urinary tract infections with existing silicone catheters. Other challenges include increasing resistance of bacteria to antibiotics and antimicrobials and prevention of biofilm formation. In response to an unmet need, the present invention improves upon existing silicone catheters to reduce rates of catheter associated urinary tract infections (CAUTIs).

Driven by the ongoing coronavirus COVID-19 pandemic, the present inventors have also considered the antiviral efficacy of the (so-called herein) "Antimicrobial-But-Cytocompatible" silicone or "ABC-silicone". One of the major modes of transmission for COVID-19 is contact, often via small droplets produced when breathing out. The small droplets may fall onto surfaces where the virus can survive up to 72 hours. People may be infected by touching a contaminated surface. CDC recommends cleaning and disinfecting frequently touched surfaces, such as doorknobs, light switches and keyboards, daily to prevent being infected.

Examples of existing antiviral materials include: (1) hydrogels allowing controlled release of antiviral agents (polysorbate 204, monocaprin and acyclovir) to reduce viral activity on surfaces. This technology is facing increasing problems with drug resistance development; (2) silver and copper impregnated materials have been used in food contact and packaging application to control viral contamination but safety of metal components has caused increasing concern; and (3) polymeric quaternary ammonium compound, which have been successful in laboratory testing but stability and durability in real applications has not been evidenced yet.

against *K. pneumoniae* with increasing C12 wt % in feed(1, 2, 4, 6 and 8 feed wt %); B, Enlarged images showing close-ups of F-C12-1(25) and F-C12-2(25) of disks. F-C12-2(25) shows complete kill with no detectable ZOI. F-C12-1.5(25) has no ZOI, but effects incomplete kill.

Figure 13:
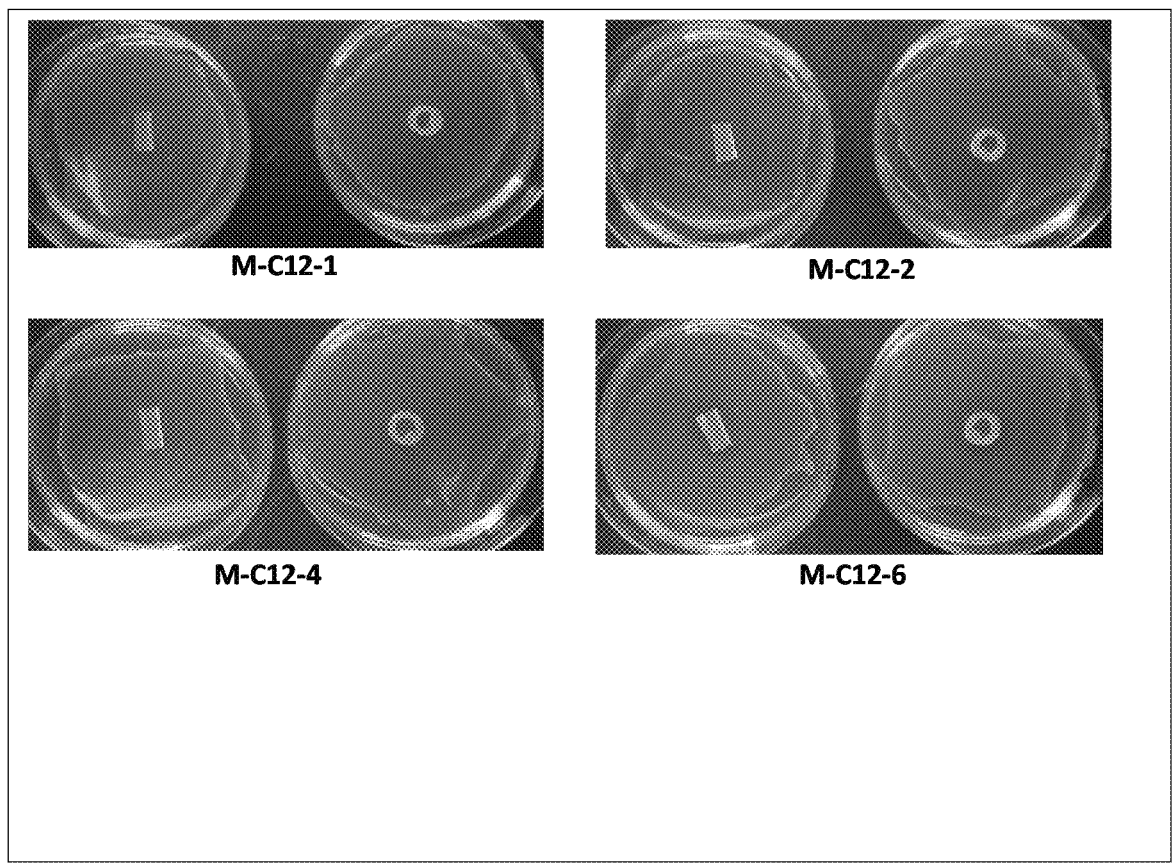

FIG. 13. *E. coli* with concentration of $10^9$ cfu/mL was uniformly generated as a "lawn" on LB medium agar. Images show ZOI against *E. coli* for medical grade silicone catheter tubes treated with C12 amine feed concentrations of 1 wt %, 2 wt %, 4 wt %, and 6 wt %. No ZOI is observed for M-C12-1, M-C12-2 or M-C12-4; a ZOI is observed for M-C12-6.

Figure 14:
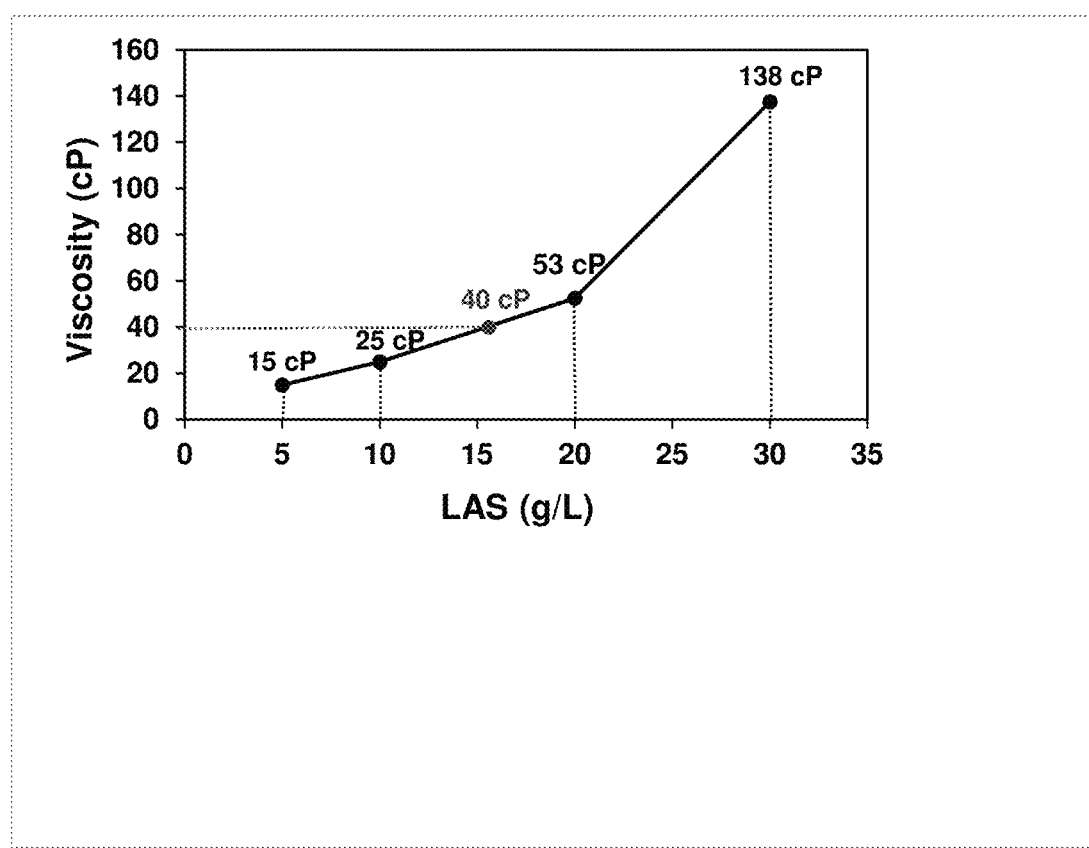

FIG. 14. Laboratory prepared artificial saliva (LAS) viscosity (cP) vs. concentration (g/L). Viscosity was measured at 60 rpm (shear rate, $\gamma=12$ sec$^{-1}$) using an NDJ-1 Rotary Viscometer. The viscosity of 5, 10, 20, and 30 g/L LAS at 37° C. was found as 15, 25, 53, and 138 cP, respectively. The viscosity of commercial artificial saliva CAS (Pickering Laboratory, Inc.) was measured at the same share rate and corresponded to 40 cP (red data point). The viscosity of natural saliva is approximately 5 cP.

Figure 15:
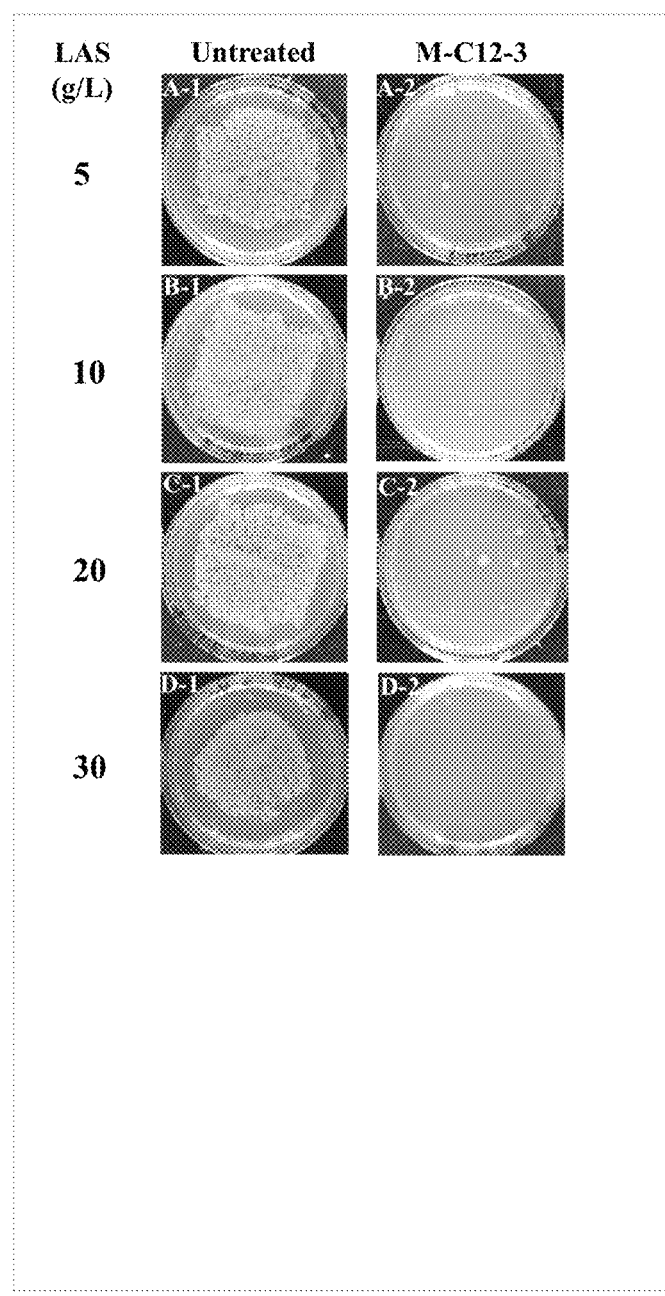

FIG. 15. M-C12-3 effectiveness against a $2.8 \times 10^5$ CFU/ml *Pseudomonas aeruginosa* challenge. Left column, LAS concentration. Middle column, untreated silicone tubes (A-1, B-1, C-1, D-1). Right column, M-C12-3 silicone tubes (A-2, B-2, C-2, D-2). Conclusion: Greater than 99.999% kill in 24 h without influence of viscosity.

Figure 16:
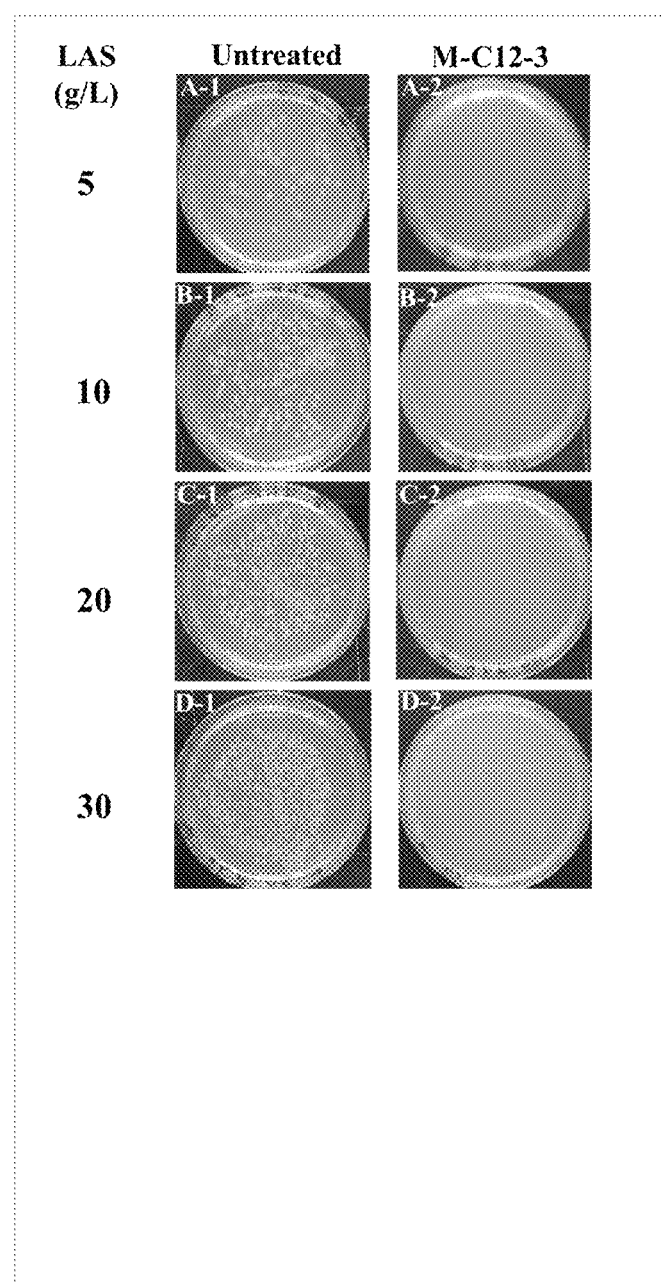

FIG. 16. M-C12-3 effectiveness against a $2.5 \times 10^5$ CFU/ml *Escherichia coli* challenge. Left column, LAS concentration. Middle column, untreated silicone tubes (A-1, B-1, C-1, D-1). Right column, M-C12-3 silicone tubes (A-2, B-2, C-2, D-2). Conclusion: Greater than 99.999% kill in 24 h without influence of viscosity.

Figure 17:
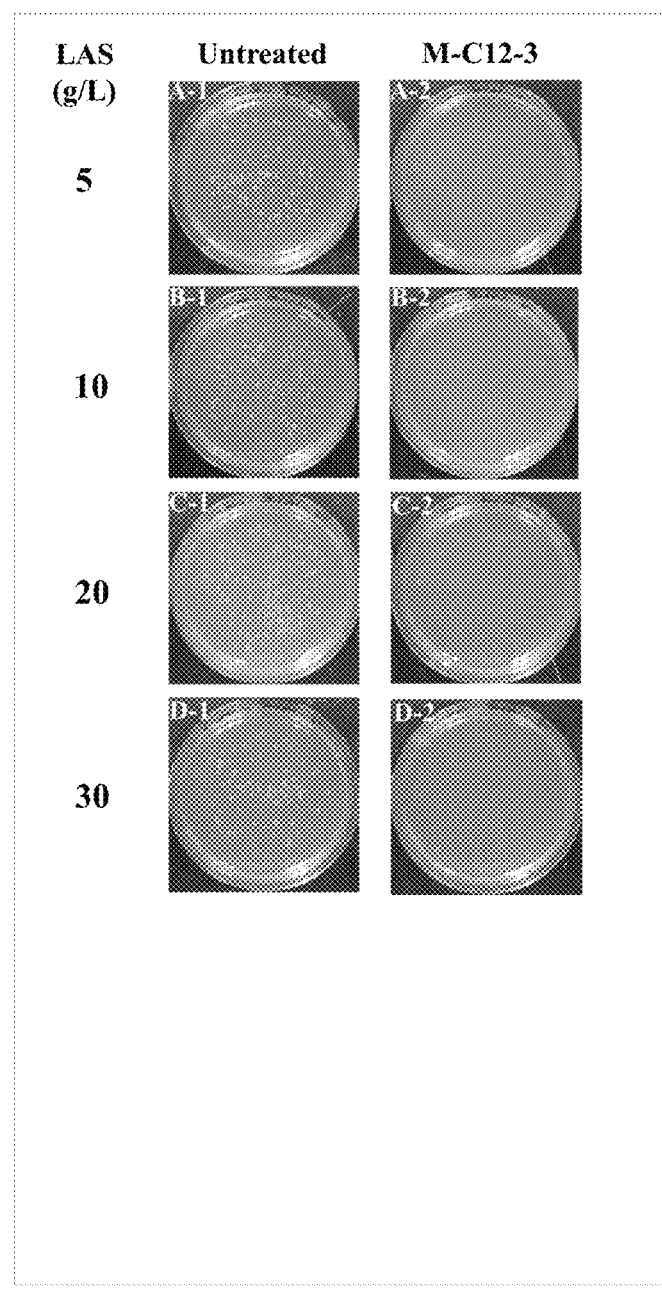

FIG. 17. M-C12-3 effectiveness against a $2.1 \times 10^5$ CFU/ml *Klebsiella aerogenes* challenge. Left column, LAS concentration. Middle column, untreated silicone tubes (A-1, B-1, C-1, D-1). Right column, M-C12-3 silicone tubes (A-2, B-2, C-2, D-2). Conclusion: Greater than 99.999% kill in 24 h without influence of viscosity.

Figure 18:
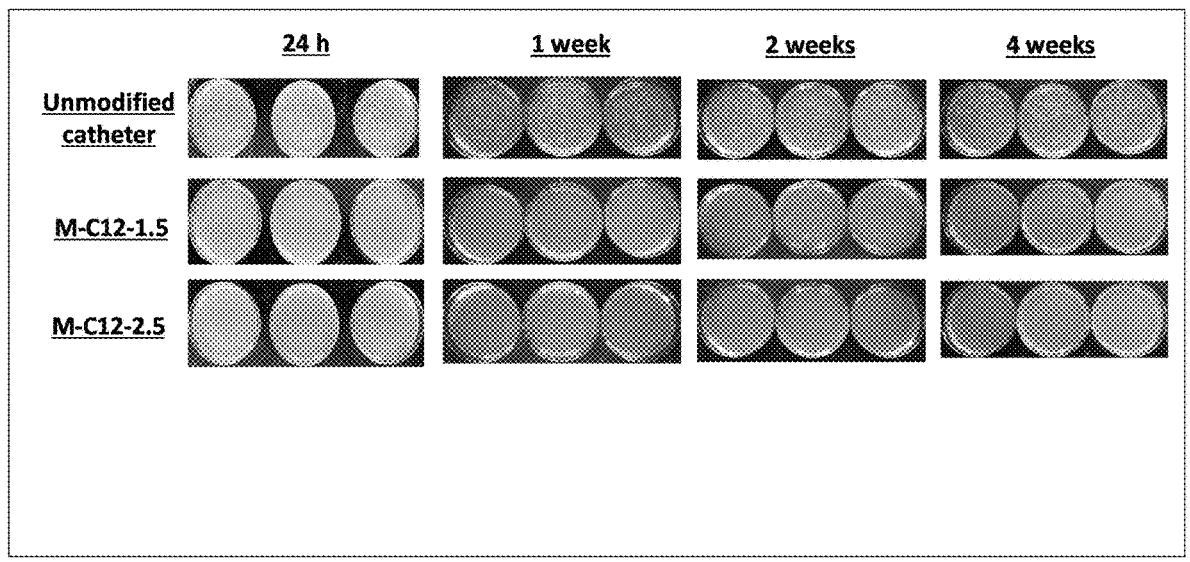

FIG. 18. Unmodified and C12 modified medical grade silicone catheters were immersed in 100 mL of simulated normal urine (SU) at 37° C. with gentle rotation. SU was changed daily. Test samples were then removed at the designated time points and subjected to the shake flask test for evaluation of antimicrobial effectiveness against *E. coli* with initial concentration of $10^5$ cfu/mL.

Figure 19:
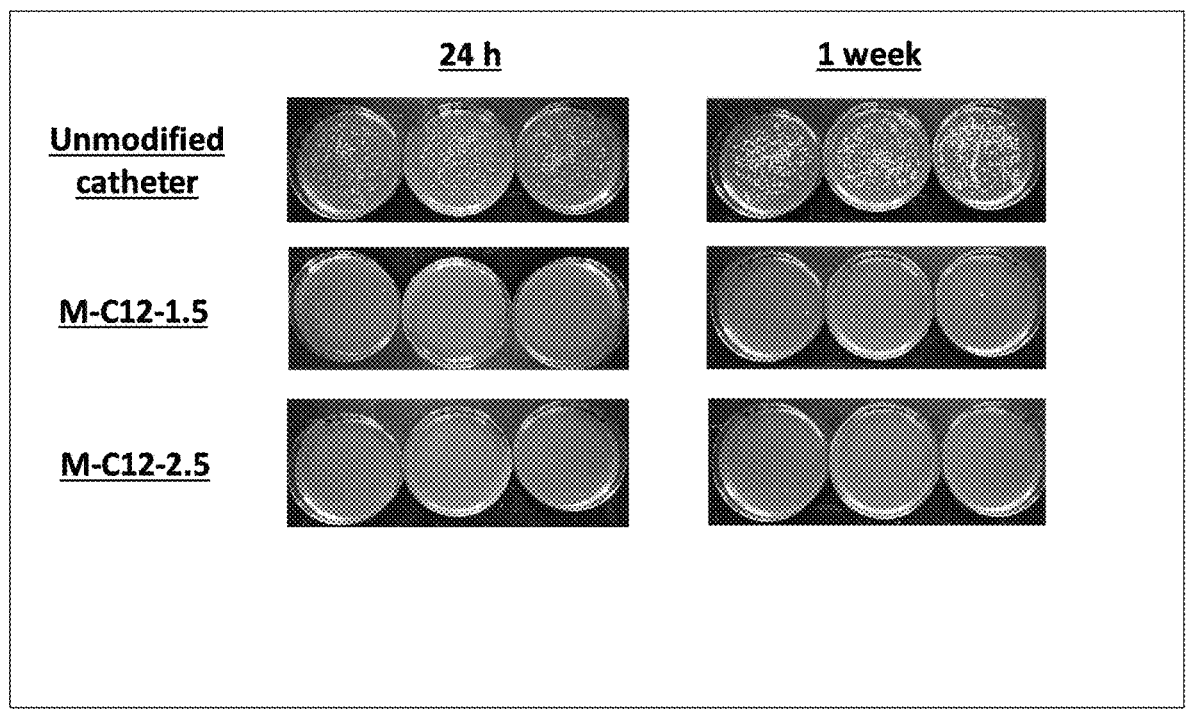

FIG. 19. Unmodified and C12 modified medical grade silicone catheters were immersed in 100 mL of simulated normal urine (SU) at 37° C. with gentle rotation. SU was changed daily. Test samples were then removed at the designated time points and subjected to the shake flask test for evaluation of antimicrobial effectiveness against *Candida albicans* with initial concentration of $10^5$ cfu/mL.

Figure 20:
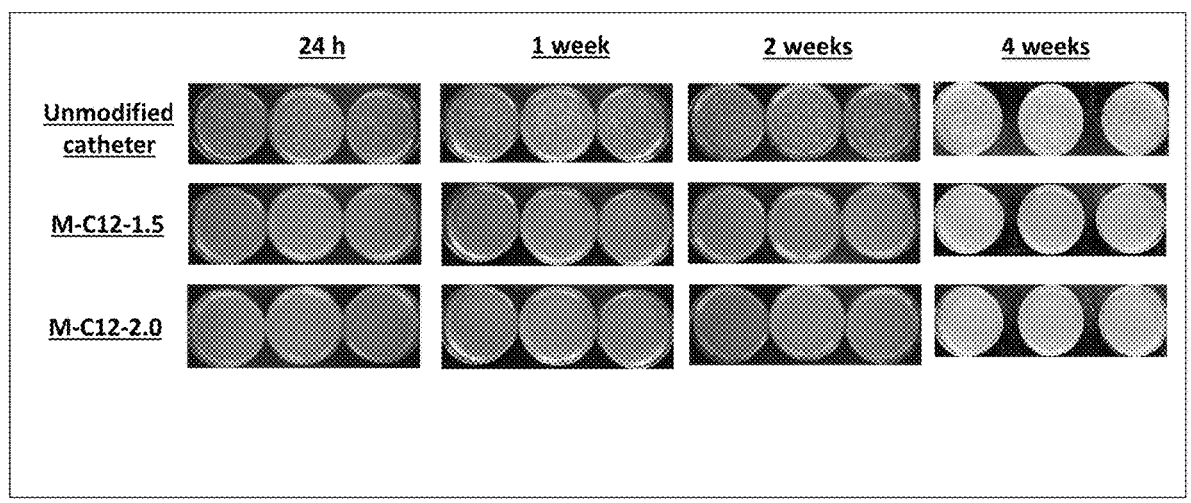

FIG. 20. Unmodified and C12 modified medical grade silicone catheters were kept in a plastic bag at room temperature. At the designated time test the samples were subjected to the shake flask test for evaluation of antimicrobial effectiveness against *E. coli* with initial concentration of $10^5$ cfu/mL.

Figure 21:
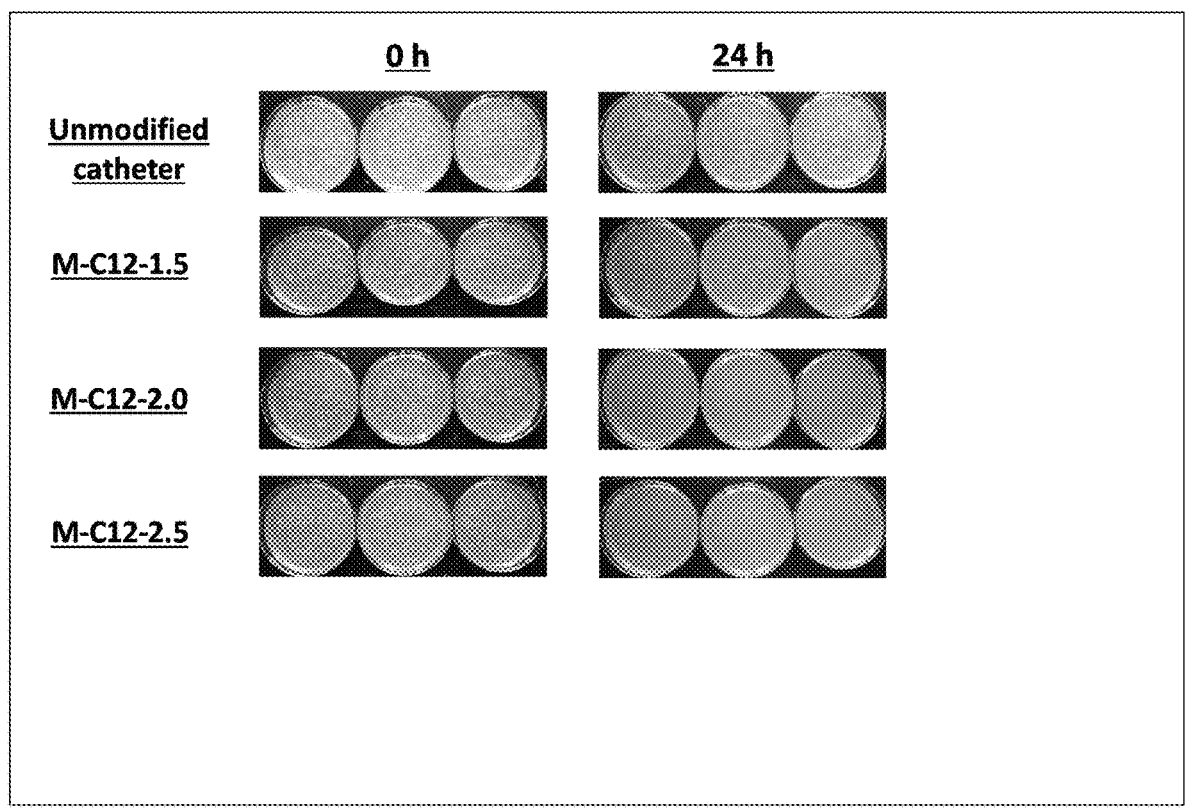

FIG. 21. After cytotoxicity test, C12 modified catheter segments were kept in cell culture medium (FM, Science-Cell catalog #2301) for 3 weeks. Prior to the antimicrobial test, the samples rinsed with DI were immersed in PBS solution and sterilized with UV radiation overnight Test samples were then removed and evaluated for antimicrobial effectiveness against *E. coli* with initial concentration of $2.3 \times 10^5$ cfu/mL.

Figure 22:
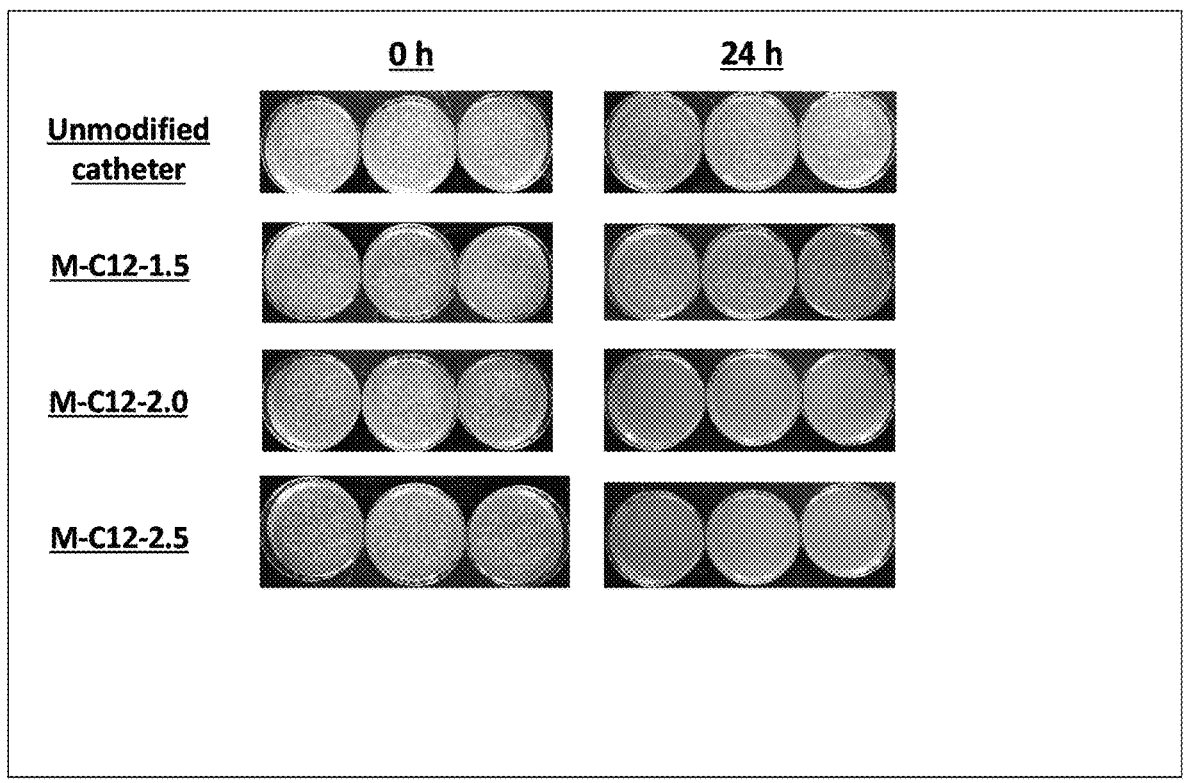

FIG. 22. C12 modified catheter segments tested after evaluation of cytotoxicity conducted at Nelson Labs. Prior to the antimicrobial test, the samples were kept in PBS buffer for 1 month. Test samples were then removed and evaluated for antimicrobial effectiveness against *E. coli* with initial concentration of $2.3 \times 10^5$ cfu/mL.

Figure 23:
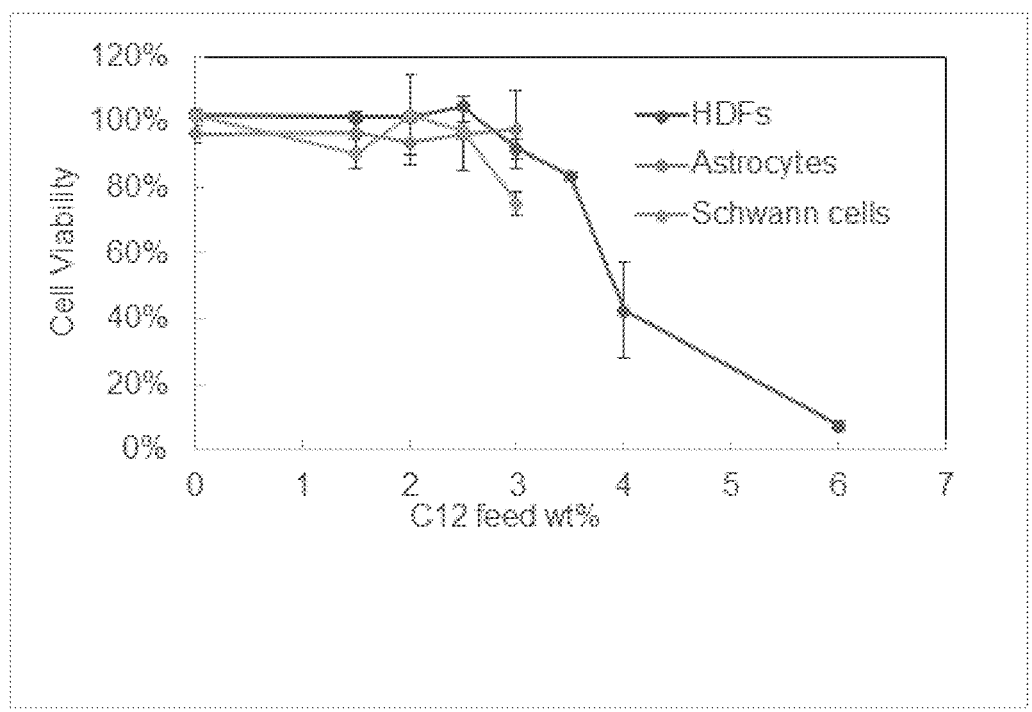

FIG. 23. Viability of HDFs, astrocytes and Schwann cells obtained from ISO 10993-5 Cytotoxicity tests as a function of C12 feed weight percentage.

Figure 24:
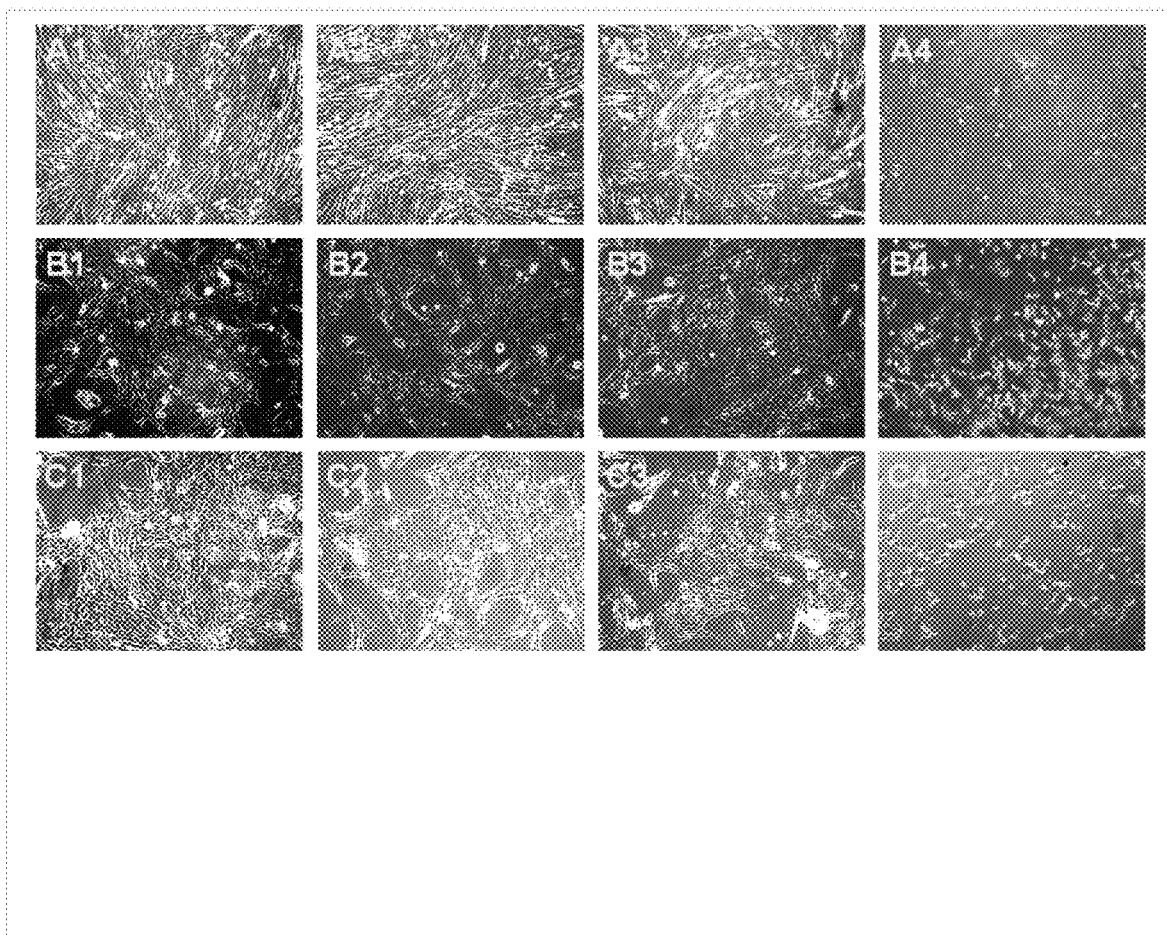

FIG. 24. ISO 10993-5 (extraction) test (48 hours) HDFs in contact with A1, growth medium control; A2, M-C12-1.5 treated silicone extract; A3, M-C12-2 treated silicone extract; A4, latex extract positive control; and Astrocyte cells in contact with B1, growth medium control; B2, M-C12-1.5 treated silicone extract; B3, M-C12-2 treated silicone extract; B4, latex extract positive control; and Schwann cells in contact with C1, growth medium control; C2, M-C12-1.5 treated silicone extract; C3, M-C12-2 treated silicone extract; C4, latex extract positive control.

Figure 25:
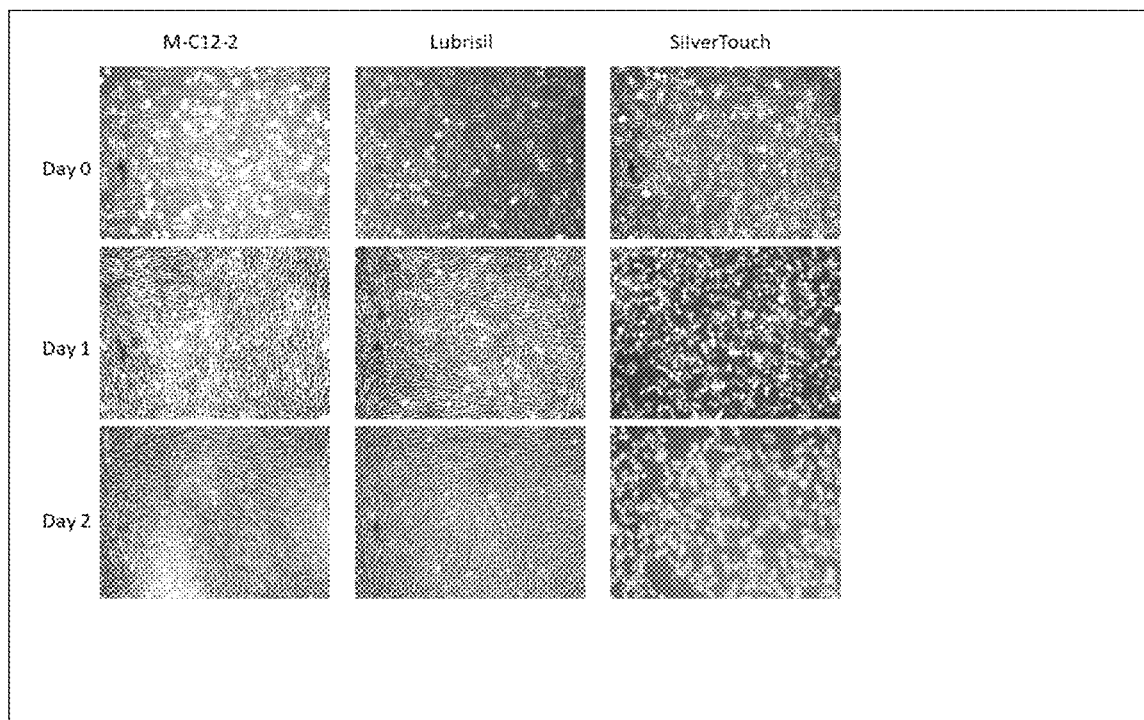

FIG. 25. Comparison of C12-2 with silver-eluting catheters.

Figure 26:
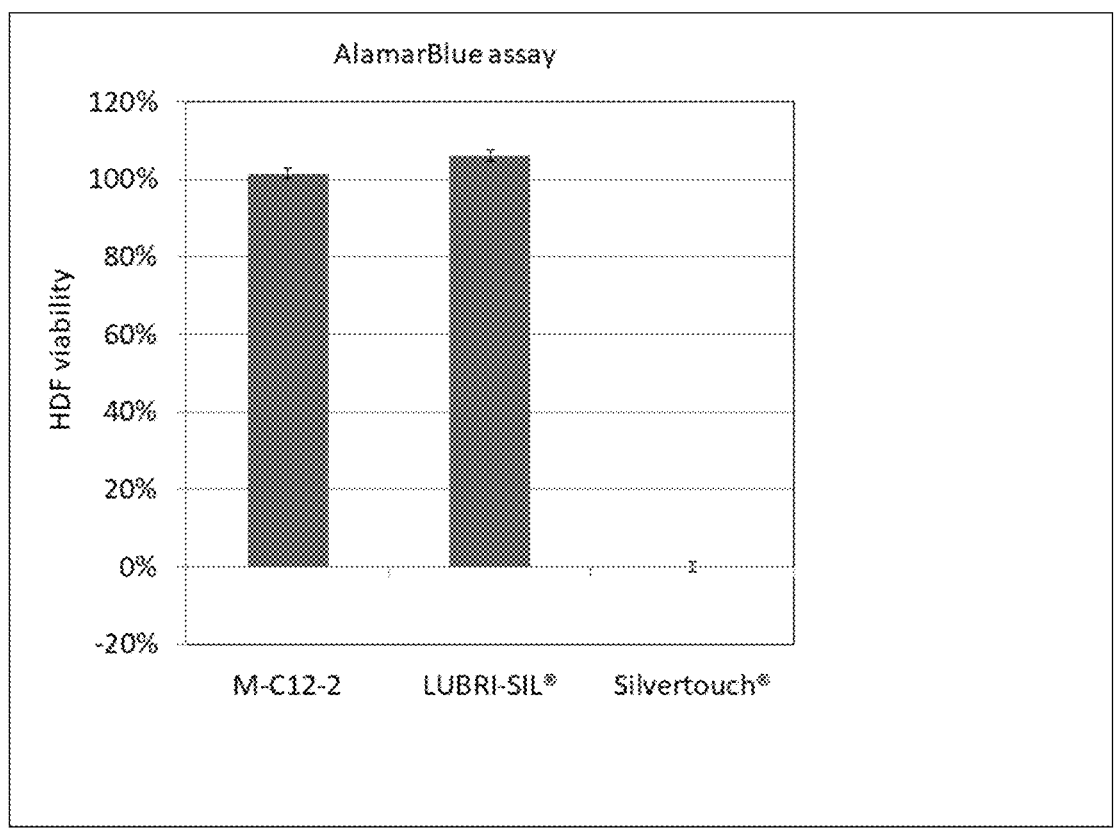

FIG. 26. show a comparison of C12-2 cytocompatibility with two commercially available silver-eluting urinary catheters, Bard Lubrisil and Medline Silver Touch.

Figure 27:
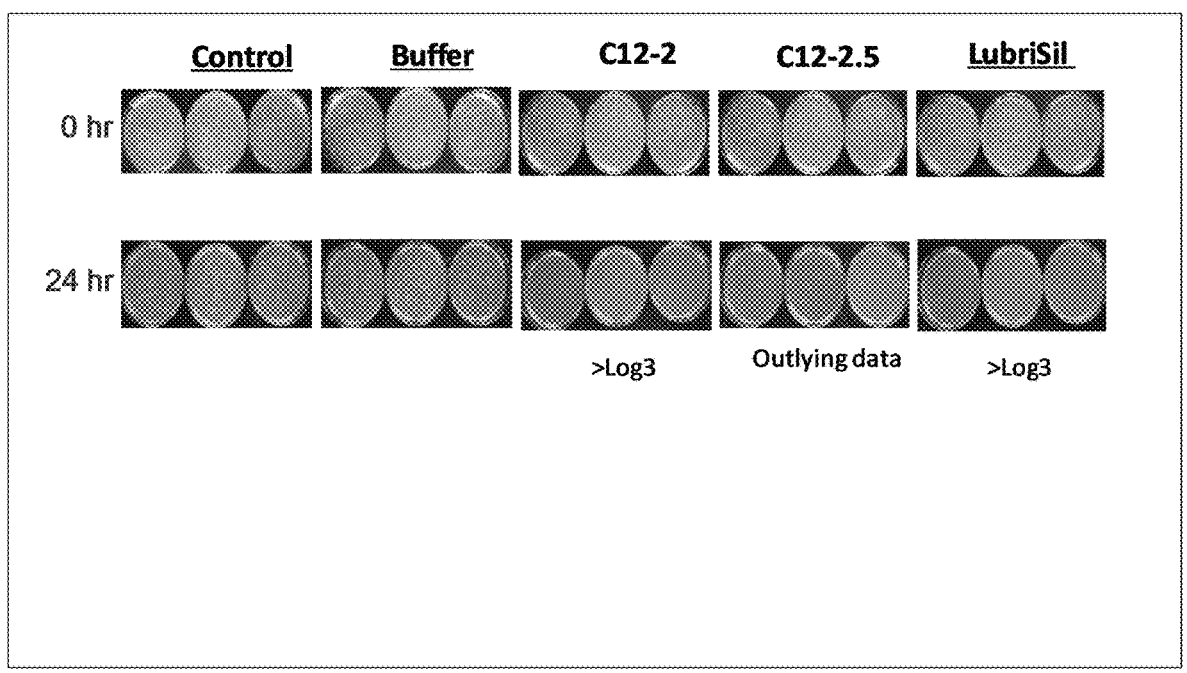

FIG. 27. This slide shows a repeated experiment of an antimicrobial test with LubriSil, C12-2.0 and C12-2.5. (Procedure: ASTM E2149). As prepared samples (0 hr) were compared with samples immersed in simulated urine for 24 hr at 37 C. Results: LubriSil performed similarly to C12-2. The data for C12-2.5 disagree with previous measurements and is considered outlying data. Similar antimicrobial effectiveness was obtained for Medline Silver Touch FIG. 28. A comparison of the product M-C12-2 (WV overcoat) with Bactiseal ventricular drain catheter (impregnated with Rifampin and Clindamycin).

Figure 29:
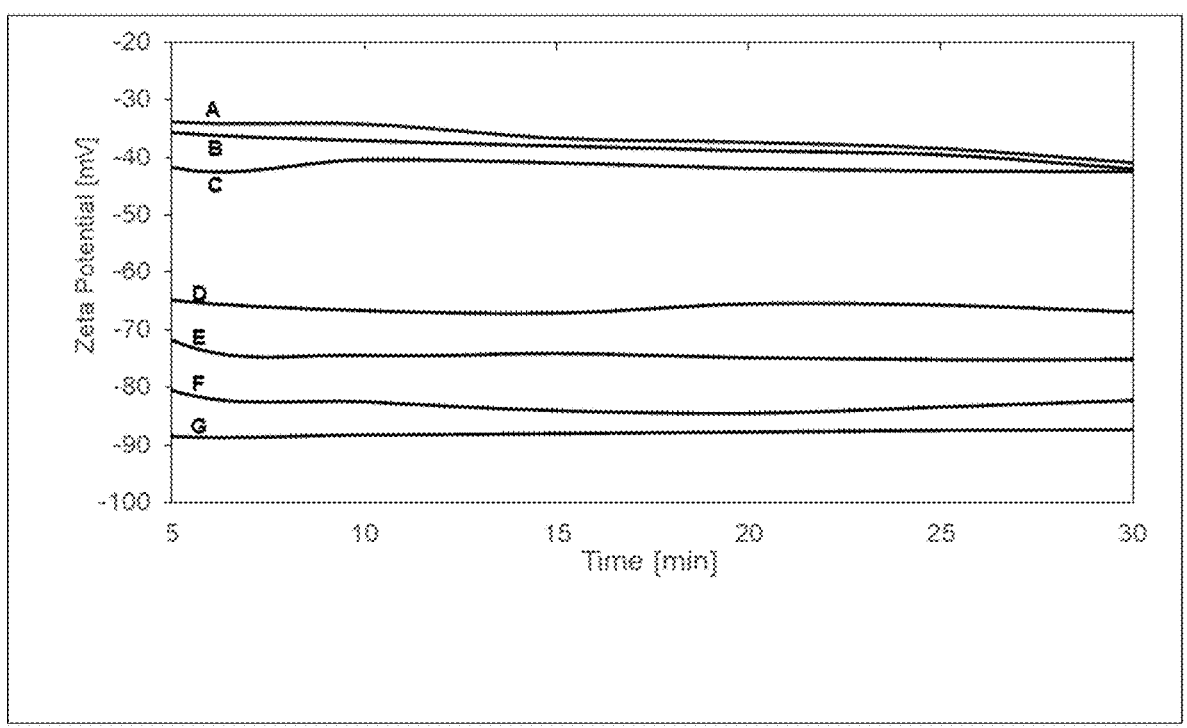

FIG. 29. Zeta Potentials for a model system: Sylgard 184 coatings (100° C. cure, 24 h) treated with C14 (described in Experimental). Measurements for: (A) C14-3, (B) C14-4, (C) C14-5, (D) C14-2, (E) C14-1, (F) C14-0.5, (G) Untreated Sylgard 184 coating.

Figure 30:
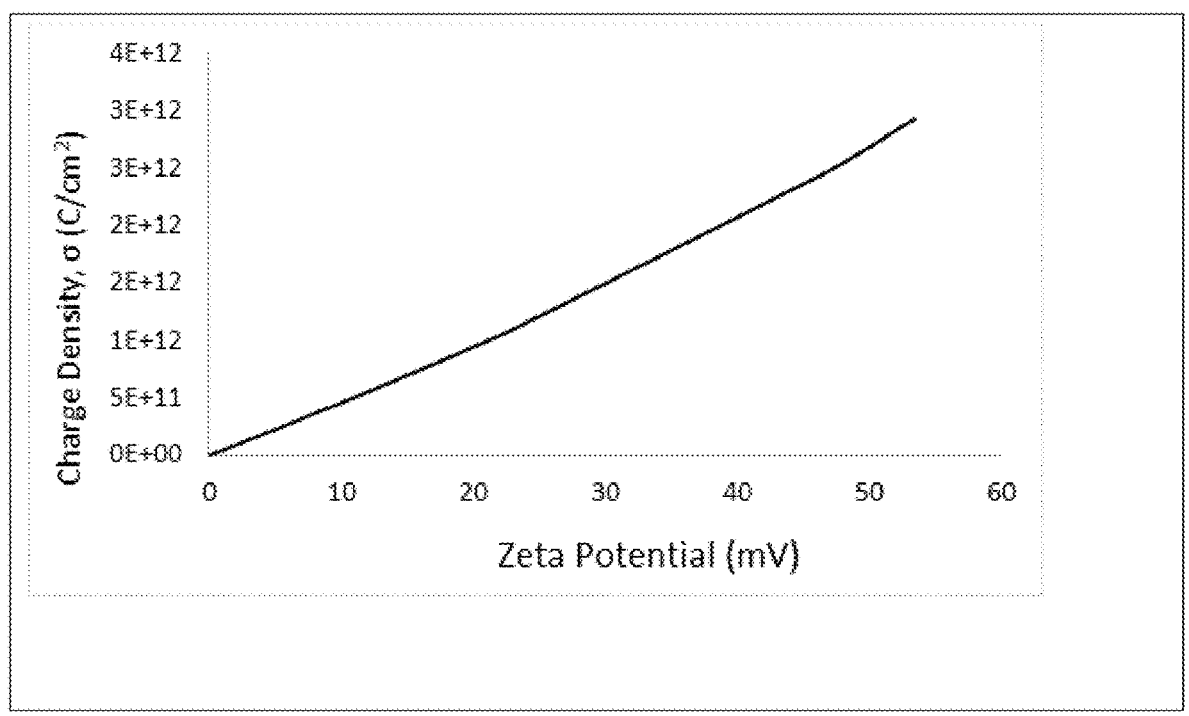

FIG. 30. The relationship of charge density to zeta potential via the Smoluchowski equation (Eq 1).

Figure 31:
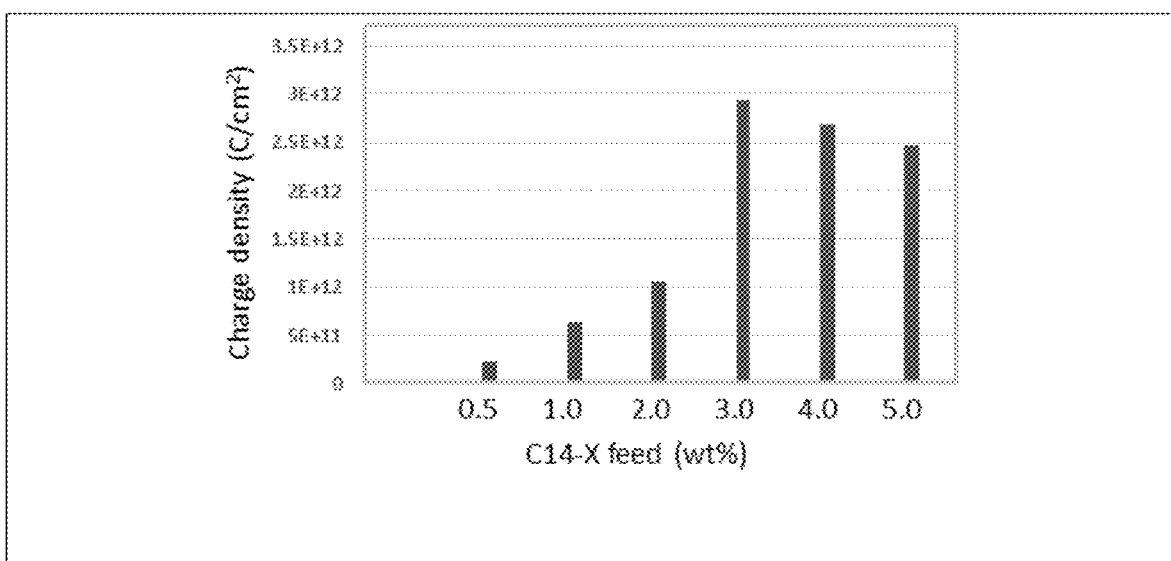

FIG. 31. The relationship of charge density to C14 feed (wt %).

BRIEF SUMMARY OF THE INVENTION

Studying the aforementioned and other needs, the present inventors have developed an innovative technology to address the aforementioned problems, and other problems for silicones, particularly those used in medical devices and/or non-medical surfaces, which might harbor viruses, bacteria, or be subject to biofouling, or physiological contact. Broadly, the present invention provides certain amine—(sometimes referred to herein as tert-N-alkylamine-) treated silicones (sometimes referred to herein as "ABC-silicone" or "WV silicone", in which the silicone surface is treated with the amine, the amine persists on the surface, yet is not covalently or ionically bonded to the silicone surface. The present invention is suitable for all silicone surfaces, but is particularly suited for applications as (1) catheters, endotracheal tubes, ventricular shunts and drains and a wide variety of other medical device applications and (2) other applications.

One embodiment of the present invention provides a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof.

In another embodiment, a medical device is provided, comprising the composition described herein.

In another embodiment, a method is provided for making the composition described herein, comprising:

contacting a polydimethylsiloxane surface with an ethanolic solution of one or more normal $C_6$-$C_{20}NR_1R_2$ saturated amine, salt thereof, or combination thereof;

and drying, to produce the composition.

In another embodiment, a composition is provided, made by a process comprising:

contacting a physiologically-acceptable polydimethylsiloxane surface with an alcoholic solution of one or more normal $C_6$-$C_{20}NR_1R_2$ saturated amine, salt thereof, or combination thereof;

and drying, to produce the composition.

In another embodiment, a medical or other device is provided, having a surface comprised of the composition described herein.

In another embodiment, a method is provided for treating, preventing, or minimizing a risk of an bacterial or viral infection in a subject comprising contacting a subject in need of infection treatment or prevention or minimization of risk with the composition described herein.

In another embodiment, an antimicrobial, cytocompatible or antiviral surface is provided, comprised of the composition described herein.

In another embodiment, a cytocompatible surface is provided, comprised of the composition described herein.

In another embodiment, a method is provided of killing or reducing a population of bacteria or virus, or reducing the growth rate of a population of bacteria or virus, comprising contacting the bacteria or virus population with the composition described herein.

DETAILED DESCRIPTION

One aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof.

An aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, wherein the amine is not covalently bonded to the polydimethylsiloxane or surface either directly or through a linker.

An aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, wherein the amine is not ionically bonded to the polydimethylsiloxane or surface either directly or through a linker.

An aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, wherein the composition is antimicrobial, cytocompatible, antiviral, or combination thereof.

An aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, wherein the composition is antimicrobial and cytocompatible.

An aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, wherein the composition is antimicrobial to G+ bacteria, G− bacteria, or both.

An aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, wherein the composition is stable under ambient conditions.

An aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —CH$_3$, —CH$_2$CH$_3$, —CH$_2$CH$_2$CH$_3$, or combination thereof, wherein the composition is stable in air, water, saline, physiological fluid, urine, blood, saliva, mucosa, plasma, cerebrospinal fluid, nasolacrimal fluid, tissue, or combination thereof.

An aspect of the present invention relates to a composition, comprising:

a physiologically-acceptable polydimethylsiloxane having a surface; and one or more normal C$_6$-C$_{20}$NR$_1$R$_2$ saturated amine, salt thereof, or combination thereof, in contact with the polydimethylsiloxane, the surface, or both, wherein R$_1$ and R$_2$ may be same or different and independently selected from H, —CH$_3$, —CH$_2$CH$_3$, —CH$_2$CH$_2$CH$_3$, or combination thereof, wherein the C$_6$-C$_{20}$NR$_1$R$_2$ amine is a 6, 8, 10, 12, 14, 16, 18 or 20 carbon chain amine.

An aspect of the present invention relates to a composition, comprising:

a physiologically-acceptable polydimethylsiloxane having a surface; and one or more normal C$_6$-C$_{20}$NR$_1$R$_2$ saturated amine, salt thereof, or combination thereof, in contact with the polydimethylsiloxane, the surface, or both, wherein R$_1$ and R$_2$ may be same or different and independently selected from H, —CH$_3$, —CH$_2$CH$_3$, —CH$_2$CH$_2$CH$_3$, or combination thereof, wherein C$_6$-C$_{20}$NR$_1$R$_2$ amine is a 10, 12, 14, or 16 carbon chain amine.

An aspect of the present invention relates to a composition, comprising:

a physiologically-acceptable polydimethylsiloxane having a surface; and one or more normal C$_6$-C$_{20}$NR$_1$R$_2$ saturated amine, salt thereof, or combination thereof, in contact with the polydimethylsiloxane, the surface, or both, wherein R$_1$ and R$_2$ may be same or different and independently selected from H, —CH$_3$, —CH$_2$CH$_3$, —CH$_2$CH$_2$CH$_3$, or combination thereof, wherein R$_1$ and R$_2$ are both H.

An aspect of the present invention relates to a composition, comprising:

a physiologically-acceptable polydimethylsiloxane having a surface; and one or more normal C$_6$-C$_{20}$NR$_1$R$_2$ saturated amine, salt thereof, or combination thereof, in contact with the polydimethylsiloxane, the surface, or both, wherein R$_1$ and R$_2$ may be same or different and independently selected from H, —CH$_3$, —CH$_2$CH$_3$, —CH$_2$CH$_2$CH$_3$, or combination thereof, wherein R$_1$ and R$_2$ are both —CH$_3$.

An aspect of the present invention relates to a composition, comprising:

a physiologically-acceptable polydimethylsiloxane having a surface; and one or more normal C$_6$-C$_{20}$NR$_1$R$_2$ saturated amine, salt thereof, or combination thereof, in contact with the polydimethylsiloxane, the surface, or both, wherein R$_1$ and R$_2$ may be same or different and independently selected from H, —CH$_3$, —CH$_2$CH$_3$, —CH$_2$CH$_2$CH$_3$, or combination thereof, wherein the amine is a quaternary amine.

In the process of making, the silicone is not contacted with a quaternary amine, but rather the amine. However, upon exposure of the treated silicone surface to water, other liquid, or physiological liquid, a quaternized amine surface may result. If quaternized, the counterion—the anion—is not particularly limited, and may include any physiological acceptable anion, including chloride, bromide, iodide, sulfate, carbonate, hydrogen carbonate, or the like. It is contemplated that the absorption of CO$_2$ in a liquid medium in contact with the treated silicone will give rise to HCO$_3^-$ and/or CO$_3^{2-}$ in solution, which may act as counterion.

In a modeling calculation, assuming 1.54 Å C—C bond length and 109° C.—C bond angle (sp$^3$ hybridized atoms), the length of a C-12 molecule is calculated as 1.63 nm and width is calculated as 0.09 nm. The —N(CH$_3$)$_2$ end group is not considered in this calculation to simplify the model. Thus, each C12 molecule in lying position occupies about 0.15 nm$^2$. The calculated surface C12 density for maximum packing in lying position is 6.7×10$^{14}$ C12/cm$^2$.

Thus, the calculated C12 mass per unit surface area is 2.4×10$^{-4}$ mg/cm$^2$. This calculated C12 surface density is ~1000 times lower than the results obtained via titration or NMR methods (0.25 mg/cm$^2$ for M-C12-1, 0.46 mg/cm$^2$ for M-C12-2, 0.80 mg/cm$^2$ for M-C12-3, 1.14 mg/cm$^2$ for M-C12-4).

Similarly, assuming maximum packing in standing position, the calculated surface C12 density is 4.4×10$^{16}$ C12/cm$^2$. So, the calculated C12 mass per unit area is 1.5×10$^{-2}$ mg/cm$^2$, which is ~17 to 76 times lower than the results obtained via titration or NMR methods (0.25 mg/cm$^2$ for M-C12-1, 0.46 mg/cm$^2$ for M-C12-2, 0.80 mg/cm$^2$ for M-C12-3, 1.14 mg/cm$^2$ for M-C12-4).

Without wishing to be bound by theory, this result suggests that C12 molecule is not absorbed on silicone surface in the form of single molecular layer.

As will be shown below, the experiment (NMR) wt % of the C12 amine on the treated silicone is ~1000 times higher than the calculated wt % assuming the C12 amine molecule lay on the surface horizontally. The experiment wt % is 17 to 76 times, depending on feed concentration, higher than the calculated wt % assuming the C12 amine molecule stand on the surface vertically.

Without wishing to be bound by theory, it is believed that a portion of or substantially all of the amine molecules are diffused at least in part into the silicone surface. In another embodiment, all or a portion of the amine molecules may remain on the surface in one or more layers. In another embodiment, a portion of the amine molecules may remain on the surface and another portion may be diffused into the silicone. In either case, it is believed that the amine molecules are not bound to the silicone via covalent bond or ionic bond.

The surface concentration of amine, whether on or diffused into the silicone surface, or both, in mg amine/cm$^2$ of silicone surface is not particularly limited. For example, the surface concentration of amine may range from 0.01 to 2 mg/cm$^2$. This range, or any subrange thereof may include 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, and 2 mg/cm$^2$, any subrange therein, or any combination thereof. For example, in embodiments, the surface concentration of amine may be 0.1 to 0.9 mg/cm$^2$ Suitable amines include normal C$_6$-C$_{20}$NR$_1$R$_2$ saturated amines, wherein R$_1$ and R$_2$ may be same or different and independently selected from H, —CH$_3$, —CH$_2$CH$_3$, —CH$_2$CH$_2$CH$_3$, or combination thereof. This includes amines with 6, 7, 8, 9, 10, 11, 12, 13, 14, 15, 16, 17, 18, 19 and 20 carbon chains.

One type of amine may be used, but mixtures of one or more different amines are also possible. For example, a mixture of two or more C12, C14, C16, C18, or C20 amines is possible.

In embodiments, the amine does not include an aromatic group. In embodiments, the amine does not include a cyclic group. In embodiments, the amine does not include n-alkyl dimethyl benzyl amine or ammonium chloride, n-alkyl ethylbenzyl amine or ammonium chloride, dimethyl dioctyl amine, ammonium chloride, benzalkylamine or benzylalkonium chloride, Microban® products or additives, octyl decyl dimethyl amine or ammonium chloride, dioctyl dimethyl amine or ammonium chloride, or didecyl amine or ammonium chloride.

The amount of tert-N-alkylamine is not particularly limiting, and any amount may be suitably used. In one aspect, the tert-N-alkylamine is present in an amount of about 1% by weight or less, based on the weight of the treated silicone. This range includes all values and subranges therebetween, including about 1, 0.9, 0.8, 0.7, 0.6, 0.5, 0.4, 0.3, 0.2, 0.1, % by weight, and less so long as it is greater than zero.

The tert-N-alkylamine concentration at the surface and the near-surface may be easily tuned to optimize the antimicrobial, antiviral and/or antimicrobial compatible properties of the silicone.

In the case of a catheter, or any device, different parts of the catheter or device can be processed differently, to similarly optimize the antimicrobial and set of compatible properties, and/or physical properties of the catheter or device. The process is simple, controllable, repeatable, and robust.

Without wishing to be bound by theory, in contrast to silver-eluting or antibiotic-eluting antimicrobial catheters, the antimicrobial action of the subject device is not believed to be dependent on leachates or eluted compounds. Rather, and without wishing to be bound by theory, it is believed that the mechanism of action of the subject device relies on physical contact kill.

An aspect of the present invention relates to a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, wherein the polydimethylsiloxane or surface is not oxidized, plasma-treated, corona-treated, flame-treated, or otherwise chemically or physico-chemically modified.

The silicone elastomer is not particularly limited. Preferably, the silicone contains only the amine and does not contain other additive or medicaments, and is physiologically acceptable. Given the teachings herein, combined with the skill of an ordinary medicinal silicone chemist, one can easily determine what is meant by physiologically acceptable. In other embodiments, silicones loaded with silver, antibiotic, antioxidant, UV-inhibitor, or other medicament is possible. One example of physiologically acceptable silicones include those sold by Bard or Bardex. Another example includes Silastic® silicones sold by Dow, Inc., and Silastic MDX4-4210. Preferably, commercial non-food grade or non-medical silicones are not used. For example, Sylgard® 184 silicone elastomer sold by Dow Corning is not preferred as a silicone.

The treated silicone is desirably produced by contacting the silicone with an ethanolic solution of the amine at a concentration and for a time and temperature to produce the intended effect.

In one embodiment, the silicone is not contacted with neat amine. In one embodiment, the alcohol solution is an ethanolic solution contains only or substantially only ethanol, water, and the intended amine, and does not contain or substantially does not contain other constituents.

An aspect of the present invention relates to a medical device, comprising a composition, comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof.

An aspect of the present invention relates to a method making a composition, the composition comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, the method comprising:

contacting a polydimethylsiloxane surface with an ethanolic solution of one or more normal $C_6$-$C_{20}NR_1R_2$ saturated amine, salt thereof, or combination thereof;

and drying, to produce the composition.

An aspect of the present invention relates to a composition made by a process, the composition comprising:

a physiologically-acceptable polydimethylsiloxane having a surface; and one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof, the process comprising:

contacting a physiologically-acceptable polydimethylsiloxane surface with an alcoholic solution of one or more normal $C_6$-$C_{20}NR_1R_2$ saturated amine, salt thereof, or combination thereof; and drying, to produce the composition.

In an aspect of the composition or method described herein, the contacting comprises one or more of dipping, spraying, soaking, or a combination thereof of said polydimethylsiloxane surface in or with the alcoholic solution.

The alcoholic solution is not particularly limiting and may be any of Ethanol, Methanol, i-Propanol and Butanol. In one embodiment, an ethanolic solution is used. In one embodiment, the ethanol solution is an aqueous solution of 90% or greater ethanol, which includes 95, 97, 98, 99, 99.9% ethanol or greater.

In one embodiment, the physiologically-acceptable polydimethylsiloxane surface is contacted with the alcoholic solution of amine at a temperature of 20 to 60° C., which includes fall values and subranges therebetween, including 20, 25, 30, 35, 40, 45, 50, 55 and 60° C. In one embodiment, a temperature of 40° C. is used.

The time of contacting is not particularly limiting, and may suitably be from 10 minutes to overnight, which range includes all values and subranges therebetween, including 10, 20, 30, 40, 50, 60, minutes, 1, 2, 3, 4, 6, 8, 10 and 24 hours, or any combination thereof. In one embodiment, the contacting is carried out by immersion with stirring for 1 hour.

The amount of amine in the alcoholic solution is not particularly limited, and may suitably range from 0.5 to 20% by weight amine to weight of solvent, which range includes all values and subranges therebetween, including 0.5, 0.6, 0.7, 0.8, 0.9, 1, 2, 3, 4, 5, 6, 7, 8, 9, 10, 12, 15 and 20% by weight. In one embodiment, 0.9 to 5% by weight of amine may be used.

Preferably, the treated silicone does not leach the amine into the surrounding medium.

In an aspect of the composition or method described herein, the amine, salt thereof, or combination thereof is in the form of one or more of a monolayer or multilayer on the surface, is dispersed or absorbed in the polydimethylsiloxane, is dispersed or absorbed in a near-surface portion of the polydimethylsiloxane, or combination thereof.

The terms, silicone and polydimethylsiloxane are used interchangeably herein.

In an aspect of the composition or method described herein, the polydimethylsiloxane is not completely swollen by the amine. In one embodiment, the silicone is only partially swollen by the amine, or swollen in only the surface or near-surface region of the silicone.

In an aspect of the composition or method described herein, the amine may be separated from the polydimethylsiloxane, surface, or combination thereof by exposure to vacuum, organic solvent, acid, base, or combination thereof.

In an aspect of the composition or method described herein, the composition is stable to radiative sterilization.

An aspect of the present invention relates to a medical or other device, having a surface comprised of the composition described herein.

An aspect of the present invention relates to a method for treating, preventing, or minimizing a risk of an bacterial or viral infection in a subject comprising contacting a subject in need of infection treatment or prevention or minimization of risk with the composition described herein.

An aspect of the present invention relates to an antimicrobial, cytocompatible or antiviral surface, comprising the composition described herein.

An aspect of the present invention relates to a cytocompatible surface is provided, comprising the composition described herein.

An aspect of the present invention relates to a method for killing or reducing a population of bacteria or virus, or reducing the growth rate of a population of bacteria or virus, comprising contacting the bacteria or virus population with the composition described herein.

In an aspect of the composition or method described herein, the polydimethylsiloxane or surface is suitable for physiological contact or medical use.

In an aspect of the composition or method described herein, the composition is antiviral and cytocompatible.

In an aspect of the composition or method described herein, the composition is antiviral to human viruses, pathogenic or non-pathogenic viruses, coronaviruses, COVID-19, DNA viruses, ds DNA viruses, ss DNA viruses, RT viruses, reverse transcribing viruses, RNA viruses, dsRNA viruses, ss RNA (+) viruses, ss RNA (−) viruses, circular ss RNA viruses, viroids, or combinations thereof.

An aspect of the present invention relates to a method for treating or preventing a viral infection in a subject comprising contacting a subject in need of viral infection treatment or prevention with the composition described herein.

An aspect of the present invention relates to an antiviral surface, comprising the composition described herein.

An aspect of the present invention relates to a cytocompatible surface, comprising the composition described herein.

An aspect of the present invention relates to a method of killing or reducing a population of virus, or reducing the growth rate of a population of virus, or reducing the transmission of a virus, comprising contacting the virus population with the composition described herein.

Without wishing to be bound by theory, in contrast to silver-eluting or antibiotic-eluting antimicrobial catheters, the antimicrobial action of the subject device is not believed to be dependent on leachates or eluted compounds. Rather, and without wishing to be bound by theory, it is believed that the mechanism of action of the subject device relies on physical contact kill.

One embodiment of the process to produce the device involves immersing a conventional, uncoated silicone catheter in a 95% ethanolic solution of known tert-N-alkylamine under controlled conditions of temperature, time, and amine concentration. In one aspect, the amine is N,N-dimethyltetradecylamine ($CH_3(CH_2)_{13}N(CH_3)_2$, CAS No. 112-75-4). The process results in a stable, silicone-alkylamine phase at the catheter surface. The term, "silicone-alkylamine phase" is meant to convey results that indicate the two components (silicone, amine) are not covalently bonded, yet act as one at the catheter surface. The tert-N-alkylamine is soluble in the silicone. The silicone-alkylamine phase is optically transparent, i.e., there is no phase separation between the silicone and alkylamine. The tert-N-alkylamine is insoluble in water and physiological media. The tert-N-alkylamine does not leach out or elute into water or physiological media.

Still further, different parts of the catheter can be processed differently, to similarly optimize the antimicrobial and set of compatible properties, and/or physical properties of the catheter or different parts of the catheter. The process is simple, controllable, repeatable, and robust.

Through extensive testing, the treated silicone surface that results from the process is observed to be both antimicrobial and cytocompatible, and thus is designated "ABC-Silicone". The ABC-Silicone: (1) achieves a 3-5 log reduction (99.9-99.999% kill) of common pathogens associated with urinary tract infections, including *Escherichia coli, Candida albicans* and *Klebsiella pneumoniae*, (2) achieves pathogen kill without detectable leaching or elution of tert-N-alkylamine into the surrounding medium, (3) achieves in vitro and in vivo bio- and cytocompatibility, (4) is stable to immersion in simulated urine over a physiological pH range of 4-8, (5) is stable as packaged in a nitrogen atmosphere, and (6) is stable to sterilization by gamma irradiation. In tests on the one embodiment of the corresponding silicone Foley catheter, deflation of the catheter balloon resulted in deflated balloon dimensions within an acceptable range.

Any silicone surface can be successfully treated with the process. As such, it is believed that there are no limits on size and/or dimensions of the device.

For catheter testing, segments of a commercially available uncoated silicone catheter (Bardex® All-Silicone Foley Catheter, an uncoated silicone catheter without antimicrobial properties, Fr 22) was subjected to the process (sometimes referred to herein for convenience only as, "ABC-Silicone process") to produce silicone catheter segments The appearance of the catheter is unchanged after the ABC-Silicone process. A mass change of about 1 wt %, based on the weight of the treated catheter segments, was observed.

In vitro and in vivo studies have been carried out, which support the inventors' belief that the modified surface achieves its antimicrobial properties through physical contact kill. There is general agreement that contact of bacteria with a surface having a net positive charge is key to physical contact kill of bacteria, perhaps via disruption of the negatively charged bacterial membrane. Thus, without wishing to be bound by theory, it is believed that charge generation at the ABC-Silicone surface disrupts negatively-charged bacterial membranes upon contact. This hypothesis is supported by the $pK_a$ of tert-N-alkylamines, which is about 10. As such, in water and physiological media, tert-N-alkylaminesare readily quaternized to form a trialkylammonium moiety, $R_3NH^+$, where R is an alkyl group. Both the tert-N-alkylamine and the corresponding quaternized trialkylammonium moiety, $R_3NH^+$, are at least partially soluble in the silicone and are insoluble in water and physiological media. It is believed that, upon quaternization, the stable, silicone-alkylamine phase of the ABC-Silicone surface presents a net positive surface charge to the surrounding medium.

Disrupting bacterial membranes, i.e. killing bacteria on contact, tends to prevent bacterial adhesion to the catheter surface. Proliferation of bacteria is inhibited, which is believed to result in a decreased tendency to form biofilms.

The silicone catheter is indicated for use in bladder management including continuous urine drainage, collection and measurement for patients requiring catheterization for surgical procedures, monitoring urine output, management of incontinence and for voiding dysfunction.

Examples of conventional, comparative devices include (1) Bardex® Lubri-Sil® I.C. Foley Catheter, an antimicrobial all-silicone Foley catheter containing a silver antimicrobial moiety, and (2) Bardex® All-Silicone Foley Catheter, an uncoated silicone catheter without antimicrobial properties.

The Bardex® All-Silicone Foley Catheter (2) was subjected to the process, to form the ABC-Silicone surface for testing as an exemplary embodiment. Comparative performance testing was conducted against as-purchased, untreated (2) Bardex® All-Silicone Foley Catheter.

The process is applicable to any type of silicone surface or device. In one embodiment, the process is applicable to any brand or model of silicone urinary catheter. In comparative performance testing, it was found that the subject surface modification process does not adversely affect performance of the unmodified silicone catheter.

Comparative Bardex® Lubri-Sil® I.C. Foley Catheter, an antimicrobial all-silicone Foley catheter containing a silver antimicrobial moiety achieves its antimicrobial properties by leaching silver from the surface; the subject device is believed to achieve antimicrobial properties through physical contact kill.

The silicone catheter is expected to provide equivalent or increased benefit and equivalent or decreased risk compared to the conventional devices. Preliminary, non-clinical studies have been conducted on embodiments of the catheter that demonstrate a physical contact kill mechanism without leaching while ensuring biocompatibility and suitable device performance. The subject device is non-cytotoxic, does not leach or elute antimicrobial species, and its antimicrobial effectiveness is at least equivalent to the predicate device. In vivo and in vitro biocompatibility tests have also been performed and support biological safety of the subject device.

Some non-limiting applications of the treated silicones include: Silicone urinary catheters; Foley Catheters; urinary catheters, Silicone Coated Latex 2-Way Urinary Cath; hypoallergenic sheets for wound care; ureteral stents; ventricular shunts and drains, lacrimal stent, Jones tube, Silicone Nichols Dilators; Defibrillators; heart pumps; surgical reconstructive components; diaphragms for respiratory equipment; lip seals for cylinder applications; isolation bumpers used to inhibit vibrations; mammary shells; balloons; durable coated surfaces; coated surgical blades; non-slip handles on surgical tools; elastomeric sheets; wipes; filters; valve assemblies; mesh-reinforced sheeting that is integrated as sewing rings on artificial heart valves; laminated sheeting containing both vulcanized and un-vulcanized layers used to produce seal tissue expanders and mammary devices; punctual plugs; small joint implants; airways; balloon catheters; tubing for feeding, drainage, and use with peristaltic pumps; compression bars; electrosurgical handpieces; infusion sleeves and test chambers; introducer tips and flexible sheaths; wire/fluid-path coextrusions; ear plugs and hearing; face implants, nasolacrimal stent, to name a few.

Other examples of applications include any surface that is suitable for contact by a human, or that might harbor a virus, surfaces, commercial surfaces, counters, desks, chairs, masks, fabric, clothing, cloth, personal hygiene items, tables, doorknobs, filters, HEPA filters, HVAC equipment, ducting, vents, ventilators, gloves, protective shields, food contact surfaces, food preparation surfaces, food display surfaces, light switch plates, diagnostic surfaces, well plates, and the like. Still other examples of applications include Covers for elevator buttons reading glasses, Text book covers, strollers, shopping carts, door handles, TV or gaming controllers, DVD covers, arm rests, covers for high contact surfaces (tables, chairs, desks, etc.), keyboard covers, cell phone cases, screen protective membranes, door knob covers, insole/footbed, gloves, water pipeline, water storage containers/tanks, water purification filters, toilet floor mats, and toilet seat covers.

The materials described herein are considered to be effective against human viral pathogens, for example pathogenic or non-pathogenic viruses, coronaviruses, COVID-19, DNA viruses, ds DNA viruses, ss DNA viruses, RT viruses, reverse transcribing viruses, RNA viruses, dsRNA viruses, ss RNA (+) viruses, ss RNA (−) viruses, circular ss RNA viruses, viroids, and the like. Other viruses against which the present invention may be effective include Herpesviridae, Simplexvirus, Varicellovirus, Cytomegalovirus, Roseolovirus, Lympho-cryptovirus, Rhadinovirus; Adenoviridae, Mastadenovirus; Papillomaviridae, Alpha-papillomavirus, Beta-papillomavirus, Chi-papillomavirus, Gamma-papillomavirus, Mupapillomavirus, Nupapillomavirus; Polyomaviridae, Alphapolyomavirus, Betapolyomavirus, Gammapolyomavirus, Deltapolyomavirus; Poxviridae, Molluscipoxvirus, Orthopoxvirus, Parapoxvirus; Anelloviridae, Alphatorquevirus, Betatorquevirus, Gammatorquevirus; Circoviridae, Cyclovirus; Genomoviridae, Gemycircularvirus, Gemykibivirus, Gemyvongvirus; Parvoviridae, Erythrovirus, Dependovirus, Bocavirus; Hepadnaviridae, Orthohepadnavirus; Retroviridae, Gammaretrovirus, Deltaretrovirus, Lentivirus, Simiispumavirus; Picobirnaviridae, Picobirnavirus; Reoviridae, Coltivirus, Rotavirus, Seadornavirus; Coronaviridae, Alphacoronavirus, Betacoronavirus, Torovirus; Astroviridae, Mamastrovirus; Caliciviridae, Norovirus, Sapovirus; Flaviviridae, Flavivirus, Hepacivirus, Pegivirus; Hepeviridae, Orthohepevirus; Matonaviridae, Rubivirus; Picornaviridae, Cardiovirus, Cosavirus, Enterovirus, Hepatovirus, Kobuvirus, Parechovirus, Rosavirus, Salivirus; Togaviridae, Alphavirus; Filoviridae, Ebolavirus, Marburgvirus; Paramyxoviridae, Henipavirus, Morbilivirus, Respirovirus, Rubulavirus; Pneumoviridae, Metapneumovirus, Orthopneumovirus; Rhabdoviridae, Ledantevirus, Lyssavirus, Vesiculovirus; Arenaviridae, Mammarenavirus; Hantaviridae, Orthohantavirus; Nairoviridae, Orthonairovirus; Peribunyaviridae, Orthobunyavirus; Phenuiviridae, Phlebovirus; Orthomyxoviridae, Alphainfluenzavirus, Betainfluenzavirus, Gammainfluenzavirus, Quaranjavirus, Thogotovirus, Deltavirus.

EXAMPLES

Exemplary details are presented below, which are for a better understanding of the invention and not intended to be limiting unless otherwise specified, on (1) the process for treating silicone substrates, (2) determining compositions of matter, (3) studies on leaching of active ingredient, (4) anti-microbial effectiveness, (5) biocompatibility and (6) reduced biofouling.

(1) Process for Treating Silicone Substrates.

Materials: N, N-dimethyldecylamine (amine C-10), N, N-dimethyldodecylamine (amine C-12), N, N-Dimethyltetradecylamine (amine C-14), N, N-dimethylhexadecylamine (amine C-16), N, N-Dimethyloctadecylamine (amine C-18), dodecylamine (amine C-12-2H) were purchased from TCI America. Ethanol (Fisher Scientific), deionized water (DI). N, N-dimethyldodecylamine was distilled. Food grade silicone sheets were obtained from McMaster-Carr (product number 5827T31). Disks with diameter (12.7 mm) were cut out of the sheet using a regular hole puncher. Disks were cleaned by immersion in ethanol for 1 h. Ethanol was changed several times until the solvent became clear. Finally, cleaned disks were stirred in DI water for 1 h and then dried at 60° C. overnight.

Silicone Catheter Segments.

Example 1. (M-C12-2) Amine treated Bard silicone Foley catheter. The designation M-C12-2 indicates medical grade (M) silicone catheter treated with 2 wt % N, N-dimethyldodecylamine (Table 1) in ethanol. Bard All-Silicone Foley catheters (Product #165822, Fr. 22) were cut into 1 cm long segments and then cut into halves, creating 1 cm long half-pipe pieces. These pieces were placed into ethanol at 40° C. that contained 2.0 wt % of the C12 amine. The reactor was stirred continuously for 1 h. The samples were then removed and washed in DI water three times. Prior to characterization, the samples were then stored for 6 h in a sterilized phosphate buffered solution (PBS) (pH 7). The container was placed in a biosafety cabinet equipped with ultraviolet (UV) radiation for sterilization.

Example 2. M-C14-2. The designation M-C14-2 indicates medical grade (M) silicone catheter treated with 2 wt % N,N-dimethyltetradecylamine (C14 amine) in ethanol. Bard All-silicone Foley catheters (Fr. 22) were cut into 1 cm long segments and then cut into halves, creating 1 cm long half-pipe pieces. These pieces were placed into solution of 2.0 wt % C14 amine (Table 1) in ethanol preheated to 40° C. The reactor was stirred continuously for 1 h. The samples were then removed and washed in DI water three times. The samples were then stored in sterilized phosphate buffered solution (pH 7). The container was kept for 6 h in a biosafety cabinet equipped with ultraviolet (UV) radiation for sterilization.

Additional Examples, Examples 3-6, are listed in Table 2. In those examples, the treatment time (1 h) and temperature (40° C.) were identical for all compositions. Structures for some non-limiting amines are shown in Table 1.

TABLE 1

Structures and designations for various amines

| Amine | Structure and designation |
|---|---|
| N,N-dimethylhexylamine | 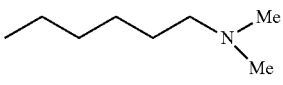<br>C-6 |
| N,N-dimethyloctylamine | 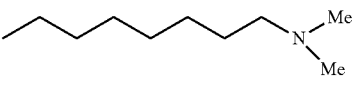<br>C-8 |
| N,N-dimethyldecylamine | 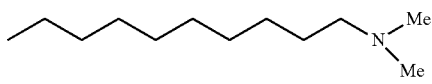<br>C-10 |
| N,N-dimethyldodecylamine | 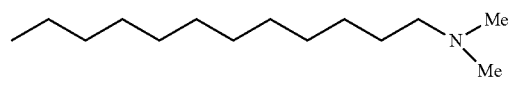<br>C-12 |
| N,N-dimethyltetradecylamine | 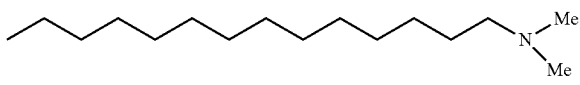<br>C-14 |
| N,N-dimethylhexadecylamine | 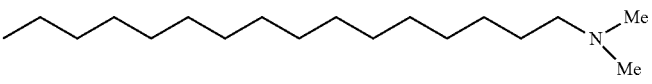<br>C-16 |
| N,N-dimethyloctadecylamine | 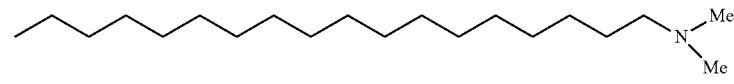<br>C-18 |

TABLE 1-continued

Structures and designations for various amines

| Amine | Structure and designation |
|---|---|
| N,N-dimethyleicosanamine | 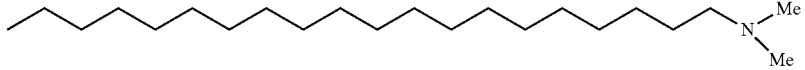 C-20 |
| hexylamine | 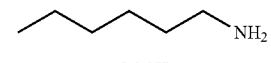 C6-2H |
| octylamine | 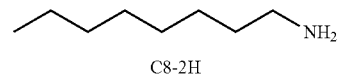 C8-2H |
| decylamine | 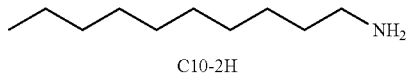 C10-2H |
| dodecylamine | 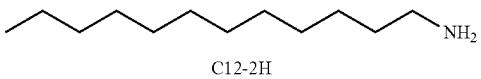 C12-2H |
| tetradecylamine | 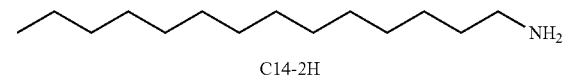 C14-2H |
| hexadecylamine | 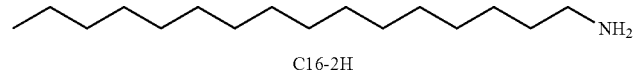 C16-2H |
| octadecylamine | 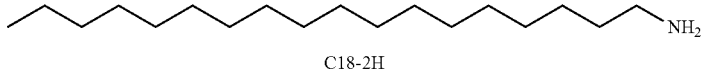 [SMILES: CCCCCCCCCCCCCCCCCCN ; "C18-2H"] C18-2H |
| eicosanamine | 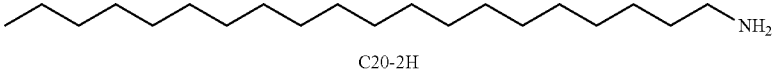 [SMILES: CCCCCCCCCCCCCCCCCCCCN] C20-2H |

TABLE 2

Preparation conditions for modification of medical grade silicone catheters at 40° C. with amines M-C10, M-C16, M-18 and M-C12-2H.

| Example | Product designation | Amine | Amine feed concentration |
|---|---|---|---|
| 3 | M-C10-2 | N,N-dimethyldecylamine | 2 wt % |
| 4 | M-C16-2 | N,N-dimethylhexadecylamine | 2 wt % |
| 5 | M-C18-2 | N,N-Dimethyloctadecylamine | 2 wt % |
| 6 | M-C12-2H | Dodecylamine | 2 wt % |

Food Grade Silicone

Food grade silicone (F) was also treated and the resulting compositions were tested for antimicrobial effectiveness.

Example 7. (F-C12-2(25)) Amine treated food grade silicone disks. The designation F-C12-2 indicates food grade silicone disks treated with 2 wt % N,N-dimethyldodecylamine (C12) feed in ethanol. The disks were cut from an 0.8 mm thick food grade silicone sheet using a punch with a 12.5 mm diameter die. Prior to treating, all disks were washed in ethanol for 15 min and dried overnight at 100° C. The washed and dried silicone disks were stirred in 2.0 wt % C12 ethanol solution for 15 min at 25° C. The thus-treated samples were then removed and washed in DI water three times. The samples were then stored in sterilized phosphate buffered solution (pH 7). A typical storage time was 6 h in a biosafety cabinet equipped with ultraviolet (UV) radiation for sterilization.

Example 8. (F-C14-2(25)) Amine treated food grade silicone disks. The designation F-C14-2 indicates food grade silicone disks treated with 2 wt % N,N-dimethyltetradecylamine (C14) amine feed in ethanol. The silicone disks were stirred in 2.0 wt % C14 ethanol solution for 15 min at 25° C. (ambient temperature). The samples were then removed and washed with DI water three times. The samples were then stored in sterilized phosphate buffered solution (pH 7). The storage time before removing samples for various tests was 6 hr in a biosafety cabinet equipped with ultraviolet (UV) radiation for sterilization.

Additional examples, Examples 9-12, are listed in Table 3. In those examples, the treatment time (15 min) and temperature (25° C.) were identical for all compositions. Structures for the amines are shown in Table 1.

TABLE 3

Modification of food grade silicone disks (F).
Treatments were carried out at 25° C. for
15 min with an amine feed concentration of 2 wt %.

| Example | Designation | Amine |
|---|---|---|
| 9 | F-C10-2(25) | N,N-dimethyldecylamine |
| 10 | F-C16-2(25) | N,N-dimethylhexadecylamine |
| 11 | F-C18-2(25) | N,N-dimethyloctadecylamine |
| 12 | F-C12-2H(25) | Dodecylamine |

Example 13. (F-C12-2(40)) Amine treated food grade silicone disks at 40° C. The designation F-C12-2(40) indicates food grade (F) silicone discs treated with 2 wt % N,N-dimethyldodecylamine (C12) in ethanol at 40° C. The silicone disks were placed into ethanol at 40° C. that contained 2.0 wt % C12 amine. The reactor was stirred continuously for 1 h. The samples were then removed and washed in DI water three times. Prior to characterization, the samples were then stored for 6 h in a sterilized phosphate buffered solution (pH 7). The container was placed in a biosafety cabinet equipped with ultraviolet (UV) radiation for sterilization.

(2) Determining Composition of matter. Amine treated medical grade silicone catheters (M) and amine treated food grade silicone disks (F) were investigated to determine their composition. Two methods were used:

a. Titration of acid-extracted amine. The titration method takes advantage of the basicity of tertiary alkyl amines. Tertiary alkyl amines are basic, and in the presence of aqueous acids, the tertiary alkyl amines are protonated, which results in a decrease of free hydrogen ions and an increase in pH. Immersion of treated samples in a dilute acid of known pH for a designated time, followed by measuring the pH, gives a qualitative measure of the presence of alkyl amines. To obtain a quantitative measure for weight percent alkyl amine in treated samples, back titration of the post-extraction solution (more alkaline) with an acid of known concentration yields a quantitative analysis for amine weight percent in the treated silicone catheter segments.

Procedure for medical grade silicone catheters and food grade disks: After amine treatment, samples were thoroughly rinsed with DI water and stored in a sealed plastic bag. Storing in phosphate buffered saline was an alternative. Samples used for titration are either 1 cm long amine-treated silicone catheter segments or 12.5 mm diameter amine treated disks. 5 samples were placed in a screw cap vial with 0.010 M HCl at a ratio of 1 mL/sample. The samples were then sonicated for 60 min in a water bath to extract amine. After extraction, samples were removed from the extraction solution and a universal indicator

TABLE 4

Treatment of medical grade silicone catheters (M)
and food grade catheters (F) at 40° C.: feed
C12 amine weight percentage, amine weight per unit
area and sample weight percentage (from titration data)

| Wt. % of C12 in Feed | M-C12(40) mg/cm² | M-C12(40) Wt % | F-C12(40) mg/cm² | F-C12(40) Wt % |
|---|---|---|---|---|
| 1 | 0.62 | 0.46 | 0.26 | 0.56 |
| 2 | 0.86 | 0.64 | 1.03 | 2.24 |
| 4 | 1.07 | 0.8 | 1.24 | 2.68 |
| 6 | 1.25 | 0.93 | 1.49 | 3.24 |
| 8 | 1.39 | 1.04 | 2.37 | 5.15 |

(Fisher) is added to the solution to give visual confirmation of a pH change. The pH of the solution is then measured with a pH meter. Extraction of the amine from the amine-treated silicone resulted in an increase of pH of the extraction medium. To determine the amount of antimicrobial agent extracted, 0.020 M HCl was used as the titrant for the extraction solution. 0.020 M HCl was added to the extraction solution until the pH returned to the pre-extraction level. The volume of 0.020 M HCl added was used to calculate the amount of amine extracted using the equations below:

$$\text{Volume}(L) \text{ of } HCl \text{ added} \times \text{Concentration of } HC(M) = \text{mol } HCl \qquad \text{Eq. 1.}$$

$$\text{mol } HCl \times \frac{1 \text{ mol amine } (NR_3)}{1 \text{ mol } HCl} \times \text{Avogadro's Number } (N_A) = \text{ \# of } NR_3 \text{ molecules.} \qquad \text{Eq 2}$$

$$\text{\# of } NR_3 \text{ molecules/Sample Surface area(cm}^2\text{)} = NR_2 \text{ concentration} \qquad \text{Eq 3.}$$

The calculation for the total amine weight percentage is as follows.

$$\text{\# of } NR_3 \text{ molecules}/N_A = mol \text{ of } NR_3 \qquad \text{Eq 4.}$$

$$mol \text{ of } NR_3 \times \text{Molar Mass of } NR_3 = \text{mass of } NR_3 \qquad \text{Eq 5.}$$

$$(\text{mass of } NR_3/\text{mass of sample}) \times 100 = NR_3 \text{ mass percentage} \qquad \text{Eq 6.}$$

Figure 1:
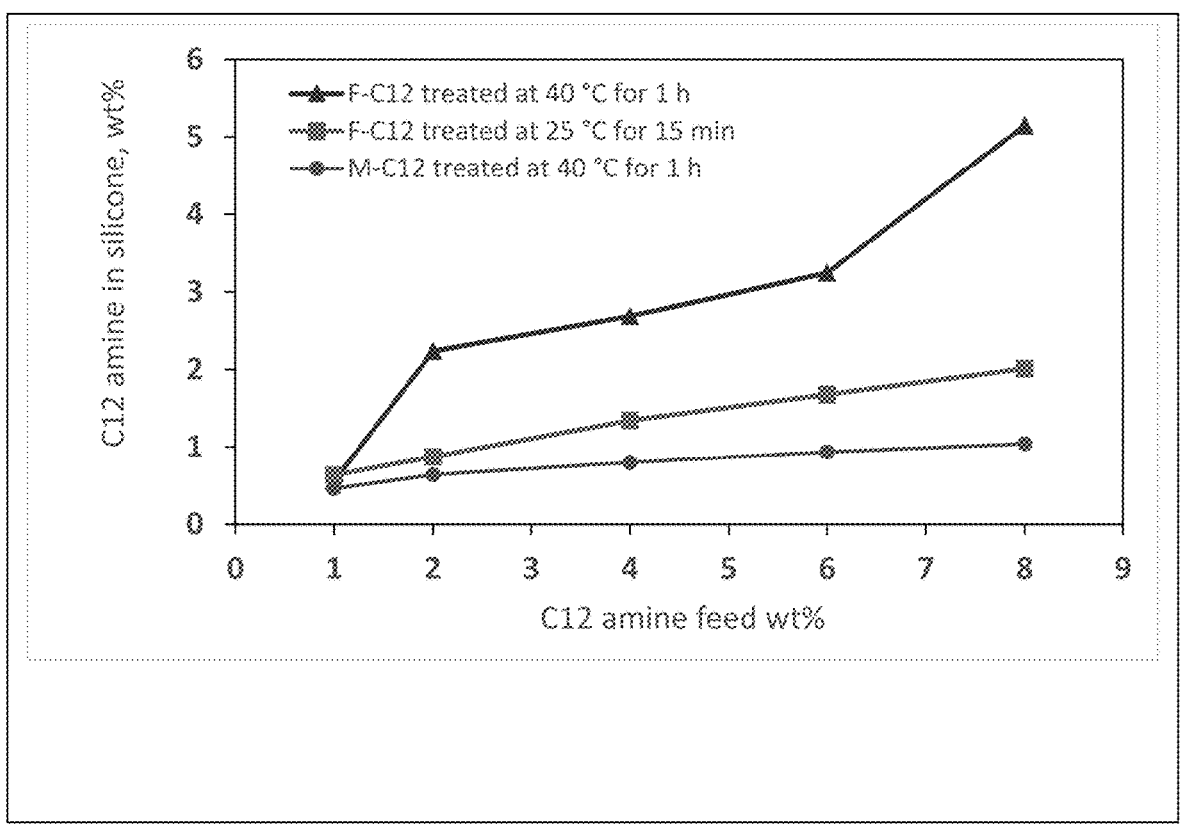
FIG. 1. C12 amine wt % in sample determined by titration vs C12 amine wt % in feed for treated medical grade silicone catheter segments (M-C12) and food grade silicone disks (F-C12(25)) and (F-C12(40)).
Figure 2:
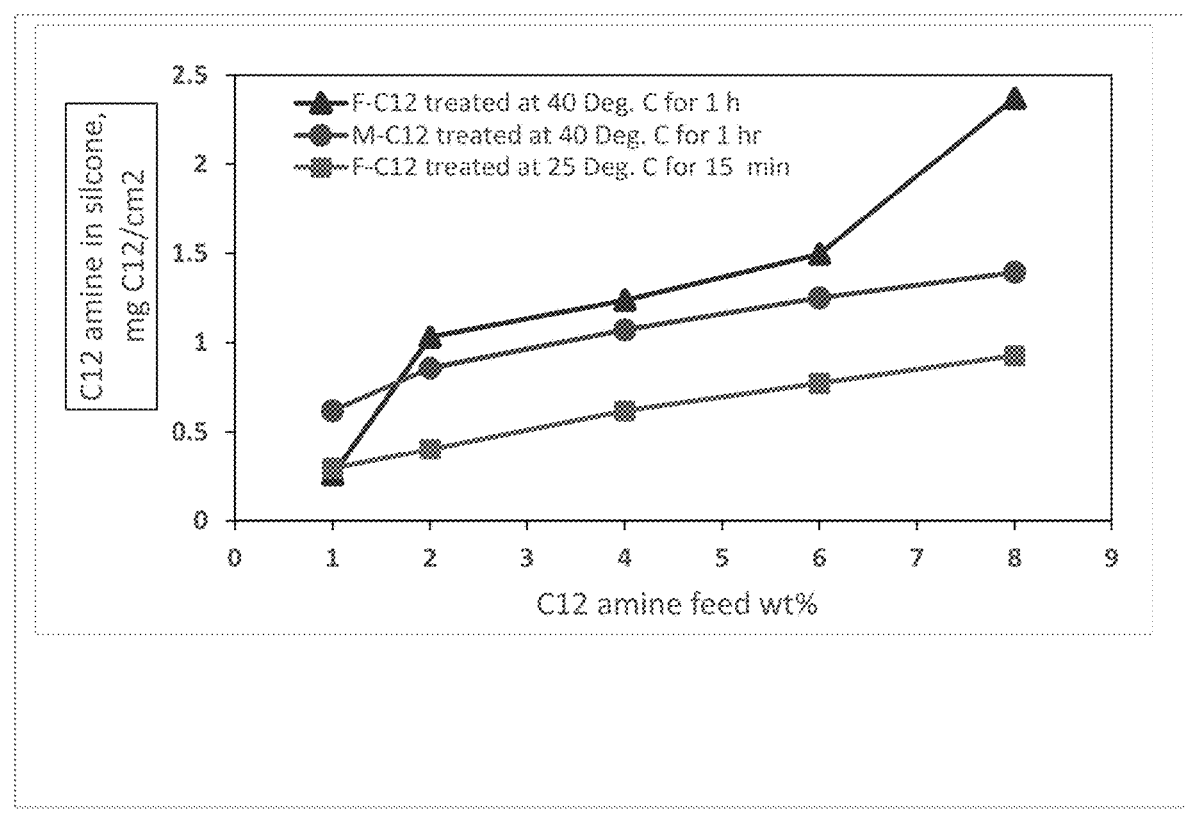
FIG. 2. C12 amine wt in sample determined by titration/sample surface area vs C12 amine wt % in feed for the treated medical grade silicone catheter segments (M-C12) and food grade silicone disks (F-C12(25)) and (F-C12(40)).
Figure 3:
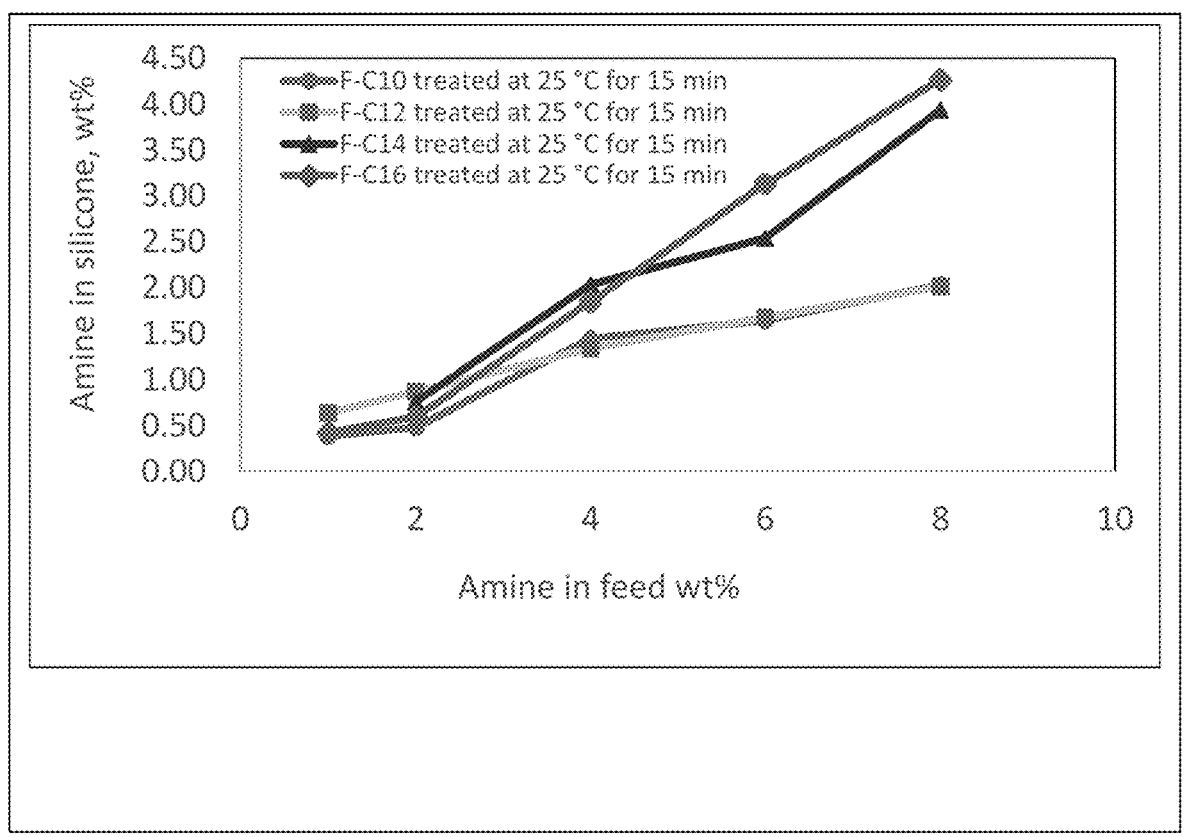
FIG. 3. Amine wt % in sample determined by titration vs. amine wt % in feed for treated food grade silicone disks (F-C10, -C12, -C14, -C16(25)).

Table 4 shows feed C12 amine weight percentages, the amine weight per unit area and wt % in the treated silicone catheter segments. FIG. 1 shows a graph of wt % C12 feed versus wt % C12 in the silicone catheter (M) and food grade silicon treated at 25° C. and 40° C. The C12 uptake increases regularly with increasing feed concentration. For 2 wt % feed, a preferred composition, 0.64 wt % of C12 is found in the silicone catheter tubing product (Table 4 and 5, FIGS. 1 and 2). FIG. 3 shows a graph of the feed wt % for C10, C12, C14 and C16 amine vs wt % of amine on food grade silicone catheter. The uptake of amine increased regularly with increasing feed concentration similarly to that exhibited by C12 amine in FIG. 1. This demonstrates that the surface concentration of amine, regardless of alkyl chain length, can be controlled by manipulation of amine feed wt %.

TABLE 5

Treatment of food grade catheters (F) at 25°
C.: feed C12 amine weight percentage, amine weight
per unit area and sample weight percentage.

| Feed Weight (%) | F-C12(25) mg/cm² | F-C12(25) Wt % |
|---|---|---|
| 1 | 0.29 | 0.64 |
| 2 | 0.40 | 0.87 |
| 4 | 0.62 | 1.34 |
| 6 | 0.77 | 1.68 |
| 8 | 0.93 | 2.01 | b. ¹H-Nuclear Magnetic Resonance Spectroscopy (¹H-NMR)

Figure 5:
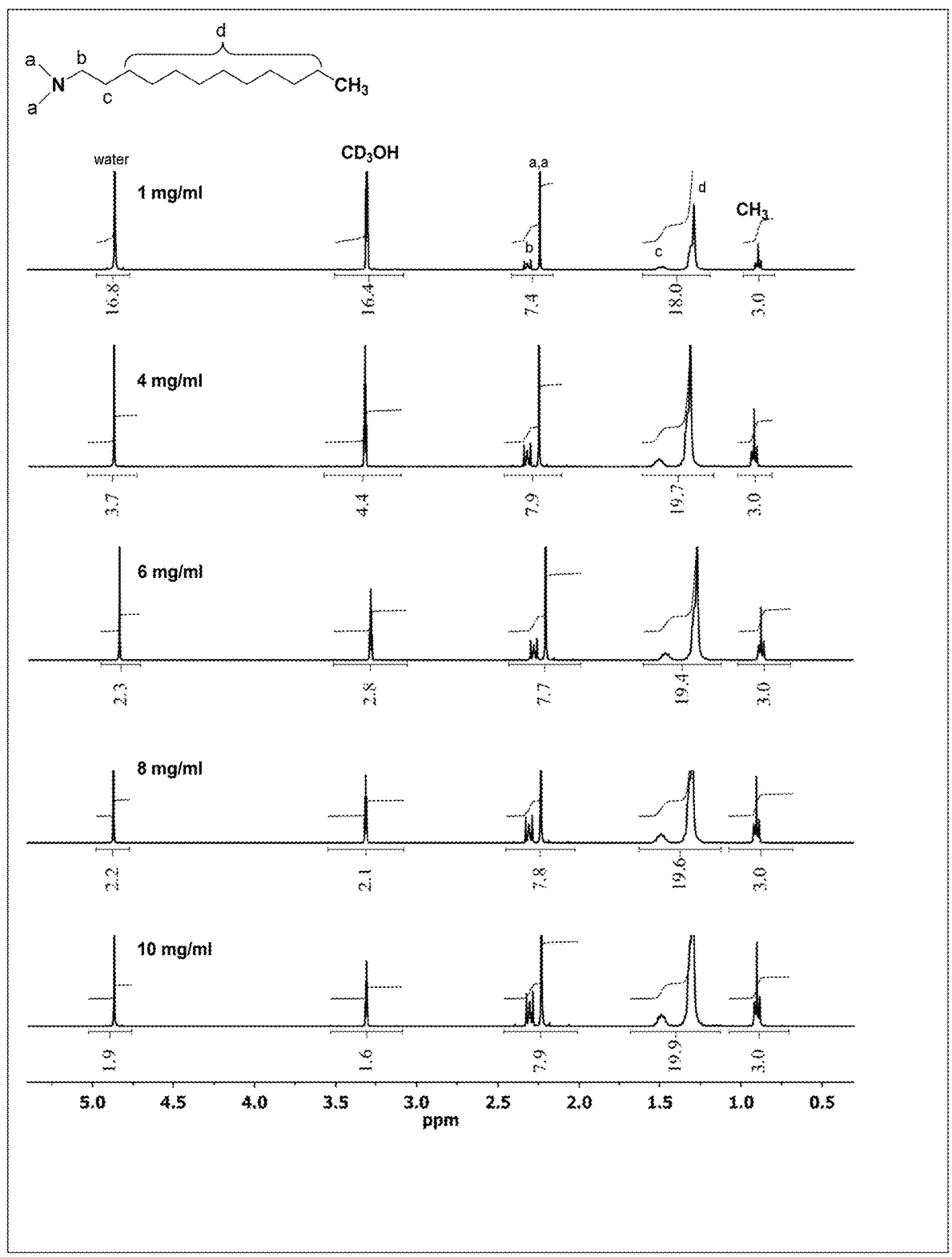
FIG. 5. $^1$H-NMR spectra of 1, 4, 6, 8, and 10 mg/ml standard solutions of distilled N, N-dimethyldodecylamine (C12) in $CD_3OD$ for calibration curve.
Figure 6:
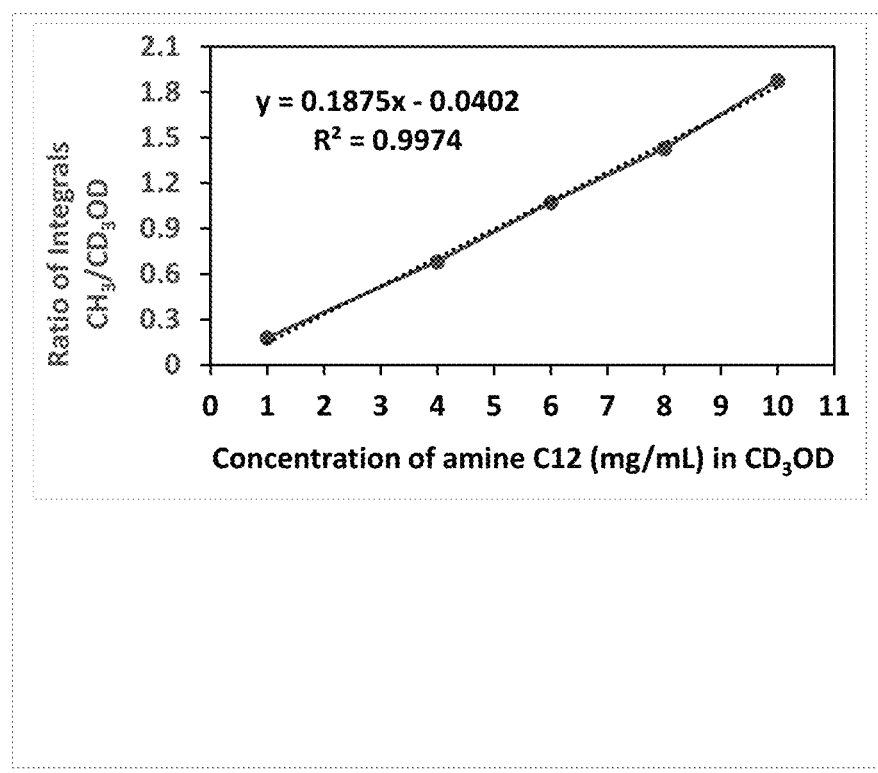
FIG. 6. Calibration curve of C12 amine $CH_3/CD_3OD$ determined by $^1$H-NMR vs standard solution concentration of C12 amine in $CD_3OD$ (dotted line is least squares fit).

The composition of matter for amine treated silicone catheters was also established using ¹H-NMR spectroscopy. Deuterated methanol ($CD_3OD$) was used as a solvent to extract C12 amine from the amine-treated silicone substrates. In the first step of the quantitative ¹H-NMR analysis, ¹H-NMR spectra of 1 mL standards with C12 amine concentrations of 1, 4, 6, 8, and 10 mg/mL (distilled N, N-dimethyldodecylamine (C12) in CD$_3$OD) were obtained. The Integral for the methyl proton peak CH$_3$ at 0.9 ppm was set to 3 as the amine methyl group has three protons. This was the standard for all C12 amine treated silicone catheter segments (FIG. 5). Ratios of integral values of CH$_3$ signals of the amine to that of the peak at 3.31 ppm for protons of deuterated methanol were used for preparing a calibration curve (FIG. 6).

Four sets of silicone catheter segments cut to half pipes were modified with C12 amine feed concentration of 1, 2, 4, and 6 wt. % (M-C12-1, M-C12-2, M-C12-4, and M-C12-6). The treated catheter segments were stored in PBS solution overnight prior to the extraction procedure.

Figure 4:
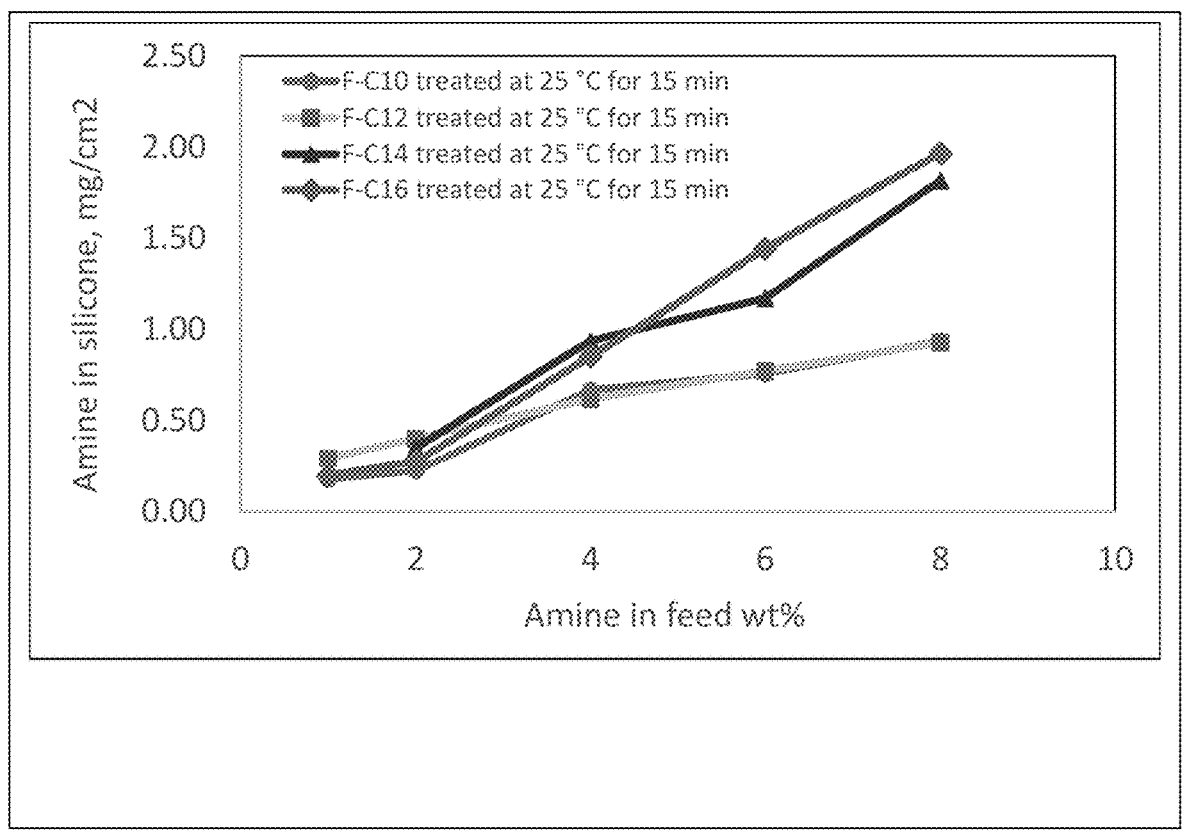
FIG. 4. Amine wt in sample determined by titration/sample surface area vs amine wt % in feed for treated food grade silicone disks (F-C10, -C12, -C14, -C16(25)).

After drying with a Kimwipe, five segments of each set were gently shaken in 1.5 mL CD$_3$OD overnight in tightly closed vials at 37° C., to prepare the extract solutions. $^1$H-NMR spectra of 1 mL extract solutions show the ratio of integral values of the CH$_3$ signal of extracted amine at 0.9 ppm to that of the solvent signal peak at 3.31 ppm (FIG. 5). The calibration curve of integral ratios (area CH$_3$ of amine/ area CD$_3$OD, FIG. 4) versus the concentration of the C12 amine was used to determine the concentration of extracted C12 amine in 1.5 ml of CD$_3$OD for all four sets. Finally, given that the total weight of 5 unmodified segments (836 mg) the weight percent (wt %) of C12 amine in modified silicon segments was calculated and is summarized in Table 6.

TABLE 6

In brief, silicone catheter segments were modified with C12 amine in ethanol at 40° C. for 1 h. Shown are weight percent C12 amine in the treated medical grade silicone catheters M-C12-1, M-C12-2, M-C12-4, M-C12-6 (process described in Example 1).

| Designation | CH$_3$ area | CD$_3$OD area | Ratio CH$_3$/CD$_3$OD | Conc. of C12 in NMR tube* (mg/mL) | Weight of C12 in 1.5 ml (mg) | Wt % C12 | Concentration of C12 amine (mg/cm$^2$)*** |
|---|---|---|---|---|---|---|---|
| M-C12-1 | 3 | 9.2 | 0.33 | 1.95 | 2.93 | 0.35 | 0.25 |
| M-C12-2 | 3 | 4.9 | 0.61 | 3.48 | 5.22 | 0.62 | 0.46 |
| M-C12-4 | 3 | 2.6 | 1.15 | 6.37 | 9.55 | 1.14 | 0.80 |
| M-C12-6 | 3 | 1.8 | 1.67 | 9.10 | 13.65 | 1.63 | 1.14 |

Figure 7:
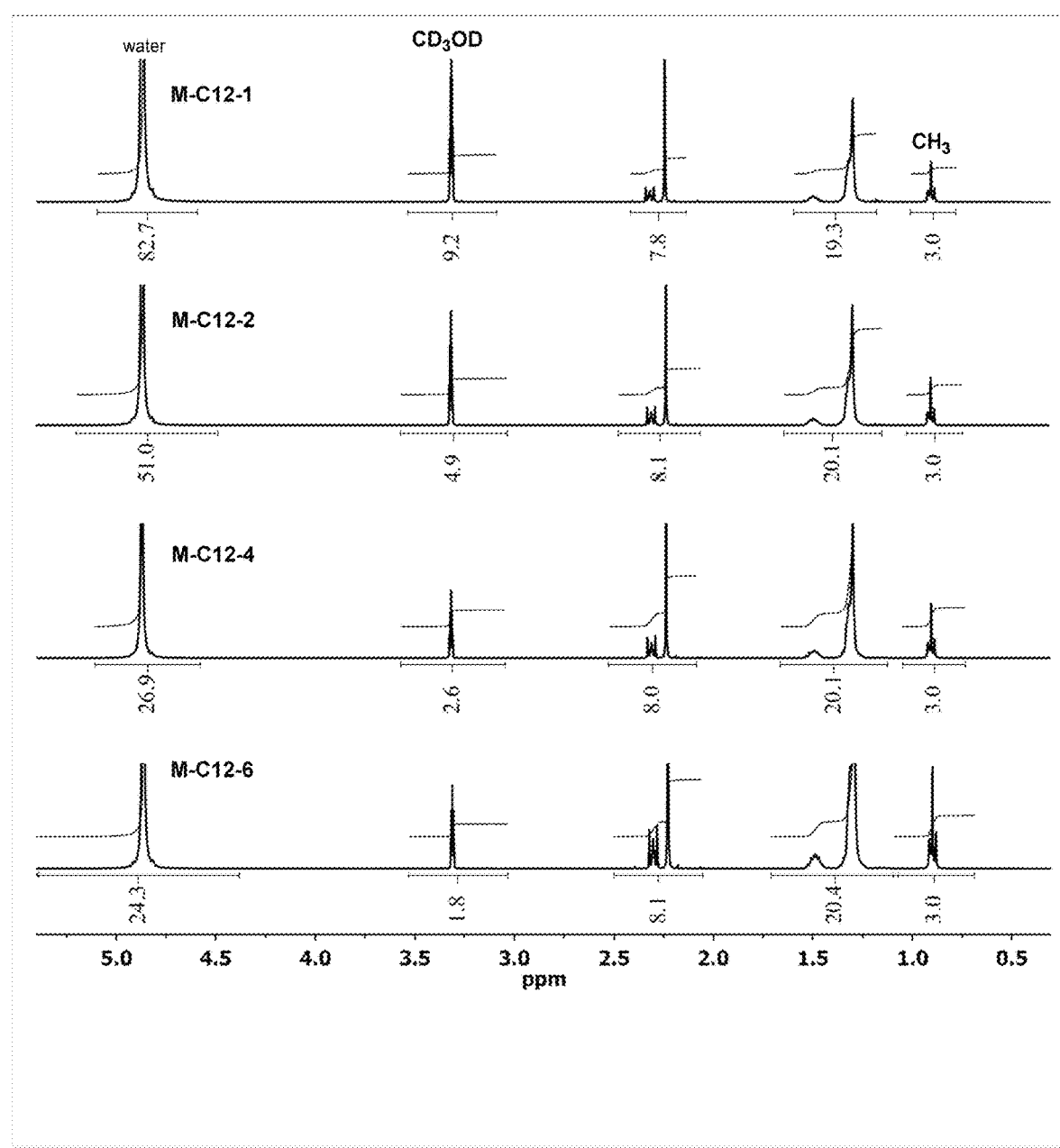
FIG. 7. $^1$H NMR spectra of solutions obtained from extracting medical grade silicone catheter segments treated with C12 amine in ethanol at 40° C. for 1 h. Shown are $^1$H NMR spectra of solutions after extraction of M-C12-1, M-C12-2, M-C12-4, M-C12-6 (5 half segments per set) with 1.5 mL of $CD_3OD$ overnight at 37° C.
Figure 8:
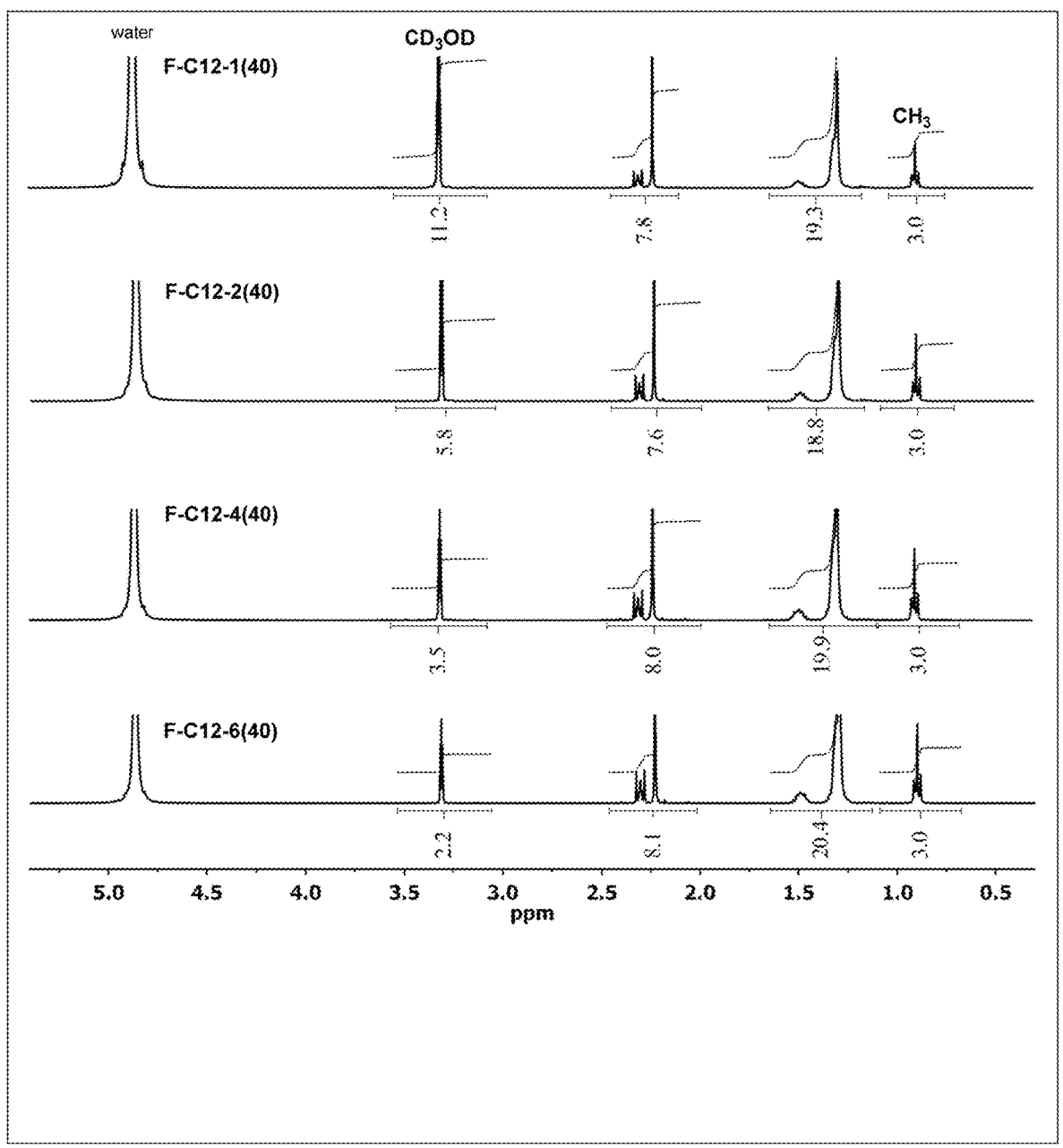
FIG. 8. $^1$H NMR spectra of solutions obtained from extracting food grade silicone disks treated with C12 amine in ethanol at 40° C. for 1 h. Shown are $^1$H NMR spectra of solutions after extraction of F-C12-1(40), F-C12-2(40), F-C12-4(40), F-C12-6(40) (5 disks per set) with 1.5 mL of $CD_3OD$ overnight at 37° C.
Figure 9:
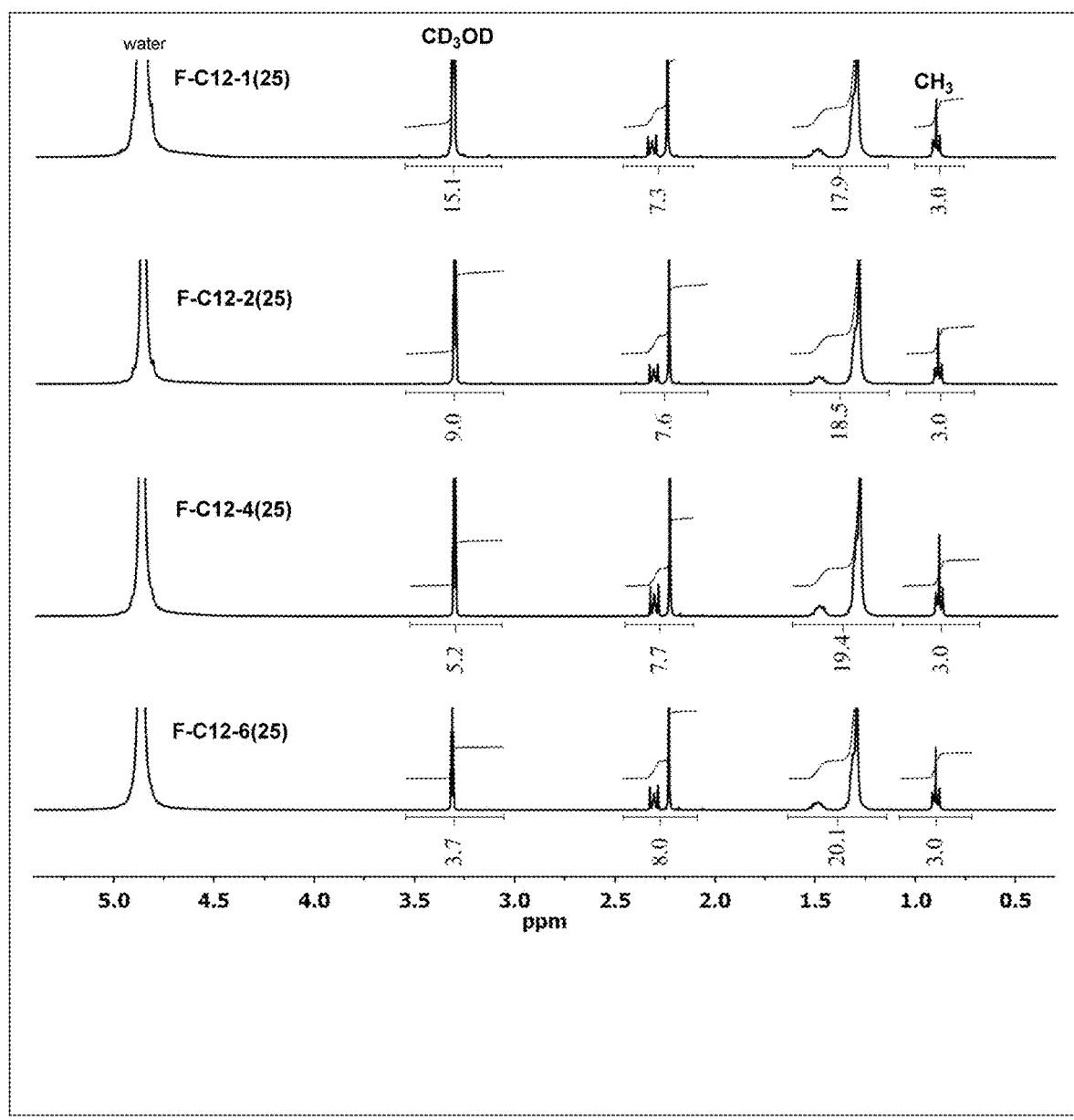
FIG. 9. $^1$H NMR spectra of solutions obtained from extracting food grade silicone disks were treated with C12 amine in ethanol at 25° C. for 15 min (Example 7). Shown are $^1$H NMR spectra of the solutions after extraction of F-C12-1(25), F-C12-2(25), F-C12-4(25), F-C12-6(25) (5 disks per set) with 1.5 mL of $CD_3OD$ overnight at 37° C.
Figure 10:
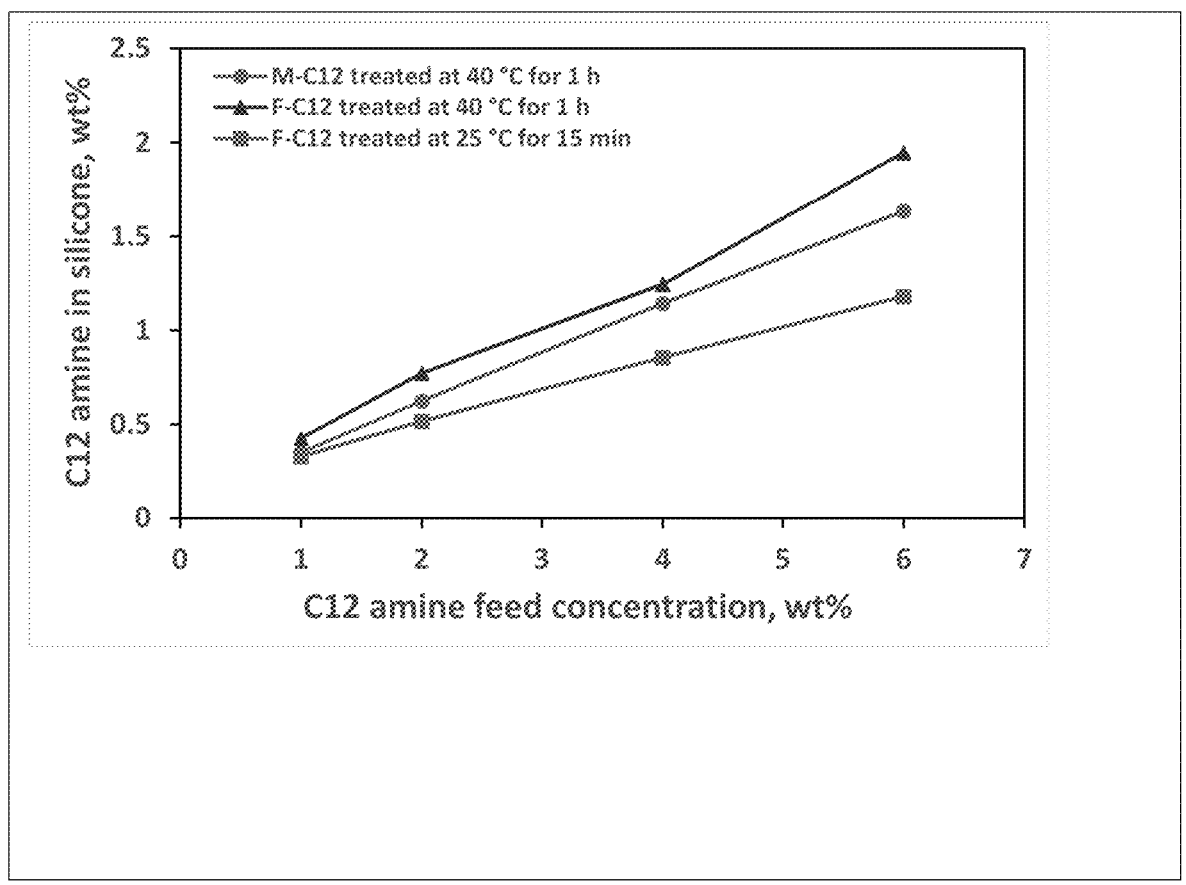
FIG. 10. C12 amine wt % in sample determined by $^1$H-NMR vs C12 amine wt % in feed for treated medical grade silicone catheter segments (M-C12) and food grade silicone disks (F-C12(25)) and (F-C12(40)).
Figure 11:
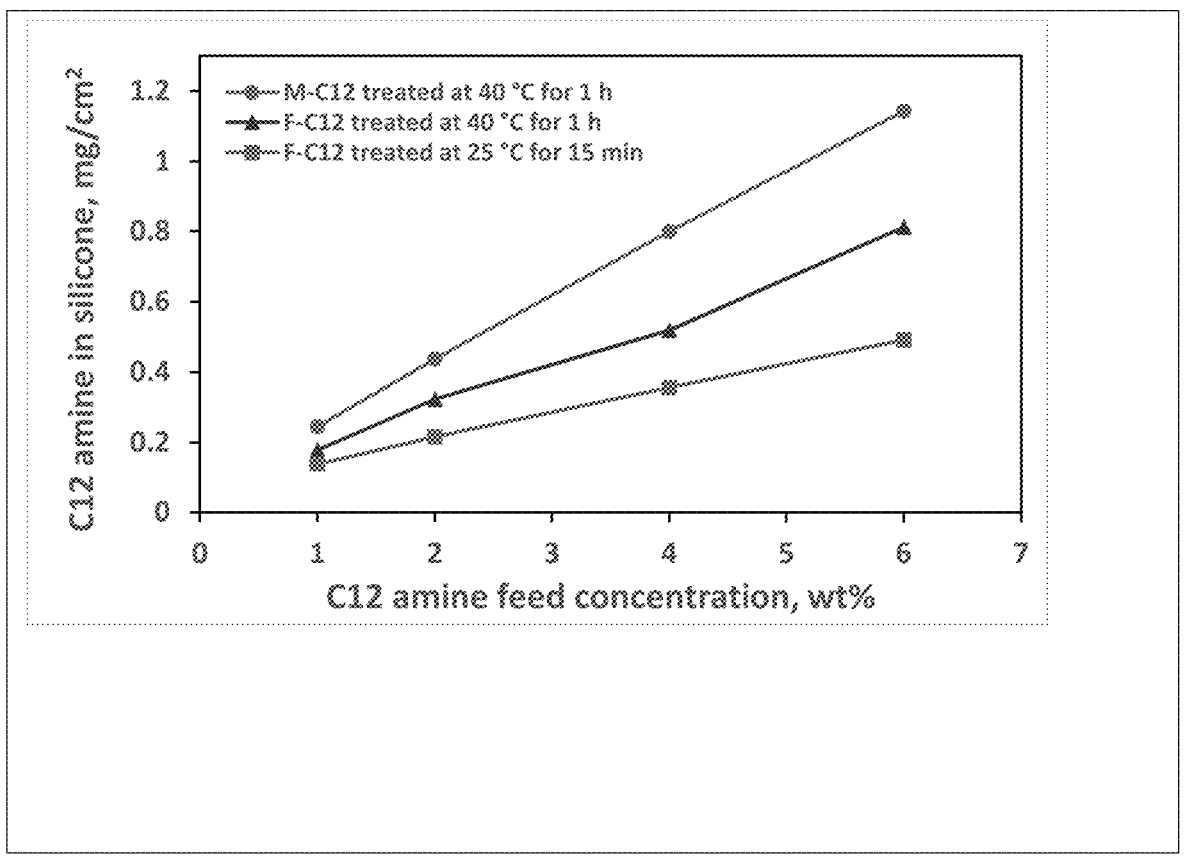
FIG. 11. C12 amine wt in sample determined by $^1$H-NMR/sample surface area vs C12 amine wt % in feed for the treated medical grade silicone catheter segments (M-C12 (40)) and food grade silicone disks (F-C12(25)) and (F-C12 (40)).

*Concentration of C12 was calculated from the calibration curve
** Total weight of 5 unmodified silicone half-pipe segments is 836 mg
*Surface area of one silicone half-pipe segment is 2.39 cm$^2$ To investigate the composition of matter for food grade silicone, disks were modified with 1, 2, 4, and 6% wt % C-12 amine feed concentration in ethanol at 40° C. for 1 h. A second treatment condition was room temperature (25° C.) for 15 min. For each composition, 5 disks (F-C12-1, F-C12-2, F-C12-4, and F-C12-6) were gently stirred in 1.5 ml of deuterated methanol CD$_3$OD overnight at 37° C. $^1$H-NMR spectra of the extracts are presented in FIG. 6 and FIG. 7**, while the composition of matter is summarized in Tables 7 and 8, respectively.

TABLE 7

In brief, food grade silicone disks were modified with C12 amine in ethanol at 40° C. for 1 h. C12 amine wt% is shown for F-C12-1(40), F-C12-2(40), F-C12-4(40), F-C12-6(40) (process described in Example 13)

| Designation | CH$_3$ area | CD$_3$OD area | Ratio CH$_3$/CD$_3$OD | Conc. of C12 in NMR tube* (mg/mL) | Weight of C12 in 1.5 ml (mg) | Wt % of C12 | Concentration of C12 amine (mg/cm$^2$)*** |
|---|---|---|---|---|---|---|---|
| F-C12-1(40) | 3 | 11.2 | 0.27 | 1.64 | 2.46 | 0.43 | 0.18 |
| F-C12-2(40) | 3 | 5.8 | 0.52 | 2.97 | 4.46 | 0.77 | 0.32 |
| F-C12-4(40) | 3 | 3.5 | 0.86 | 4.79 | 7.18 | 1.24 | 0.52 |
| F-C12-6(40) | 3 | 2.2 | 1.36 | 7.49 | 11.23 | 1.95 | 0.81 |

*Concentration of C12 was calculated from the calibration curve
** Total weight of 5 unmodified food grade silicone disks is 577 mg
***Surface area of one silicone disk is 2.77 cm$^2$.

TABLE 8

In brief, food grade silicone disks were modified with C12 amine in ethanol at 25° C. for 15 min. Weight percent of C12 amine in the treated food grade silicone disks is shown for F-C12-1(25), F-C12-2(25), F-C12-4(25), F-C12-6(25) (process details are described in Example 7).

| Designation | $CH_3$ area | $CD_3OD$ area | Ratio $CH_3/CD_3OD$ | Conc. of C12 in NMR tube* (mg/mL) | Weight of C12 in 1.5 ml (mg) | Wt % of C12 | Concentration of C12 amine (mg/cm$^2$)*** |
|---|---|---|---|---|---|---|---|
| F-C12-1(25) | 3 | 15.1 | 0.20 | 1.27 | 1.91 | 0.33 | 0.14 |
| F-C12-2(25) | 3 | 9.0 | 0.33 | 1.99 | 2.99 | 0.52 | 0.22 |
| F-C12-4(25) | 3 | 5.2 | 0.58 | 3.30 | 4.94 | 0.86 | 0.36 |
| F-C12-6(25) | 3 | 3.7 | 0.81 | 4.54 | 6.81 | 1.18 | 0.49 |

*Concentration of C12 was calculated from the calibration curve
** Total weight of 5 unmodified food grade silicone disks is 577 mg
***Surface area of one silicone disk is 2.77 cm$^2$ Zone of inhibition (ZOI) or Kirby-Bauer test for modified food grade silicone disks. M and F are designations used for medical grade and food grade silicone respectively. Early on, experiments were done with food grade silicone disks. A surprise was the finding that silicone catheters (either Bard or others) required higher temperatures for amine treatment. "Standard" conditions for catheter silicone tubes became 40 C.

Figure 12:
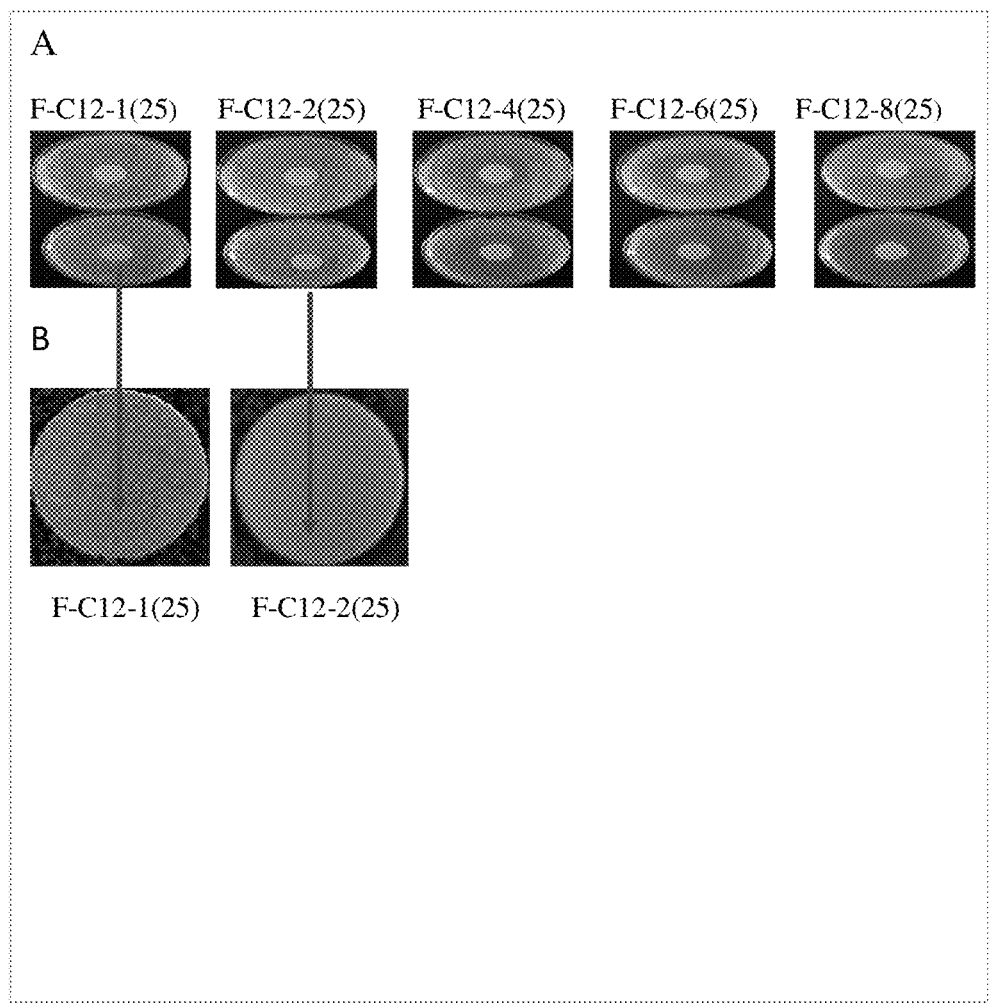
FIG. 12. A, Photographs of Zone of Inhibition (ZOI) results of C12-treated food grade silicone disks (25° C.)

Zone of Inhibition tests (ZOI) for modified food grade silicone disks treated at 25° C. were carried out. 100 µL Gram-negative *K. pneumoniae* bacterial culture stock solution ($1.5 \times 10^9$ cfu/mL) was uniformly spread on LB medium agar plates to form a "lawn" of bacteria. Food grade disks were placed on the agar plates and incubated overnight at 37° C. As seen in FIG. 12, disks treated with higher feed weight percent have increasing ZOIs. Conversely, as feed wt % is decreased, the ZOI decreases so that samples with 2 wt % and 1 wt % feed, respectively, showed no ZOI. The weight percent C12 for these samples is 0.64 and 0.87%, respectively (Table 5). Thus, the threshold for the ZOI is >0.87 wt % C12.

FIG. 12B shows a closeup of F-C12-1 and F-C12-2 disks that had no ZOI. No bacterial growth was observed under the F-C12-2 disk (0.87% C12) but the F-C12-1 disk (0.64% C12) shows colonies surviving under the disk. Therefore, another conclusion from the data in FIG. 12 is that for food grade disks treated with C12 at 25° C., a C12 concentration of about 0.87 wt % is needed for antimicrobial effectiveness at 37° C. for 24 h.

Zone of inhibition (ZOI) or Kirby-Bauer test for medical grade silicone catheter segments. A similar ZOI test was employed for medical grade silicone catheters to investigate the C12 leaching. Catheter segments were cut along the length of the tube to yield half-pipes and across the tube to give cross-sections. These samples were treated with C12 amine at 40° C. as described herein.

These samples were placed on a "lawn" of Gram-negative *E. coli* bacteria ($10^9$ cfu/mL) uniformly spread on LB medium agar plates. FIG. 13 shows that catheter segments modified with C12 amine feed concentrations of 1, 2, and 4 wt % did not show a ZOI but a ZOI was observed for the segments modified with amine feed concentration of 6 wt %. M-C12-4 has a C12 concentration of 0.8 wt % (Table 4). There is no ZOI for this composition (FIG. 13). However, a ZOI is observed for M-C12-6 which has a C12 wt % of 0.93. The threshold for leaching of C12 from M-C12 from treated medical grade silicone tubing is thus between 0.8 and 0.93 wt %.

Understanding based on weight percent is a clearer way of understanding the compositional threshold for leaching that results in a ZOI. Interestingly, the weight percent at which a ZOI is observed for C12-treated biomedical grade silicone tubing (>0.8 wt %) is about the same for treated (25° C.) food grade silicone (0.87, Table 5, F-C12-2, 25° C.).

Measurements of the ZOI compositional threshold is important because this threshold for leaching C12 from medical grade silicone is in rough agreement with the threshold for toxicity to human cells. FIG. 23 shows that one threshold for toxicity to HDFs, astrocytes and Schwann cells (ISO 10993-5) is a feed composition of ~C12-3 or a composition of ~0.85 wt % C12 (FIG. 1). Thus, the ZOI that provides a measurement of antimicrobial leaching which exceeds the minimum biocidal concentration of antimicrobial suggests that this level of leaching is also toxic to human cells.

(4) Antimicrobial Effectiveness
  a. ASTM test, E2149-01.

Antimicrobial testing was conducted according to a standard ASTM test, E2149-01, the entire contents of which are hereby incorporated by reference. This test for the determination of antimicrobial activity under dynamic conditions and is also known as the "shake flask" test. In preparation for these tests, a stock bacterial solution was cultured in sterile lysogeny broth (LB) growth medium from a single colony. For *Candida albicans*, the growth medium used was yeast peptone dextrose (YPD). The stock solution was then used to inoculate sterilized flasks containing a designated extraction vehicle (PBS (phosphate buffer solution), laboratory prepared artificial saliva (LAS), M-9 Minimal Growth Medium (M-9), or Simulated Urine). Then the concentration was diluted to $10^5$ cfu/mL using the designated extraction vehicle with a final total volume of 20 mL. Ultraviolet visible (UV-Vis) spectroscopy was used to establish the initial concentration of the bacterial solution at a wavelength of 600 nm. {King, 2010 #8}

Bard silicone Foley catheter (Fr. 24) segments were treated with C12-2 as described in Example 1. Treated silicone half-pipes and control samples (untreated catheter segments) were then added to separate flasks at approximately 1.16 cm$^2$/mL surface area to volume ratio. A flask containing just the extraction vehicle and pathogen was also introduced as an additional control parameter. The flasks were then subjected to gentle rotation at 37° C. in an incubator-shaker. Afterwards, aliquots from each flask were removed at selected time intervals then serial diluted and plated on agar. The plates were incubated for 24 h or more at 37° C. and bacterial colonies were then counted to establish log reduction. The antimicrobial effectiveness of treated silicone was challenged against pathogens most common for urinary tract infections using this shake flask test. Table 9 has a summary of results. M-9 Minimal Growth Medium Preparation (M-9): M-9 minimal growth media is a growth media used for specific bacteria strains that require salt additives for culturing purposes. Specifically, *Staphylococcus aureus* requires such a media in order to effectively conduct the E2149 Antimicrobial Test. The preparation of the M-9 was carried out in a multistep procedure using a level 2 bio-safety hood to ensure sterilization. Step 1: $Na_2HPO_4$ (30 g), $KH_2PO_4$ (15 g) $NH_4Cl$ (5 g), and NaCl (2.5 g) were added to 1 L of D.I. water and then autoclaved. Step 2: Glucose solution (20 wt %) was prepared and then micro-filtered using a Corning Filter System (0.22 μm CN). Step 3: $CaCl_2 \cdot 2H_2O$ (15 g) was added to 10 mL of D.I. water and then micro-filtered using a Corning Filter System (0.22 μm CN). Step 4: $MgSO_4 \cdot 7H_2O$ (24 g) was added to 100 mL of D.I. water and then micro-filtered using a Corning Filter System (0.22 μm CN). Step 5: Autoclaved LB medium. Step 6: Autoclaved D.I. water. After all the individual steps were prepared then the components were mixed into an autoclaved 1 L Fischer Brand bottle, as follows: Step 3 (0.1 mL) and Step 6 (800 mL) were added to the autoclaved bottle, then mixed. Then, Step 2 (10 mL), Step 4 (1 mL) and Step 5 (1 mL) were added and mixed. Finally, Step 1 (200 mL) was added to the solution and mixed.

The antimicrobial effectiveness of C12 treated silicone catheter segments is evident from data in Table 9 from the multi-log kill of Gram-negative and Gram-positive bacteria and *Candida albicans*. C12-2 is one preferred composition because of favorable biocompatibility results described herein. However, other amines that were used to treat silicone catheters also show favorable results.

Antimicrobial Effectiveness in Viscous Medium.

Briefly, this test involved placing untreated and C12-amine treated tubing segments (M-C12-3), respectively, in medium with laboratory prepared artificial saliva (LAS) of increasing viscosity followed by introduction of pathogen challenges. A feed level of 3 wt % produced a biocompatible composition (FIG. 24).

The principal constituent of WV LAS is sodium carboxymethylcellulose {Amaechi, 1998 #2}. FIG. 14 shows viscosity versus concentration for LAS (g/L). After incubation for 24 h, aliquots are removed and plated to assess pathogen concentration. Images for test results that demonstrate the influence of viscosity on antimicrobial effectiveness are shown in FIG. 15 for G(−) *Pseudononas aeruginosa*, FIG. 16 for (G−) *Escherichia coli*, and FIG. 17 for (G−) *Klebsiella aerogenes*. A typical pathogen challenge was $10^5$ CFU/mL. Generally, 5 log kill (99.999%) was

TABLE 9

Shake flask test results for listed pathogens against C12 and C16 treated medical grade silicone catheters. Simulated normal urine was purchased from Carolina Biological Supply Co. (Burlington, NC) and sterilized using a Corning micro-filtering system (0.22 μm). Artificial saliva (15, 25, 53 and 138 cP) was made from a solution of PBS and carboxymethyl cellulose (average M.W. 90 kDa), then autoclaved for sterilization. Superscripts indicate test medium: B = PBS, S = artificial saliva and U = simulated urine, M = M-9 medium.

| Pathogen/Gram(+/−) | WV Treatment* | | | | | |
|---|---|---|---|---|---|---|
| | C12-2 | C12-2.5 | C12-3 | C12-4 | C12-6 | C12-8 |
| | | | Log Reduction | | | |
| E. coli/G− | $>3^{B,U}$ | $>3^U$ | $>3^S$ | | | $>3^B$ |
| Candida albicans (spp)/Fungi | $>3^B 3^U$ | $>3^U$ | | | | |
| P. aeruginosa/G− | | | $>3^S$ | | | |
| K. aerogenes/G− | | | $>3^S$ | | | |
| S. epidermidis/G+ | | | | | | $>3^B$ |
| S. epidermidis (methicillin resistant)/G+ | | | | $>3^B$ | $>3^B$ | $>3^B$ |
| S. aureus/G+ | $<1^M$ | $1^M$ | | | | $>3^B$ |
| K. pneumoniae/G− | $>3^B$ | | | | | |

| Pathogen/Gram(+/−) | WV Treatment** | | | | | | |
|---|---|---|---|---|---|---|---|
| | C14-2 | C14-3 | C14-4 | C14-5 | C14-6 | C14-7 | C14-8 | C14-9 |
| | | | | Log Reduction | | | | |
| E. coli/G− | | | | | | | | |
| S. aureus/G+ | $<1^M$ | $1^M$ | $<2^M$ | | | | | |

| Pathogen/Gram(+/−) | WV Treatment** | | | | | | |
|---|---|---|---|---|---|---|---|
| | C16-2 | C16-3 | C16-4 | C16-5 | C16-6 | C16-8 | C16-10 | C16-12 |
| | | | | Log Reduction | | | | |
| E. coli/G− | | | | $3^B$ | $>3^B$ | $>3^B$ | $>3^B$ | |
| S. aureus/G+ | $<1^M$ | $<2^M$ | $<3^M$ | | | | | |

| Pathogen/Gram(+/−) | WV Treatment*** | |
|---|---|---|
| | C12-2H-1.5 | C12-2H-2.0 |
| | Log Reduction | |
| E. coli/G− | $>3^B$ | $>3^B$ |

*N,N-dimethyldodecylamine (C12) was used for treatment of medical grade silicone catheter segments.
**N,N-dimethylhexadecylamine (C16) was used for treatment of medical grade silicone catheters segments.
***Dodecylamine (C12-2H) was used for treatment of medical grade silicone catheters segments.

obtained. Table 9 summarizes test results for these pathogens. As shown herein, biocidal action by contact with treated medical grade silicone catheters is not impeded by viscosities mimicking human saliva and mucus.

(4) Investigations of Stability

The same shake flask test was utilized to establish the stability of medical grade silicone treated with C12 amine (a) in simulated urine, (b) on storage, and (c) after exposure to growth medium. FIG. 18 below contains images from the shake flask test in simulated normal urine spanning a 4-week period. M-C12-1.5 and M-C12-2.5 were tested against wild type $E.$ $coli$ with an initial concentration of $10^5$ cfu/mL. Moreover, stability of silicone segment catheters with the same compositions in urine was investigated against $Candida$ $albicans$ for 1 week and presented in FIG. 19. M-C12-2.5 showed excellent stability (5 log reduction) against $E.$ $coli$ and $Candida$ $albicans$ for 4 weeks and 1 week respectively. On the other hand, the reduction of antimicrobial activity of M-C12-1.5 against $E.$ $coli$ and $Candida$ $albicans$ was noticed after 2 weeks and 1 week respectively.

To instigate the stability of modified silicone M-C12-1.5 and M-C12-2.0 on storage, the treated catheter segments were kept in a plastic bag at room temperature (25° C.) for a 4-week period. The antibacterial activity of the samples against wild $E.$ $coli$ was evaluated every week using shake flask test. FIG. 20 reveals that stability of M-C12-2.0 in a package was not changed for 4 weeks, while activity of M-C12-1.5 showed some inconsistent results for the same time period.

In addition, the stability of M-C12-1.5, M-C12-2.0, and M-C12-2.5 was evaluated after exposure to cell growth medium. C12 modified medical grade silicone catheter segments used in cytotoxicity test were kept in cell culture medium (FM, ScienceCell catalog #2301) for 3 weeks prior to the antimicrobial test. After that, the samples were washed with DI water, immersed in PBS solution and then sterilized with UV radiation overnight. The antibacterial activity of the tested samples was challenged against wild $E.$ $coli$ with initial concentration of $2.3 \times 10^5$ cfu/mL. The images presented in FIG. 21 were used for establishing of the log-reduction for M-C12-1.5, M-C12-2.0, and M-C12-2.5 that corresponded to <1 log, 2 log, and 1 log respectively (Table 10). This result indicates that silicone modified with C12 amine after treatment with cell growth medium for 3 weeks at room temperature has lost some antimicrobial activity.

TABLE 10

Log reduction after exposure of treated medical grade silicone segments to cell culture medium.

| Treated silicone segments | Log reduction after exposure to cell culture medium | |
|---|---|---|
| | 24 h exposure | 3 weeks exposure |
| M-C12-1.5 | <1 Log | <1 Log |
| M-C12-2.0 | 5 Log | 2 Log |
| M-C12-2.5 | 5 Log | 1 Log |

The antibacterial activity of medical grade silicone segments M-C12-1.5, M-C12-2.0, and M-C12-2.5 was re-evaluated after they were used in the Minimal Essential Media (MEM) Elution test designed to determine the cytotoxicity of extractable. The treated catheter segments were extracted in cell culture medium for 24 h Antibacterial activity was tested against $E.$ $coli$ with initial concentration of the pathogen $2.3 \times 10^5$ cfu/mL. The images presented in FIG. 22 revealed that M-C12-1.5 showed the reduction of activity (<1 Log) while the activity of M-C12-2.0 and M-C12-2.5 was unchanged. For both compositions log reduction corresponded to 5 (Table 10). These results indicate that interaction of M-C12-2.0 and M-C12-2.5 with cell culture medium for a long period of time (up to 3 weeks) leads to the decrease of their antibacterial activity while short period contact (24 h) does not influence on the activity of the modified silicone catheter segments.

(5) Biocompatibility a. In Vitro Biocompatibility

Cytotoxicity of C12 treated Bard silicone Foley catheters (Fr. 22) toward mammalian cells was investigated as a measure of biocompatibility. The cell lines employed in this study include Human Dermal Fibroblast cells (HDFs), Astrocyte cells and Schwann cells. The cytotoxicity assay followed ISO 10993-5, the entire contents of which are hereby incorporated by reference, a test that determines if the sample leaches toxic substances. C12 treated catheter segments were extracted in growth medium for 24 h. Bard silicone Foley catheters segments (1 cm length) were cut to half pipes in longitudinal direction. The total surface area of each half pipe sample was 2.4 cm². In a typical experiment, 6 pieces of half pipe sample were extracted in 4.5 mL growth medium at 37° C. for 24 h. Extraction ratio was 3.2 cm$^{-1}$ (surface to volume). After removing the samples, the growth medium extract was added to a 70% confluent layer of mammalian cells and incubated for 48 h (37° C., 5% $CO_2$). The morphology and density of the mammalian cells were investigated to evaluate the cell compatibility of the samples. According to ISO 10993-5, reduction of cell viability by more than 30% is considered a cytotoxic effect.

EXPERIMENTAL

Materials: Human Dermal Fibroblast cells (HDFs), Astrocyte cells and Schwann cells were purchased from ATCC®, Manassas, Va. Fibroblast Medium (FM) complete kit was purchased from ScienCell™. The FM complete kit consists of 500 ml of base medium, 10 ml of fetal bovine serum (FBS), 5 ml of fibroblast growth supplement (FGS), and 5 ml of penicillin/streptomycin solution (P/S). Neural cell growth medium was prepared by mixing 500 mL DMEM/F-12 (ThermoFisher), 56 mL FBS (ThermoFisher) and 5.6 mL P/S solution (10000 U/mL Gibco™). AlamarBlue® reagent was obtain from Bio-Rad Laboratories.

Cytotoxicity test: The in vitro ISO 10993-5 (extraction) test was used for amine treated catheter segments to detect release of harmful species for mammalian cells. In detail: (1) Amine-treated catheter segments (and untreated controls) were extracted in cell growth medium (FM for HDFs; neural cells growth medium for Astrocyte cells and Schwann cells) at 37° C. for 24 hours. The surface to volume extraction ratio was 3 cm$^{-1}$; (2) Separately, mammalian cells were grown to 70-80% confluence in a 12-well polystyrene plate; (3) The cell growth medium was replaced with the extraction medium (or blank cell growth medium as control) followed by incubation at 37° C. with 5% $CO_2$ for 48 h. Triplicates were made for each sample; (4) Cell morphology after 24- and 48-h incubation was examined by optical microscopy. Cell viability after 48-hour incubation was measured by using AlamarBlue® assay.

AlamarBlue® assay: AlamarBlue® assay allowed for the quantitatively measurement of cell death after extraction medium was introduced. After 48-h incubation, extraction medium in the 12-well plates was replaced by 10% (v/v) alamarBlue reagent mixed with fresh cell growth medium. The cells and 10% alamarBlue reagent were incubated at 37°

C. for 3 h. For each test, 10% alamarBlue was also incubated without cells as blank. After incubation, 10% alamarBlue reagent was transferred to a 96-well plate (100 µL/well) to obtain fluorescence intensity (excitation/emission: 530/590 nm). Triplicates was made for each well of the 12-well plates. Cell viability was calculated via Eq. 7.

$$\text{Cell viability} = \frac{Fluorescence_{sample} - Fluorescence_{blank}}{Fluorescence_{control} - Fluorescence_{blank}} \times 100\%. \quad \text{Eq 7}$$

Results and Discussion

Results of ISO 10993-5 assays are shown in FIG. 23. HDFs, astrocytes and Schwann cells were selected to evaluate the cytotoxicity of amine treated silicone catheters. Viability of HDFs was about 100% for C12-1.5 (101%±1%), C12-2 (101%±1%) and C12-2.5 (104%±1%) coatings. With increasing C12 feeding weight percentage, viability decreased to 92%±3% for C12-3, 84%±1% for C12-3.5, 42%±15% for C12-4 and 7%±1% for C12-6. Similarly, viability of Schwann cells was above 90% for C12-1.5 (90%±5%), C12-2 (102%±12%) and C12-2.5 (98%±3%) but decreased to 75%±4% for C12-3. Interestingly, viability of astrocytes remained high for all the tested compositions, which are 97%±6% for C12-1.5, 94%±6% for C12-2, 96%±11% for C12-2.5 and 98%±12% for C12-3.

As a summary, no sign of cytotoxicity was obtained for C12-1.5, C12-2 and C12-2.5 while C12-3, had slightly decreased viability for HDF and Schwann cells, can be considered as non-cytotoxicity because >70% viability is "PASS" in ISO 10993-5 document. These in vitro test results provide a guide for biocompatibility.

Zone of inhibition (ZOI) for C12 showed that there was no ZOI for C12-1.5, C12-2 and C12-4. However, for C12-6 there was a ZOI. The results were interpreted in terms of a threshold for leaching.

Results from animal studies are described below (in vivo).

Representative images for ISO 10993-5 tests are shown in FIG. 24. Similar to the growth medium control, no noticeable cell death or change of morphology was observed for both M-C12-1.5 and M-C12-2 treated silicone catheter segments for HDFs, astrocytes and Schwann cells (FIG. 24 A1-A3, B1-B3, C1-C3). In contrast, most cells were killed by latex positive control samples within 48 hours (FIG. 24 A4, B4 and C4). According to ISO 10993-5 test, "not more than 50% of the cells are round, devoid of intracytoplasmic granules, no extensive cell lysis; not more than 50% growth inhibition observable" is considered "PASS" in this test. Thus, both M-C12-1.5 and M-C12-2 treated silicone catheter segments exceeded the requirement to pass ISO 10993-5 in vitro cytotoxicity test.

Additional cytotoxicity tests were carried out. A monolayer of cells is exposed to an extraction solvent containing amine treated silicone samples at a ratio of approximately 3.0 cm²/mL. After a 24 h incubation period, the cells are then observed for any cell destruction and overall cytotoxicity. Scoring was along a Pass/Fail rating of 0-4, with 0-2 being a pass and 3-4 being a fail rating. Table 11 below indicates a rating of 0 for the two compositions of the WV treated silicone catheter segments sent for testing (1.5 wt % and 2.0 wt %).

Controls are also indicted below to ensure purity of the results.

In Vivo Biocompatibility

In vivo studies were carried out to study the potential toxicity of WV amine treated coatings in the living body, which is far more complex than the cell culture system. All in vivo studies were conducted at an AAALAC International accredited facility and is registered with the United States Department of Agriculture, with an approved Animal Welfare Assurance on file with the National Institutes of Health, Office for Laboratory Animal Welfare (OLAW) and approved by the Institutional Animal Care and Use Committee (IACUC).

TABLE 11

Cytotoxicity results for amine treated silicone catheter segments. Identification 1 is M-C12-1.5, 2 is M-C12-2, 3 is M-C12-2.5, 4 is M-C12-3.0 treated silicone catheter segments. M-C12-1.5 and M-C12-2.0 were tested twice.

| | Results | Scores | | | | | Amount Tested/ Extraction Solvent | |
| --- | --- | --- | --- | --- | --- | --- | --- | --- |
| Identification | Pass/Fail | #1 | #2 | #3 | Average | Extraction Ratio | Amount | |
| 1 | Pass | 0 | 0 | 0 | 0 | 3 cm²/mL | 47.8 cm²/15.9 mL | |
| 2 | Pass | 0 | 0 | 0 | 0 | 3 cm²/mL | 47.8 cm²/15.9 mL | |
| 3 | Pass | 2 | 2 | 2 | 2 | 3 cm²/mL | 47.8 cm²/15.9 mL | |
| 4 | Fail | 4 | 4 | 4 | 4 | 3 cm²/mL | 47.8 cm²/15.9 mL | |
| 1 | Pass | 0 | 0 | 0 | 0 | 3 cm²/mL | 47.8 cm²/15.9 mL | |
| 2 | Pass | 0 | 0 | 0 | 0 | 3 cm²/mL | 47.8 cm²/15.9 mL | |

Controls:

| | Scores | | | | | Amount Tested/ Extraction Solvent | |
| --- | --- | --- | --- | --- | --- | --- | --- |
| Identification | #1 | #2 | #3 | Average | Extraction Ratio | Amount | |
| Negative Control - Polypropylene Pellets | 0 | 0 | 0 | 0 | 0.2 g/mL | 4 g/20 mL | |
| Media Control | 0 | 0 | 0 | 0 | N/A | 20 mL | |
| Positive Control - Latex Natural Rubber | 4 | 4 | 4 | 4 | 0.2 g/mL | 4 g/20 mL | |

Acute systemic toxicity test (ISO 10993-11 (the entire contents of which are hereby incorporated by reference)) in mice (*Mus musculus*, Outbred albino). Purpose: to evaluate acute systemic toxicity of a test article extract following a single intravenous or intraperitoneal injection in mice. Mice have historically been used to evaluate biomaterial extracts. The use of albino mice injected with a single intravenous (IV) or intraperitoneal (IP) dose of test article extract or control blank have been suggested by ISO for evaluation of medical plastics. Coated tube segments (test article) were immersed in 0.9% sodium chloride (SC) or sesame oil (SO) (ratio: 3 $cm^2$/ma) for 72 h at 50° C. to obtain the extract. For control articles, the extraction vehicle was prepared in the same way and at the same time as the test article extract but without the test article. Animals were randomly assigned to the coated test group and control group, 5 mice per group. No particular sex was prescribed for this test; females were nulliparous and nonpregnant. At injection, body weight range was 19-22 grams. Prior to dosing, the mice were identified and weighed. Five animals each was injected with the appropriate test extract at a dose of 50 mL/kg. Five mice were similarly injected with the corresponding extraction vehicles as control. Mice were observed for adverse reactions immediately after dosing, and at 4, 24, 48 and 72 h after injection. The animals were weighed daily for 3 days after dosing. Any animal found dead would be subjected to a gross necropsy of the viscera and histopathology if deemed necessary. If during the observation period none of the mice treated with the test extract show a significantly greater reaction than the corresponding control mice, then the test sample meets the test requirements.

Intracutaneous Study (ISO 10993-10 (the entire contents of which are hereby incorporated by reference)) in Rabbits (*Oryctolagus cuniculus*, New Zealand White). Purpose: to evaluate the local dermal irritation of a test article extract following intracutaneous injection in rabbits. The intracutaneous injection test in rabbits is specified in the current ISO testing standards and has been used historically to evaluate biomaterial extracts. Coated catheter segments (test article) was immersed in 0.9% sodium chloride or sesame oil (ratio: 3 $cm^2$/1 ml) for 24 h to obtain extracts. For control article, the extraction vehicles were prepared in the same way and at the same time as the test article extracts but without the test article and served as controls. Animals were randomly assigned to the coated test group and control group, 3 rabbits (young adult) per group. No particular sex was prescribed for this test; females were nulliparous and nonpregnant. Body weight range was 2.0 kg or greater at selection. Prior to treatment each animal was identified and weighed. Within a 4 to 18 h period before treatment, each rabbit was clipped free of fur from the back and both sides of the spinal column to yield a sufficient injection area. A 0.2 mL dose of the appropriate test article extract was injected by the intracutaneous route into five separate sites on the right side of the back of each rabbit. Similarly, the corresponding control was injected on the left side of the back of each rabbit. Injections were about 2 cm apart. The appearance of the injection sites was noted immediately after injection. Observations for erythema and edema were noted for each injection site at 24, 48 and 72 h after injection. Reactions were scored on a 0 to 4 basis (0: No erythema/edema; 1: Very slightly erythema/edema; 2: Well-defined erythema/edema; 3: Moderate erythema/edema; 4: severe erythema/edema). Other adverse changes at the injection sites would be noted. To evaluate the reaction, all erythema grades and edema grades (24, 48 and 72 hours) separately for each test and control for each individual animal was calculated by dividing each of the totals by 15 (3 scoring time points×5 sites). The overall mean for each test and control was determined by adding the scores for the 3 animals and divide by 3. The difference between the overall mean score of the test article extracts and corresponding control extracts was calculated by subtracting the overall mean score for the control from the overall mean score for the test article extract. The requirements of the test are met if the difference between the test article extract overall mean score and the corresponding control overall mean score is 1.0 or less.

Maximization Sensitization Test (ISO 10993-10 (the entire contents of which are hereby incorporated by reference)) in Guinea Pig (*Cavia porcellus*, Hartley). Purpose: to evaluate the potential of the test article to cause delayed dermal contact sensitization. The Hartley albino guinea pig has been used historically for sensitization studies. The guinea pig is believed to be the most sensitive animal model for this type of study. Coated catheter segments (test article) were immersed in 0.9% sodium chloride or sesame oil (ratio: 3 $cm^2$/1 ml) at 50° C. for 24 hours to obtain extracts. For control article, the extraction vehicles were prepared in the same way and at the same time as the test article extracts but without the test article and will serve as controls. 15 guinea pigs (young adult) were randomly assigned to the coated test group (10 animals) and control group (5 animals). No particular sex was prescribed for this test; females were nulliparous and nonpregnant. Body weight range was 300-500 grams at study initiation. On the first day of treatment, animals were weighed. The fur from the dorsoscapular area was removed. There were two induction phases and one challenge phase. In the Phase I (Intradermal induction phase), 0.1 mL test article extract or control extract vehicle was intradermal injected. In the phase II (topical induction phase): At 6 days after completion of the intradermal induction phase, test article extract or control extract vehicle was topically applied to the intrascapular region of each animal using a patch of area approximately 8 $cm^2$ (absorbent gauze), so as to cover the intradermal injection sites. Challenge phase: At 14 days after topical induction phase, challenge animals with extract for 24 hours. NAMSA observed the appearance of the challenge skin sites of the coated and uncoated extract inducted animals at 24+/−2 hours and 48+/−2 hours after removal of the challenge dressings. Skin reaction (erythema, edema, and swelling) was graded on a 0 to 3 basis (0: No visible change; 1: Discrete or patchy erythema; 2: Moderate and confluent erythema; 3: Intense erythema and swelling). Grade of 1 or greater indicates sensitization, provided that grade of less than 1 was observed on the control animals. If grades of 1 or greater were noted on control animals, then the reactions of test animals that exceeded the most severe control reaction would be considered to be due to sensitization.

Muscle Implantation Study (ISO 10993-6 (the entire contents of which are hereby incorporated by reference)) in Rabbits (*Oryctolagus cuniculus*, New Zealand White). Purpose: to evaluate the local tissue response to the test article implanted in muscle tissue in rabbits. The rabbit is suggested as an appropriate animal model for evaluating polymer materials by the current ISO testing standards. The muscle tissue has been used historically because the response to implanted material is easily graded and compared to a known negative control material. Five female New Zealand White rabbits were used. No particular sex was prescribed for this test; females were nulliparous and nonpregnant. Body weight range was 2.5 kg or greater at selection. Under sterile and anesthetized condition, the coated catheter segments and high density polyethylene (HDPE, negative control) were implanted in the paravertebral muscle tissue of rabbits. The coated samples were implanted at left side and HDPE was implanted at right side. Four coated and four uncoated samples were implanted in each animal. Observation and record were conducted every day after implantation. The implantation side of the skin was evaluated and imaged to measure abnormal responses, such as bleeding, swelling, necrosis, and discharge. The rabbits were euthanatized after 4 weeks. Gross observations were made at necropsy, and specimens were collected for microscope observations. Tissue samples with catheter segments were preserved in 10% formaldehyde, embedded in paraffin, sectioned, and stained for routine Hematoxylin and eosin (HE) stain. Attention was paid to any anatomical and histopathological changes, irritations, toxicity to the muscle tissues. Comparisons including the reaction of surrounding tissues, the thickness of the fibrosis capsule space, the existence of inflammatory cells and other cells, as well as other abnormal states at the interface of catheter segments and tissues were done between uncoated catheter segments and HDPE control.

Results and Discussion

Acute systemic toxicity test (ISO 10993-11 (the entire contents of which are hereby incorporated by reference)) in mice (*Mus musculus*, Outbred albino). All the animals were clinically normal throughout the study for both M-C12-1.5 and M-C12-2 treated catheter segment samples. No mortality was observed during the tests. All the animals gained weight throughout the course of the studies. There was no mortality or evidence of systemic toxicity from the extracts injected into mice. Each test article extract met the requirements of the study. for both M-C12-1.5 and M-C12-2 samples.

Intracutaneous Study. (ISO 10993-10 (the entire contents of which are hereby incorporated by reference)) in Rabbits (*Oryctolagus cuniculus*, New Zealand White). For M-C12-1.5 treated catheter segment sample, the score was 0.0 for 0.9% sodium chloride and 0.1 for sesame oil. For M-C12-2 treated catheter segment sample, the score was 0.0 for both 0.9% sodium chloride and sesame oil. Both samples met the requirement (score of 1.0 or lower) for this test.

Maximization Sensitization Test (ISO 10993-10) in Guinea Pig (*Cavia porcellus*, Hartley). For M-C12-2 treated catheter segment samples, the score was 0 for both 0.9% sodium chloride and sesame oil. M-C12-2 treated catheter segment samples met the requirement for this test. M-C12-2 treated catheter segments showed no evidence of causing delayed dermal contact sensitization in the guinea pig. The test article was not considered a sensitizer in the guinea pig maximization test.

Muscle Implantation Study. (ISO 10993-6 (the entire contents of which are hereby incorporated by reference)) in Rabbits (*Oryctolagus cuniculus*, New Zealand White). The macroscopic reaction for M-C12-2 treated catheter samples was not significant as compared to the negative control article. Microscopically, M-C12-2 caused a minimal or no reaction in the tissue as compared to the negative control article. M-C12-2 treated catheter segment samples met the requirement for this test.

a. In Vitro Biocompatibility

Cytotoxicity of C12 treated Bard silicone Foley catheters (Fr. 22) toward mammalian cells was investigated as a measure of biocompatibility.

For comparison, commercially available Bard LUBRISIL™ and Medline SILVER TOUCH™ catheters were tested by the same protocols.

The cell lines employed in this study include Human Dermal Fibroblast cells (HDFs), Astrocyte cells and Schwann cells. The cytotoxicity assay followed ISO 10993-5, a test that determines if the sample leaches toxic substances. C12 treated catheter segments were extracted in growth medium for 24 h. Bard silicone Foley catheters segments (1 cm length) were cut to half pipes in longitudinal direction. The total surface area of each half pipe sample was 2.4 cm². In a typical experiment, 6 pieces of half pipe sample were extracted in 4.5 mL growth medium at 37° C. for 24 h. Extraction ratio was 3.2 cm$^{-1}$ (surface to volume). After removing the samples, the growth medium extract was added to a 70% confluent layer of mammalian cells and incubated for 48 h (37° C., 5% $CO_2$). The morphology and density of the mammalian cells were investigated to evaluate the cell compatibility of the samples. According to ISO 10993-5, reduction of cell viability by more than 30% is considered a cytotoxic effect.

EXPERIMENTAL

Materials: Human Dermal Fibroblast cells (HDFs), Astrocyte cells and Schwann cells were purchased from ATCC®, Manassas, Va. Fibroblast Medium (FM) complete kit was purchased from ScienCell™. The FM complete kit consists of 500 ml of base medium, 10 ml of fetal bovine serum (FBS), 5 ml of fibroblast growth supplement (FGS), and 5 ml of penicillin/streptomycin solution (P/S). Neural cell growth medium was prepared by mixing 500 mL DMEM/F-12 (ThermoFisher), 56 mL FBS (ThermoFisher) and 5.6 mL P/S solution (10000 U/mL Gibco™). AlamarBlue® reagent was obtain from Bio-Rad Laboratories.

Cytotoxicity test: The in vitro ISO 10993-5 (extraction) test was used for amine treated catheter segments to detect release of harmful species for mammalian cells. In detail: (1) WV amine-treated catheter segments (and untreated controls) were extracted in cell growth medium (FM for HDFs; neural cells growth medium for Astrocyte cells and Schwann cells) at 37° C. for 24 hours. The surface to volume extraction ratio was 3 cm$^{-1}$, (2) Separately, mammalian cells were grown to 70-80% confluence in a 12-well polystyrene plate. (3) The cell growth medium was replaced with the extraction medium (or blank cell growth medium as control) followed by incubation at 37° C. with 5% $CO_2$ for 48 h. Triplicates were made for each sample. (4) Cell morphology after 24- and 48-h incubation was examined by optical microscopy. Cell viability after 48-hour incubation was measured by using AlamarBlue® assay.

Results: FIGS. 25 and 26 show a comparison of C12-2 cytocompatibility with two commercially available silver-eluting urinary catheters, Bard Lubrisil and Medline Silver Touch.

Concerns for existing silver technology include cytotoxicity of silver nanoparticles to human fibroblast cells, silver nanoparticles delayed wound healing, and toxicity is not determined by silver content but the level of silver leaching.

Summary: C12-2, Bard Lubrisil and Medline Silver Touch had strong antimicrobial effectiveness against an *E. coli* challenge (ASTM E2149). C12-2 and Bard Lubrisil passed ISO 10993-5, a test that determines if the sample leaches toxic substances, but Medline Silver Touch failed this cytocompatibility test.

Figure 28:
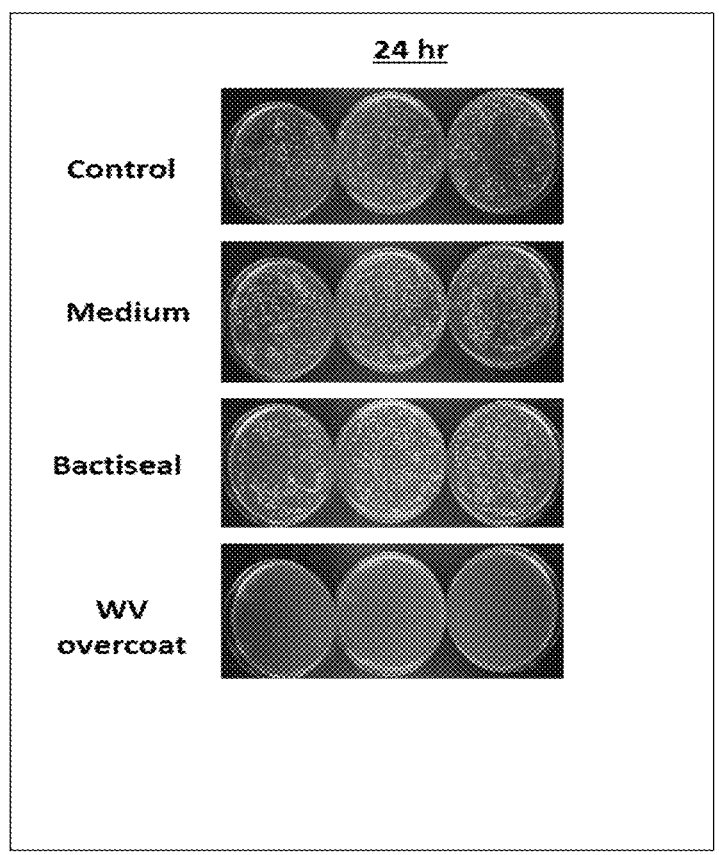

Bactiseal ventricular shunt tubing compared with C12-2. FIG. 28 provides a comparison of the product C12-2 with Bactiseal ventricular drain catheter (impregnated with Rifampin and Clindamycin). (Antimicrobial Procedure ASTM E2149). Importantly, Bactiseal has no antimicrobial effectiveness against *Candida albicans* while C12 Effects a>3 log reduction. Tests were done after immersion for 24 hr.

Cytotoxicity tests against mouse fibroblast cells using treated silicone catheter sections were carried out at a GLP lab. C12-2.5, C12-3, C14-2.5, C14-3, C16-2.5, and C16-3 examples were tested. Here, "C12", "C14", "C16" correspond to the amines in Table 1, and the "-2.5" and "-3" correspond to the weight percent of the amine used in the feed to treat the medical grade silicone catheter. The purpose of the study was to determine the potential of a test article extract and its corresponding dilutions to cause cytotoxicity. The study was based on the requirements of the International Organization for Standardization 10993-5, Biological evaluation of medical devices—Part 5: Tests for in vitro cytotoxicity. The test was performed in compliance with the ISO 13485 standard, with the test method accredited to the ISO 17025 standard. Silicone tubing segments from urinary catheters (22 Fr), which were cut to half pieces lengthwise and treated with amine as described. The samples were 1 cm long and translucent. Surface area was 2.4 cm2 per piece. Mammalian cell culture monolayer consisting of L-929 mouse fibroblast cells free from *mycoplasma* (ECACC Catalog No. 85103115) was used. In vitro mammalian cell culture studies have been used historically to evaluate cytotoxicity of biomaterials and medical devices. L-929 mouse fibroblast cells were propagated and maintained in flasks containing 1×MEM at 37° C. with 5% carbon dioxide ($CO^2$). For this study, cells were seeded in 10 $cm^2$ cell culture wells and incubated at 37° C. in the presence of 5% $CO_2$, to obtain subconfluent monolayers of cells prior to use. Aseptic procedures were used in the handling of the cell cultures.

Thirty-one test articles were included in the preparation and were not cut or subdivided. A single preparation of the test article and each of the controls were subjected to the extraction conditions: extraction ratio $3\ cm^2$:1 mL, combined surface area of test samples 74.4 $cm^2$, volume of vehicle 25 mL, extraction conditions 37° C. for 72 hours. The extracts were continuously agitated during extraction. The 1×MEM extraction method was conducted in the presence of serum to optimize extraction of both polar and non-polar components. The test article remained visually unchanged following the extraction process. The extracts were tested less than 4 hours following extraction. The extracts were not centrifuged, filtered, or otherwise altered prior to dosing. Following extraction, a portion of the test article extract was maintained undiluted (100%) and the following dilutions were prepared with 1×MEM: 50%, 25%, 12.5%, 6.25%, and 3.13%. All dilutions were achieved via a serial dilution method from the undiluted test extract. All test article extract dilutions were pink and clear with no particulates. Triplicate culture wells were selected which contained a subconfluent cell monolayer. The growth medium contained in the triplicate cultures was replaced with 2.0 mL of the undiluted test extract (100%) or a test extract dilution (50%, 25%, 12.5%, 6.25%, or 3.13%) in each well. Similarly, the growth medium in triplicate 10 $cm_2$ wells was replaced with 2.0 mL of the reagent control, the negative control, and the positive control extracts. The wells of each plate were labeled with the appropriate lab number or control and the replicate number. Each plate was labeled with the test code and the dosing date. The undiluted test article extract, test article extract dilutions, negative control, positive control, and reagent control wells were incubated at 37° C. in 5% CO2 for a total of 48 hours. Following incubation, the cells were examined microscopically (100×) to evaluate cellular characteristics and percent lysis. The undiluted test article extract and test article extract dilutions were evaluated independently.

Results

No cytotoxicity or cell lysis was noted in any of the test wells for the undiluted test article extract or in any of the test wells for the C12-2.5, C12-3, C14-2.5, C14-3, C16-2.5, and C16-3 exemplary extract dilutions. No pH shift was observed at 48 hours. The reagent control, negative control, and positive control performed as anticipated.

CONCLUSION

The undiluted (100%) test article extract and all of the corresponding test article extract dilutions (50%, 25%, 12.5%, 6.25%, and 3.13%) for the C12-2.5, C12-3, C14-2.5, C14-3, C16-2.5, and C16-3 exemplary samples showed no evidence of causing cell lysis or toxicity. The undiluted test article extract and all corresponding test article extract dilutions met the requirements of the test since the grades were less than a grade 2 (mild reactivity).

Additional Performance Data

A.1 Materials used in the studies below are described.

N,N-dimethyltetradecylamine $(CH_3(CH_2)_{13}N(CH_3)_2$, Molecular Weight 241.46, CAS Number 112-75-4) 90%, (sometimes referred to herein as "C14") made by TCI of America, Portland, Oreg., purchased from Fisher Scientific Company, Nazareth, Pa.;

N,N-Dimethyldodecylamine $(CH_3(CH_2)_{11}N(CH_3)_2$, Molecular Weight 213.40, CAS Number 112-18-5), (sometimes referred to herein as "C12")>96%, made by TCI of America, Portland, Oreg., purchased from Fisher Scientific Company, Nazareth, Pa.;

Ethanol, ($CH_3CH_2OH$, Molecular Weight 46.07, CAS Number 64-17-5) Lab Grade, 95% denatured w/IPA and methanol, FSE, purchased from Fisher Scientific Company, Nazareth, Pa.;

Simulated urine (normal). Contents are water (92.33%), glycerol (7.64%), and sodium hydroxide (0.03%) was purchased from Carolina Biological Supply Company, Burlington, N.C.;

M9 Medium: M-9 Minimal Growth Medium Preparation (M-9). M-9 minimal growth media is a growth media used for specific bacteria strains that require salt additives for culturing purposes. Specifically, *Staphylococcus aureus* requires such a medium in order to conduct the E2149 Antimicrobial Test. The preparation of the M-9 was carried out in a multistep procedure using a level 2 bio-safety hood to ensure sterilization. Step 1: $Na_2HPO_4$ (30 g), $KH_2PO_4$ (15 g) $NH_4Cl$ (5 g), and NaCl (2.5 g) were added to 1 L of deionized (D.I.) water and then autoclaved. Step 2: Glucose solution (20 wt %) was prepared and then micro-filtered using a Corning Filter System (0.22 µm CN). Step 3: $CaCl_2.2H_2O$ (15 g) was added to 10 mL of D.I. water and then micro-filtered using a Corning Filter System (0.22 µm CN). Step 4: $MgSO_4\cdot 7H_2O$ (24 g) was added to 100 mL of D.I. water and then micro-filtered using a Corning Filter System (0.22 µm CN). Step 5: Autoclaved LB medium. Step 6: Autoclaved D.I. water. After all the individual steps were prepared then the components were mixed in an autoclaved 1 L Fischer Brand bottle. Components from steps are: 0.1 mL (Step 3) and (800 mL) (Step 6) were added to the autoclaved bottle, then mixed. Then, 10 mL (Step 2), 1 mL (Step 4), and 1 mL (Step 5) were added and mixed. Finally, 200 mL (Step 1) was added to the solution and mixed. (Reference: *ACS Appl. Mater. Interfaces* 2019, 11, 23, 20699-20714)

Phosphate buffered saline (PBS) was prepared in lab from $NaH_2PO_4$, $Na_2HPO_4$, and NaCl purchased from Carolina Biological Supply Company, Burlington N.C.

HCl and KOH used for pH adjustment were purchased from Fisher Scientific, Fair Lawn N.J.

Bardex® Lubri-Sil® I.C. Foley Catheter French, size 20 fr (sometimes referred to herein as "Bardex® Lubri-Sil®" or "Lubri-Sil®") was purchased from Health Products For You (HPFY), Brookfield, Conn.;

Bardex® All-Silicone Foley Catheter French, size 22 fr (sometimes referred to herein as "Bardex® All-Silicone" or "All-Silicone") was purchased from Health Products For You (HPFY), Brookfield, Conn.;

For antimicrobial testing and the like, the following bacterial strains were used

*Escherichia coli* (G−) K-12 (BSL-1);

*Escherichia coli* (Migula) Castellani and Chalmers (ATCC® 700928™), strain CFT073 [WAM2267], Biosafety level 2, https://www.atcc.org/products/all/700928.aspx;

*Candida albicans* (Robin) Berkhout (ATCC® 18804™). Strain: CBS 562 [572, CCRC 20512, CECT 1002, DBVPG 6133, IFO 1385, IGC 3436, JCM 1542, NCYC 597, NRRL Y-12983]. Biosafety Level 1. https://www.atcc.org/products/all/18804.aspx;

*Pseudomonas aeruginosa* (Schroeter) Migula (ATCC® 47085™). Strain: PAO. Biosafety level 2. https://www.atcc.org/products/all/47085.aspx;

*Pseudomonas aeruginosa* (Schroeter) Migula (ATCC® 10145™). Strain: CCEB 481, MDB strain BU 277, NCIB 8295, NCPPB 1965, NCTC 10332, NRRL B-771, R. Hugh 815. Biosafety level 2. https://www.atcc.org/products/all/10145.aspx;

*Klebsiella pneumoniae* subsp. *pneumoniae* (Schroeter) Trevisan (ATCC 10031). Strain: PCI 602, Biosafety level 2. https://www.atcc.org/products/all/10031.aspx;

*Klebsiella pneumoniae* subsp. *pneumoniae* (Schroeter) Trevisan (ATCC® 13883). Strain NCTC 9633 [NCDC 298-53, NCDC 410-68], Biosafety level 2, https://www.atcc.org/products/all/13883.aspx;

*Enterococcus faecalis* (Andrewes and Horder) Schleifer and Kilpper-Balz (ATCC 49533). Strain: UWH 1936, Biosafety level-2. https://www.atcc.org/products/all/49533.aspx;

*Staphylococcus aureus* subsp. *aureus* Rosenbach (ATCC® 29213™). Strain: Wichita, Biosafety level 2, https://www.atcc.org/products/all/29213.aspx;

*Proteus mirabilis* Hauser (ATCC 35659), Strain: LRA 08 01 73[API SA, DSM 6674], Biosafety level-2. https://www.atcc.org/products/all/35659.aspx.

A.2 Process for Preparing ABC-Silicone: To prepare the ABC-Silicone samples, Bardex® All-Silicone catheters (Fr. 22) were cut into 1-cm long sections, which sections were subsequently cut lengthwise into half-pipe segments. The segments were placed into a 3.0 wt % N,N-dimethyltetradecylamine ("C14") solution in ethanol preheated to 40° C., and stirred continuously for 1 h. After 1 h, the segments were removed, washed three times in deionized (DI) water, and stored in sterilized PBS at pH 7 under UV light in a biosafety cabinet prior to use.

A.3 Composition of ABC-Silicone: The composition of the ABC-Silicone was established using $^1$H-NMR spectroscopy. The amine was extracted from the ABC-Silicone and the weight percent was quantitatively determined based on a standard curve. A series of standards was prepared by dissolving 1, 4, 6, 8 and 10 mg N,N-dimethyltetradecylamine in 1 mL deuterated methanol ($CD_3OD$). $^1$H-NMR spectra of the standards were obtained. The 0.9 ppm peak for the methyl group distal to the dimethylamine end of the C14 molecule was selected, and the integral was set to 3 (as the methyl group has three protons). The 3.31 ppm peak for protons of deuterated methanol solvent was selected and integrated. The ratios of the respective integral values were obtained and used to prepare a calibration curve for the concentration of N,N-dimethyltetradecylamine.

To determine the amount of N,N-dimethyltetradecylamine in the ABC-Silicone segments, five untreated silicone segments were prepared and weighed, and then subjected to the process described in A.2 to prepare five ABC-Silicone "C14-3" segments. The ABC-Silicone C14-3 segments so-prepared were removed from PBS, dried with a Kimwipe and then gently shaken in 2 mL $CD_3OD$ at 37° C. overnight in a tightly closed vial, to completely extract the N,N-dimethyltetradecylamine from the ABC-Silicone segments into the $CD_3OD$. $^1$H-NMR spectra of 1-mL extract solutions were obtained, and the ratio of integral values of the $CH_3$ 0.9 ppm peak for extracted amine to the $CD_3OD$ 3.31 ppm peak were calculated and compared to the calibration curve.

In this way, the amount of N,N-dimethyltetradecylamine in the ABC-Silicone segments was determined. It was found that the amount of N,N-dimethyltetradecylamine in the ABC-Silicone segments could be precisely controlled by the process by adjusting, for example the weight percent of amine in the ethanolic solution. In the present example, using the total mass of the five untreated segments (836 mg) the weight percent (wt %) of N,N-dimethyltetradecylamine in the ABC-Silicone segments observed from quantitative $^1$H-NMR spectra was determined to be about 0.9 wt %.

In one study, a group of ABC-Silicone samples underwent γ-radiation sterilization at a third party site. The samples were returned and tested for antimicrobial effectiveness as described in A.4.2, ASTM "shake flask" test, E2149-01. There was no visual change and no detectable change in antimicrobial effectiveness indicating that ABC-Silicone is unaffected by sterilizing radiation.

All other studies were carried out on ABC-Silicone samples that were not treated with γ-radiation sterilization. Considering that the silicone-amine phase contains only ~1% amine, a negligible effect on the mechanical properties of the parent Bardex® All-Silicone catheter is expected after γ-=radiation sterilization. Similarly, a negligible effect on in vitro and in vivo biocompatibility is expected for ABC-Silicone catheters after irradiation sterilization.

A.4 Antimicrobial Testing:

A.4.1 ASTM E2149-01 "Shake Flask" Test for Antimicrobial Activity

A.4.1 A "shake flask" test per ASTM E2149 against clinically relevant microorganisms show the antimicrobial effectiveness of C14-3 against a range of pathogens associated with urinary tract infections, including a greater than 4 log reduction (99.99% kill for *E. coli*(G−) and the yeast *Candida albicans*. High percent kills were observed for *P. aeruginosa* (G−), *K. pneumoniae* (G−), *Enterococcus faecalis* (G+) and *S. aureus* (G+).

ASTM E2149-01, sometimes referred to herein as the "shake flask" test, tests for antimicrobial activity under dynamic conditions. A stock bacterial solution was cultured in sterile lysogeny broth (LB) growth medium from a single colony. For *Candida albicans*, the growth medium was yeast peptone dextrose (YPD). UV-Vis spectroscopy (600 nm) was used to establish the concentration of the stock bacterial solution. The stock solution was then used to inoculate sterilized flasks containing 20 mL PBS, M-9 Minimal Growth Medium, or Simulated Urine at pH ~7. The concentration was diluted with the designated medium to $10^5$ cfu/mL. ABC-Silicone segments and untreated Bardex® All-Silicone catheter segments were added to separate flasks of stock solution at an approximately 1.16 cm²/mL surface area to volume ratio. The medium along was also tested as a for control (data not shown). The flasks were subjected to gentle rotation at 37° C. for 24 h in an incubator-shaker. Afterwards, aliquots from each flask were removed, serially diluted, and plated on agar. The plates were incubated for 24 h or more at 37° C., and bacterial colonies were then counted to establish log reduction. Antimicrobial effectiveness of ABC-Silicone C14-3 against a range of pathogens associated with urinary tract infections is shown in Table 12.

TABLE 12

Antimicrobial activity of ABC-Silicone C14-3 and untreated Bardex ® All-Silicone against pathogen challenge measured by ASTM E2149-01 shake flask test.[a]

| Pathogen/Gram (+/−) | Percent Infections[b] (%) | ABC-Silicone C14-3 | | Untreated Bardex ® All-Silicone |
| --- | --- | --- | --- | --- |
| | | Log Reduction[c] | % Kill | % Kill[c] |
| E. coli (G−) K-12 | 23.90 | 4.3[B] | >99.99 | 0 |
| Candida albicans | 17.80 | >4[B] | >99.99 | 0 |
| P. aeruginosa (G−) | 10.3 | 0.8[B] | ~80 | 0 |
| K. pneumoniae (G−) | 10.1 | 5[B] | 99.999 | 0 |
| Enterococcus faecalis (G+) | 7.0 | 5[B] | 99.999 | 0 |
| S. aureus (G+) | 1.6 | 0.9[M9] | ~90 | 0 |
| Others | 29.3 | | | |

[a]Superscripts indicate test medium, both at pH ~7: [B]= PBS; [M9]= M-9 medium.
[b]Reviews for percent pathogens for UTIs give varying estimates. The estimates listed in this table are from Infect. Control Hosp. Epidemiology, 2016 37, 1288-1301 and Nat Rev Microbiol. 2015 13, 269-284.
[c]Log reduction for ABC-Silicone is based on growth for untreated Bardex All-Silicone. For example, if the bacterial growth for untreated Bardex All-Silicone results in 10⁵ cfu/mL and no colonies are found for ABC-Silicone, a calculation gives a 5 log kill (99.999%).

A.4.2 ASTM E2149-01 Stability in Simulated Urine at pH 4, 6 & 8

A.4.2 Antimicrobial testing for C14-3 ABC-Silicone and Bardex® Lubri-Sil® was conducted according to ASTM E2149-01, which tests for antimicrobial activity under dynamic conditions. After immersion in simulated urine (pH 4, 6 and 8, respectively) at 37° C. for 7 days, the antimicrobial efficacy of C14-3 ABC-Silicone and Lubri-Sil® samples were determined by ASTM E2149-01 shake flask test. A 5 log reduction (99.999% kill) against E. coli (strain K12) was observed for both C14-3 ABC-Silicone and Lubri-Sil® at pH 6 and 8. At pH 4, a 5 log reduction (99.999% kill) against E. coli (strain K12) was observed for C14-3 ABC-Silicone while a 3 log kill (99.9% kill) was found for Lubri-Sil®.

A.4.3 Kirby-Bauer Zone of Inhibition Test for Leaching

A.4.3 A zone of inhibition (ZOI) test was employed for C14-3 catheter segments to investigate possible leaching of an antimicrobial component. From imaging segments on a lawn of bacteria, C14-3 catheter segments do not show a detectable ZOI. This result and other studies of biocompatibility supported no detectable leaching from C14-3 catheter segments.

A.5 Biocompatibility. A range of ABC-Silicone samples was examined for antimicrobial effectiveness and biocompatibility. Appendix 1 preferentially reports evaluation data for C14-3 because this ABC-Silicone showed superior across the board performance.

A.5. Biocompatibility in vivo.

A.5.1,2 Animal studies. In vivo studies for biocompatibility described in Appendix 1 are presented for the C12-3 ABC-Silicone. These studies were carried out at North American Science Associates, Inc. ("NAMSA"). These studies included acute systemic toxicity ISO 10993-11 in mice, intracutaneous ISO 10993-10 in rabbits, maximization sensitization ISO 10993-10 in guinea pigs and a muscle implantation study ISO 10993-6 in rabbits. Results of these in vivo studies demonstrate the safety of C12-3 ABC-Silicone.

Acute systemic toxicity ISO 10993-11 in mice. All the animals were clinically normal throughout the study for the C12-3 catheter segment samples. No mortality was observed during the tests. All the animals gained weight throughout the course of the studies. There was no mortality or evidence of systemic toxicity from the extracts injected into mice. Each test article extract met the requirements of the study for C12-3 ABC-Silicone samples.

Intracutaneous ISO 10993-10 in rabbits. For C12-3 catheter segments, the score was 0.0 for both 0.9% sodium chloride and sesame oil. Both samples met the requirement (score of 1.0 or lower) for this test.

Maximization sensitization ISO 10993-10 in guinea pigs. For C12-3 ABC-Silicone segments, the score was 0 for both 0.9% sodium chloride and sesame oil. Thus, C12-3 segment samples met the requirement for this test. C12-3 segments showed no evidence of causing delayed dermal contact sensitization in the guinea pig. The test article was not considered a sensitizer in the guinea pig maximization test.

Implantation study ISO 10993-6 in rabbits. The macroscopic reaction for C12-3 catheter samples was not significant as compared to the negative control article. Microscopically, C12-3 ABC-Silicone samples caused minimal or no reaction in the tissue as compared to the negative control article. C12-3 ABC-Silicone samples met the requirement for this test.

Based on in vitro 10993-5 biocompatibility studies, similar results are expected for C14-3 ABC-Silicone.

Genotoxicity tests include in vitro and in vivo tests designed to detect compounds that induce genetic damage by various mechanisms. For products that release silver, there is good reason to test for genotoxicity.[1] In contrast, the present inventors believe there is no risk of genotoxicity from ABC-Silicone as the mechanism of biocidal effectiveness is believed to be contact-kill of pathogens with the surface.

Biocompatibility Subacute/Subchronic Toxicity testing complies with ISO 10993-11 and determines the systemic effect of repeated doses of materials or their extracts for no less than 24 hours and no greater than 10% of the total lifespan of the test animal. While there is a potential risk of subacute and subchronic toxicity from silver release by conventional silver-containing devices, the present inventors believe there is no risk of subacute and subchronic toxicity from ABC-Silicone as zone of inhibition and cell compatibility studies support the physical contact kill mechanism for biocidal effectiveness for the ABC-Silicone.

Testing for Pyrogenicity. After administration of a drug or a device, a fever may result. The basis for in vivo testing is a rise in body temperature about one hour after the injection of pyrogens into mammals, such as rabbits or humans. When bacterial pyrogens are injected in sufficient amounts, the fever produced is accompanied by chills, body aches, a rise in blood pressure, and possibly a state of shock and death. The present inventors believe there is no risk of pyrogenicity from ABC-Silicone as zone of inhibition and cell compatibility studies support the physical contact kill mechanism for biocidal effectiveness for the ABC-Silicone without detectable release of species that might be pyrogenic.

A.6. Biocompatibility In Vitro.

A.6.1 In vitro studies. In vitro cytotoxicity assays on ABC-Silicone catheter segments were carried out according to ISO 10993-5 against L-929 mouse fibroblast cells. C14-3 ABC-Silicone gave 100% cell viability, i.e. non-cytotoxic.

The toxicity of leachate to Human Dermal Fibroblast (HDF) cells was evaluated by ISO 10993-5. For comparison, the 10993-5 leachate test for cytotoxicity to HDF cells was also assessed for untreated Bardex® silicone and Bardex® Lubri-Sil® catheter segments. Untreated Bardex® silicone segments, Bardex® Lubri-Sil® catheter segments and C14-3 ABC-Silicone segments gave identical 100% cell viability by the Alamar-Blue™, spectroscopic test. That is, all segments were non-cytotoxic. These results further demonstrate that the antimicrobial effectiveness of the ABC-Silicone does not leach out into the surrounding medium and that the mechanism of action occurs through close contact between bacteria and the treated surface. In terms of biocompatibility and safety, these results demonstrate comparable performance of C14-3 ABC-Silicone to untreated Bardex® silicone and Bardex® Lubri-Sil® catheter segments.

A 10993-5 leachate test for cytotoxicity to HDF cells was also carried out for Covalon Silvertouch™ catheter segments that release silver ions. In contrast to the results described above, the leaching test for Silvertouch™ catheter segments resulted in 0% cell viability suggesting cytotoxicity. This result was the same as for a latex negative control.

A.9. ASTM F1980-2 Shelf-Life/Stability Test. Accelerated Shelf Life Testing is a simulation technique that generates data quickly when actual product lifespan data is unavailable. Simulation is achieved by increased temperature that results in an increased reaction rate.

C-14 ABC-Silicone catheter segments were prepared as described in A.2. These segments were tested for retention of antimicrobial effectiveness according to an ASTM F1980-2 Shelf Life Test. The source for guidance for the test is ASTM F1980-02, Standard Guide for Accelerated Aging of Sterile Medical Device Packages, p. 2. ASTM F1980-2, the "shelf life test" uses an analysis based on the Arrhenius equation that is a commonly used approach for the calculations of aging time. A sample has a decreased activity after 8 weeks at 55° C., an ambient shelf life of approximately 79 weeks is obtained.

C14-3 ABC-Silicone segments were heated at 35° C. or 55° C. for 2, 4, 6 and 8 weeks, respectively. After aging, the respective samples were examined for antimicrobial effectiveness according to ASTM E2149, the shake flask test, against Gram(−) $Klebsiella\ pneumoniae$ (1.66×10$^5$ CFU/mL). After either 35 or 55° C. aging over the course of 8 weeks, an undiminished >log 5 reduction (99.999% kill) was found for $Klebsiella\ pneumoniae$ concentration. The life expectancy was therefore >80 weeks by this metric.

Sometimes bacteria in controls do not grow to the usual level of 10$^5$ cfu/mL. If the level of growth in controls is lower, for example about 10$^4$ cfu/mL at aging time of 6 weeks (FIG. 3), then the log kill is limited by control growth to log 4 or 99.99% kill. There is no decrease in antimicrobial effectiveness as shown by the test at 8 weeks aging. For 8 weeks, the kill returned to a "normal" log 5 as the control grew to log 5 cfu/mL.

As noted above, C14-3 ABC-Silicone technology has shown its strength with 5 log reductions (99.999% kill) of the top two causative organisms, namely $E.\ coli$ and the fungus $Candida\ albicans$.

ABC-silicone exhibits, surprisingly and unexpectedly, strong antimicrobial efficacy against common HAI pathogens including $Escherichia\ coli$, $Candida\ albicans$, $Klebsiella\ pneumoniae$, $Enterococcus\ faecalis$, $Staphylococcus\ epidermidis$, $Klebsiella\ aerogenes$, $Staphylococcus\ aureus$ and $Pseudomonas\ aeruginosa$ as shown by ASTM 2149 "shake flask" tests. Safety for ABC-silicone technology is surprisingly and unexpectedly shown by undetectable leaching in zone of inhibition tests and confirmed by in vitro cytotoxicity tests (ISO 10993-5 standard) and a 100% pass from animal studies of toxicity and sensitivity (ISO 10993-6, 10, 11 standards). ABC-silicone is desirably colorless, odorless, non-toxic, leaching free and eliminates common pathogenic microorganisms by contact. ABC-silicone is desirably cost effective and easy to scale up in industrial manufacturing.

Antimicrobial Resistance Study

Procedure Determining the potential of antimicrobial resistance was carried out on the ABC-silicones. To do this, the ASTM E2149 (Shake Flask) test was utilized. Stock $E.\ coli$ (ATCC) grown overnight to concentration of 10$^8$ CFU/ml was diluted in phosphate buffer saline (PBS) to a working concentration of 10$^5$ CFU/mL. Antimicrobial silicone samples (treated with a 3 wt % C14 ethanol solution) and control samples were added to the inoculated PBS and incubated for 1 h at 37° C. Negative and positive controls were untreated biomedical grade tubing in the working buffer and untreated biomedical grade tubing in working buffer with 8 μg/mL nitrofurantoin (MIC$_{90}$) respectively. After incubation, 100 μL aliquots were plated on to Luria broth (LB) agar plates. Serial dilution of the working PBS was prepared and plated on LB agar to determine number of surviving bacteria. Cultures for successive passages were made by inoculating LB with 100 μL aliquots from the working PBS solution. Cultures were incubated at 37° C. overnight.

Results

WV antimicrobial silicones maintain stable antimicrobial activity after 4 passages with log reductions between 3.5 and 5. The negative controls showed no change in log reduction over 4 passages while with the positive control, log reduction began to decrease after successive passages. This indicated that surviving bacteria in the positive control were developing resistant mutants.

Zeta Potential Measurements

The net charge density on a polymer coating in contact with an aqueous electrolyte such as sodium chloride gives rise to an electrical double layer (EDL) and electroosmosis. In the Guoy-Chapman-Stern (GCS) model, the EDL is comprised of an innermost immobile Stern layer and an outer mobile diffuse layer. The zeta potential (ζ) stems from polarization in an electric field associated with the outer diffuse or slippage layer and provide insight into surface charge. The surface concentration of functional groups, adsorption of ions, effects of pressure and pH are among variables that influence zeta potentials.

Zeta potentials were carried out on a model biomedical grade silicone coating, namely Sylgard 184. In contrast to biomedical grade tubing, Sylgard 184 coatings on microscope slides are amenable to measurements of zeta potentials with a standard instrument. Thus, Sylgard 184 coatings were modified by dimethylalkylamines using the same procedure used for biomedical grade tubing and zeta potentials were investigated to discern trends in surface charge that might correlate with antimicrobial effectiveness via contact kill.

Coating Procedure

Samples were made by coating glass microscope slides with Sylgard 184, a two-part, platinum catalyzed hydrosilylation-cured resin that is often used to mimic a biomedical silicone.[20] The process involved placing 10 g of Sylgard™ 184 silicone resin in a SpeedMixer Max 20 cup followed by 1 g of the Sylgard™ 184 curing agent. The Max 20 cup was then placed in the SpeedMixer and run for one minute at 1750 RPM three times. After the mixture was removed from the SpeedMixer, a plastic transfer pipette was used to coat one side of each slide with ~0.3 g of the reactive resin. The coated slides were placed on a metal tray (coating side up) and put in a preheated oven (100° C.). Samples were removed after 24 h and allowed to cool to room temperature before treatment.

C14 Treatment Procedure

Glass jars were filled with 175 mL of a solution containing various weight percentages of C14 and denatured ethanol. Weight percentages of C14 feed were denoted by the number after C14. For example, a slide treated with a solution containing 5 wt % C14 solution was designated C14-5. The C14 solution was then heated to 40° C. on a heating plate with a magnetic stir bar to ensure the solution was well mixed. Then two slides (for duplicate zeta potential measurements) were placed in the solution and stirred continuously at 40° C. for 1 h. Slides were removed from the solution and rinsed well with deionized (DI) water before being placed in a phosphate buffer solution ($KH_2PO_4$, PBS) for 24 h before determining zeta potentials.

Zeta Potential Measurements

Measurements employed an Anton Paar Surpass Analyzer equipped with a clamping cell (FIG. 3). This cell was assembled with the sample and 0.001 M KCl electrolyte solution.

Results and Discussion

Zeta Potential Measurements. To compare zeta potentials for model biomedical grade Sylgard 184 and compositions modified with alkyldimethylamines, sample geometry, pressure, temperature, pH and electrolyte concentration were held constant. Once fluid flow and electrokinetic forces reach a steady state, the streaming potential and streaming currents can be measured for calculation of the zeta potential.

Zeta Potentials for Amine Modified Sylgard 184. As noted in the Experimental section, Sylgard 184 was treated with N,N-dimethyltetradecylamine, C14 to give compositions that are designated by C14 feed. C14 has a pK of ~10 and therefore any surface concentrated species are expected to be protonated to form $R_3NH^+$ over a wide pH range. The initial hypothesis for the investigating zeta potentials for C14 modified Sylgard 184 was that higher concentrations of might increase $\zeta$ due to an increased presence of $R_3NH^+$.

Zeta potentials are shown in FIG. 29 for Sylgard 184 and samples treated with C14 feed from C14-0.5 to C14-5. Zeta potentials steadily increased from Sylgard 184 to C14-3. Higher C14 feed (C14-4, C14-5) did not show increased zeta potentials. Apparently, a saturation point is reached for surface charge at C14-3.

Table 13 lists the data from FIG. 29 in a tabular format. FIG. 30 shows surface charge density versus zeta potential.

TABLE 13

Zeta potentials, differential zeta potentials and charge density for surface modification of Sylgard 184 by increasing weight percent C14.

| C14 feed (wt %) | Zeta potential ($\zeta$, mV) | Differential zeta potential (Sylgard - C14 feed (wt %) | Charge Density, $\sigma$ (C/cm$^2$) |
|---|---|---|---|
| 0 (Sylgard 184) | −88.5 | 0 | 0.00E+00 |
| 0.5 | −83.5 | 5 | 2.29E+11 |
| 1.0 | −74.5 | 14 | 6.49E+11 |
| 2.0 | −66 | 22.5 | 1.06E+12 |
| 3.0 | −35 | 53.5 | 2.93E+12 |
| 4.0 | −38.5 | 50 | 2.68E+12 |
| 5.0 | −41.5 | 47 | 2.48E+12 |

FIG. 31 shows the relationship of charge density to C14 feed (wt %). An important and nonobvious finding is the maximum in charge density for C14-3. Higher weight percent feed results in a decrease in charge density. A feed of 3 wt % C14-3 appears to saturate the surface with charge. Thus, C14-3 was a preferred composition for antimicrobial testing and studies of biocompatibility.

ASTM E2149 Testing against Uropathogenic *E. coli* (ATCC 700928)

Sample Preparation

Half pipes of biomedical silicone tubing were treated with a 3 wt % C14 amine solution at 40° C. for 1 h. Samples are then washed for 15 min in DI water 3 times to remove unadsorbed amine. After washing, samples that will not be immediately used are stored in PBS buffer.

Shake Flask Testing, ASTM E2149-01

For testing of uropathogenic *E. coli* (ATCC 700928), the ASTM E2149-01 shake flask test was utilized as with previously tested microbes. Stock bacterial solution was cultured in sterile LB medium from a single colony. Bard silicone Foley catheter (Fr. 24) segments were treated with C14-3 as previously described. Treated silicone half-pipes and control samples (untreated catheter segments) were then added to separate flasks at approximately 1.16 cm$^2$/mL surface area to volume ratio. A flask containing just the extraction vehicle and pathogen was also introduced as an additional control parameter. The flasks were then subjected to gentle rotation at 37° C. in an incubator-shaker. Afterwards, aliquots from each flask were removed at selected time intervals then serial diluted and plated on agar. The plates were incubated for 24 h or more at 37° C. and bacterial colonies were then counted to establish log reduction.

Results

C14-3 antimicrobial silicones have shown to be effective against uropathogenic *E. coli* (ATCC 700928) after 24 h exposure. As seen in Table 12, treated silicone tubing had a >log 5 reduction. To confirm that the bacteria was killed rather than inhibited, plates were left at ambient temperature for 24 h. After 24 h no new colonies appeared indicting that the initial exposure resulted in bacteria death.

The contents of each reference, citation, article, ASTM test and ISO test cited herein are hereby incorporated by reference, the same as set forth at length.

What is claimed is:
1. A composition, comprising:
   a physiologically-acceptable polydimethylsiloxane having a surface; and
   one or more normal $C_6$-$C_{20}NR_1R_2$ saturated amine, salt thereof, or combination thereof, in contact with the polydimethylsiloxane, the surface, or both, wherein $R_1$ and $R_2$ may be same or different and independently selected from H, —$CH_3$, —$CH_2CH_3$, —$CH_2CH_2CH_3$, or combination thereof.

2. The composition of claim 1, wherein the amine is not covalently bonded to the polydimethylsiloxane or surface either directly or through a linker.

3. The composition of claim 1, wherein the amine is not ionically bonded to the polydimethylsiloxane or surface either directly or through a linker.

4. The composition of claim 1, wherein the composition is antimicrobial, cytocompatible, antiviral, or combination thereof.

5. The composition of claim 1, wherein the composition is antimicrobial and cytocompatible.

6. The composition of claim 1, wherein the composition is antimicrobial to G+ bacteria, G− bacteria, or both.

7. The composition of claim 1, wherein the composition is stable under ambient conditions.

8. The composition of claim 1, wherein the composition is stable in air, water, saline, physiological fluid, urine, blood, saliva, mucosa, plasma, cerebrospinal fluid, nasolacrimal fluid, tissue, or combination thereof.

9. The composition of claim 1, wherein the $C_6$-$C_{20}NR_1R_2$ amine is a $C_6NR_1R_2$, $C_8NR_1R_2$, $C_{10}NR_1R_2$, $C_{12}NR_1R_2$, $C_{14}NR_1R_2$, $C_{16}NR_1R_2$, $C_{18}NR_1R_2$, or $C_{20}NR_1R_2$ carbon chain amine.

10. The composition of claim 1, wherein the $C_6$-$C_{20}NR_1R_2$ amine is a $C_{10}NR_1R_2$, $C_{12}NR_1R_2$, $C_{14}NR_1R_2$ or $C_{16}NR_1R_2$ carbon chain amine.

11. The composition of claim 1, wherein $R_1$ and $R_2$ are both H.

12. The composition of claim 1, wherein $R_1$ and $R_2$ are both —$CH_3$.

13. The composition of claim 1, wherein the amine is a quaternary amine.

14. The composition of claim 1, wherein the polydimethylsiloxane having a surface is neither oxidized, plasma-treated, corona-treated, flame-treated, chemically modified, nor physico-chemically modified.

15. The composition of claim 1, wherein said $C_6$-$C_{20}NR_1R_2$ amine is N, N-dimethyltetradecylamine or salt thereof.

16. A medical device, comprising the composition of claim 1.

17. A method for making the composition of claim 1, comprising:
contacting a polydimethylsiloxane surface with an ethanolic solution of one or more normal $C_6$-$C_{20}NR_1R_2$ saturated amine, salt thereof, or combination thereof; and drying, to produce the composition.

18. A composition, made by a process comprising:
contacting a physiologically-acceptable polydimethylsiloxane surface with an alcoholic solution of one or more normal $C_6$-$C_{20}NR_1R_2$ saturated amine, salt thereof, or combination thereof; and drying, to produce the composition.

19. The composition of claim 18, wherein the contacting comprises one or more of dipping, spraying, soaking, or a combination thereof of said polydimethylsiloxane surface in or with the alcoholic solution.

20. The composition of claim 18, wherein the amine, salt thereof, or combination thereof is in the form of one or more of a monolayer or multilayer on the surface, is dispersed or absorbed in the polydimethylsiloxane, is dispersed or absorbed in a near-surface portion of the polydimethylsiloxane, or combination thereof.

21. The composition of claim 18, wherein the polydimethylsiloxane is not completely swollen by the amine.

22. The composition of claim 18, wherein the amine may be separated from the polydimethylsiloxane, surface, or combination thereof by exposure to vacuum, organic solvent, acid, base, or combination thereof.

23. The composition of claim 18, wherein the composition is stable to radiative sterilization.

24. A medical or other device, having a surface comprised of the composition of claim 18.

25. A method for treating or minimizing a risk of a bacterial or viral infection in a subject comprising contacting a subject in need of infection treatment or minimization of risk with the composition of claim 1.

26. An antimicrobial, cytocompatible or antiviral surface, comprising the composition of claim 1.

27. A cytocompatible surface, comprising the composition of claim 1.

28. A method of killing or reducing a population of bacteria or virus, or reducing the growth rate of a population of bacteria or virus, comprising contacting the bacteria or virus population with the composition of claim 1.

* * * * *

UNITED STATES PATENT AND TRADEMARK OFFICE
CERTIFICATE OF CORRECTION

| | |
|---|---|
| PATENT NO. | : 11,666,686 B2 |
| APPLICATION NO. | : 17/867252 |
| DATED | : June 6, 2023 |
| INVENTOR(S) | : Kenneth J. Wynne et al. |

It is certified that error appears in the above-identified patent and that said Letters Patent is hereby corrected as shown below:

On the Title Page

Item (54), and in the Specification Column 1 Line 1 please delete the entire Title and replace with the following new Title:
--ANTIMICROBIAL SILICONES--.

Signed and Sealed this
Second Day of July, 2024

Katherine Kelly Vidal
*Director of the United States Patent and Trademark Office*